United States Patent
Zilberg

(10) Patent No.: US 8,021,309 B2
(45) Date of Patent: Sep. 20, 2011

(54) ALGORITHM FOR AUTOMATIC POSITIVE AIR PRESSURE TITRATION

(75) Inventor: Eugene Zilberg, Sandringham (AU)

(73) Assignee: Compumedics, Ltd., Abbotsford, Victoria (AU)

( * ) Notice: Subject to any disclaimer, the term of this patent is extended or adjusted under 35 U.S.C. 154(b) by 1525 days.

(21) Appl. No.: 11/179,911

(22) Filed: Jul. 12, 2005

(65) Prior Publication Data

US 2005/0241639 A1 Nov. 3, 2005

Related U.S. Application Data

(63) Continuation of application No. PCT/IB2004/000704, filed on Jan. 30, 2004.

(60) Provisional application No. 60/443,762, filed on Jan. 30, 2003.

(51) Int. Cl.
*A61B 5/08* (2006.01)
(52) U.S. Cl. .................. 600/538; 600/534; 128/204.18; 128/204.23
(58) Field of Classification Search .................. 600/538, 600/534; 128/204.18, 204.19, 204.21, 204.23, 128/204.26
See application file for complete search history.

(56) References Cited

U.S. PATENT DOCUMENTS

| | | | | |
|---|---|---|---|---|
| 5,492,113 A | * | 2/1996 | Estes et al. | 128/204.23 |
| 6,305,374 B1 | * | 10/2001 | Zdrojkowski et al. | 128/204.21 |
| 6,488,634 B1 | * | 12/2002 | Rapoport et al. | 600/538 |
| 6,948,497 B2 | * | 9/2005 | Zdrojkowski et al. | 128/204.18 |
| 2003/0078619 A1 | * | 4/2003 | Bonnet et al. | 607/4 |

* cited by examiner

*Primary Examiner* — Patricia Mallari
*Assistant Examiner* — Michael D'Angelo
(74) *Attorney, Agent, or Firm* — Scott H. Davison; Procopio, Cory, Hargreaves & Savitch, LLP

(57) ABSTRACT

An algorithm for measuring the breathing of a patient for diagnosing breathing disorders and for controlling a breathing aid device for treating a patient. Sensors record pressure and flow rates of air delivered to a patient. The data is statistically manipulated to find the start of a breath, the end of a breath, the duration of a breath, the shape of a breath, the volume of a breath, the breathing rates, flow rates, snoring index, flattening index, and other useful data to diagnose and treat a patient. The data is used to diagnose the condition of a patient and to control a breathing aide device for treating a patient at the most optimal pressures and flow rates for the patient's condition. Inspiration and expiration data are tracked separately and compared throughout the algorithm as a check the accuracy of the data manipulation by the algorithm.

77 Claims, 31 Drawing Sheets

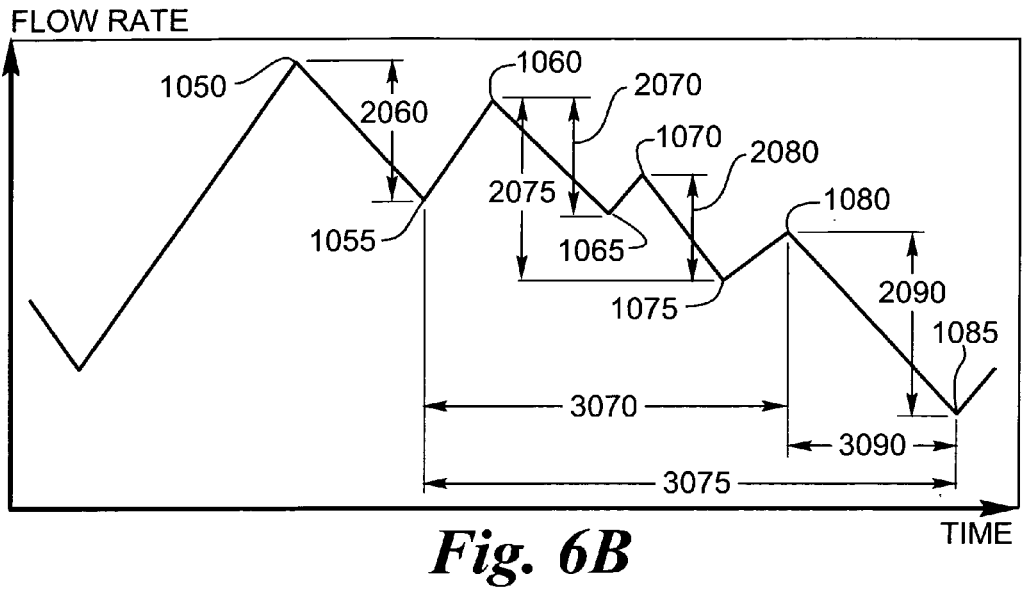

*Fig. 6B*

| | Dur_fromright<br>- .75 s | Dur_fromright<br>> .75 s and - 1.125 s | Dur_fromright<br>> 1.125 s and - 1.5 s | Dur_fromright<br>> 1.5 s |
|---|---|---|---|---|
| Dur_fromleft<br>- .75 s | 2.25; 1.33<br>2.00; 1.50<br>1.75; 1.75<br>1.50; 2.00<br>1.33; 2.25 | 2.25; 1.50<br>2.00; 1.75<br>1.75; 2.00<br>1.50; 2.25<br>1.33; 2.50 | 2.25; 1.75<br>2.00; 2.00<br>1.75; 2.25<br>1.50; 2.50<br>1.33; 2.75 | 2.25; 2.00<br>2.00; 2.25<br>1.75; 2.50<br>1.50; 2.75<br>1.33; 3.00 |
| Dur_fromleft<br>> .75 s<br>and<br>- 1.125 s | 2.50; 1.33<br>2.25; 1.50<br>2.00; 1.75<br>1.75; 2.00<br>1.50; 2.25 | 2.50; 1.50<br>2.25; 1.75<br>2.00; 2.00<br>1.75; 2.25<br>1.50; 2.50 | 2.50; 1.75<br>2.25; 2.00<br>2.00; 2.25<br>1.75; 2.50<br>1.50; 2.75 | 2.50; 2.00<br>2.25; 2.25<br>2.00; 2.50<br>1.75; 2.75<br>1.50; 3.00 |
| Dur_fromleft<br>> 1.125 s<br>and<br>- 1.5 s | 2.75; 1.33<br>2.50; 1.50<br>2.25; 1.75<br>2.00; 2.00<br>1.75; 2.25 | 2.75; 1.50<br>2.50; 1.75<br>2.25; 2.00<br>2.00; 2.25<br>1.75; 2.50 | 2.75; 1.75<br>2.50; 2.00<br>2.25; 2.25<br>2.00; 2.50<br>1.75; 2.75 | 2.75; 2.00<br>2.50; 2.25<br>2.25; 2.50<br>2.00; 2.75<br>1.75; 3.00 |
| Dur_fromleft<br>> 1.5 s | 3.00; 1.33<br>2.75; 1.50<br>2.50; 1.75<br>2.25; 2.00<br>2.00; 2.25 | 3.00; 1.50<br>2.75; 1.75<br>2.50; 2.00<br>2.25; 2.25<br>2.00; 2.50 | 3.00; 1.75<br>2.75; 2.00<br>2.50; 2.25<br>2.25; 2.50<br>2.00; 2.75 | 3.00; 2.00<br>2.75; 2.25<br>2.50; 2.50<br>2.25; 2.75<br>2.00; 3.00 |

*Fig. 7*

| The partitions of FI according to the values of FI_ave and FI_max (2 breaths) | | |
|---|---|---|
| FI | FI_ave (%) | FI_max (%) |
| VF | -10 | -25 |
| F | (10 14) | (25 29) |
| MF | (14 18) | (29 33) |
| SF | (18 22) | (33 37) |
| NF | >22 | >37 |

Reduction in Flow Signal (RFS) partitions

| The partitions of reduction of flow signal according to the values of flattening index and inspiration flow signal level | | |
|---|---|---|
| RFS | ΔFI | ΔFI |
| SR | -60% | -80% |
|  | >60% | -60% |
| IR | >60 | [60 80] |
|  | <60 | -80% |
| MR | >60 | >80% |

*Fig. 28*

| The partitions of snoring index for the snoring-related rules | |
|---|---|
| SI | Minimum value of snoring index |
| NS (no snoring) | <3 l/min. |
| S (snoring) | ³3 l/min. |

*Fig. 29*

| The partitions of snoring index for the other control rules | |
|---|---|
| SI | Average value of snoring index |
| NS (no snoring) | -2 l/min. |
| MS (moderate snoring) | [2 4] l/min. |

*Fig. 30*

| The snoring related control rules | | | | |
|---|---|---|---|---|
| SI_min \ P_ave | P - 6 | P = [6 12] | P = [12 16] | P = [16 18] |
| ³3 l/min | ΔP = 0.4<br>RP = [4 20] | ΔP = 0.3<br>RP = [4 20] | ΔP = 0.2<br>RP = [4 20] | ΔP = 0.1<br>RP = [4 20] |

*Fig. 31*

| The flattening-related rules for the 5-breath test data set | | | |
|---|---|---|---|
| FI \ RFS | SR | IR | MR |
| VF | ΔP = 0.5 cm H₂O<br>RP = [4 18] cm H₂O | ΔP = 0.4 cm H₂O<br>RP = [4 16] cm H₂O | ΔP = 0.3 cm H₂O<br>RP = [4 14] cm H₂O |
| F | ΔP = 0.4 cm H₂O<br>RP = [4 16] cm H₂O | ΔP = 0.3 cm H₂O<br>RP = [4 14] cm H₂O | ΔP = 0.2 cm H₂O<br>RP = [4 12] cm H₂O |
| MF | ΔP = 0.3 cm H₂O<br>RP = [4 14] cm H₂O | ΔP = 0.2 cm H₂O<br>RP = [4 12] cm H₂O | N/A<br>N/A |
| SF | ΔP = 0.2 cm H₂O<br>RP = [4 12] cm H₂O | N/A<br>N/A | N/A<br>N/A |

*Fig. 32*

| The flattening-related rules for the 5-breath test data set | | | |
|---|---|---|---|
| FI \ RFS | SR | IR | MR |
| VF | ΔP = 0.25 cm H₂O<br>RP = [4 18] cm H₂O | ΔP = 0.20 cm H₂O<br>RP = [4 16] cm H₂O | ΔP = 0.15 cm H₂O<br>RP = [4 14] cm H₂O |
| F | ΔP = 0.20 cm H₂O<br>RP = [4 16] cm H₂O | ΔP = 0.15 cm H₂O<br>RP = [4 14] cm H₂O | ΔP = 0.10 cm H₂O<br>RP = [4 12] cm H₂O |
| MF | ΔP = 0.15 cm H₂O<br>RP = [4 14] cm H₂O | ΔP = 0.10 cm H₂O<br>RP = [4 12] cm H₂O | N/A<br>N/A |
| SF | ΔP = 0.10 cm H₂O<br>RP = [4 12] cm H₂O | N/A<br>N/A | N/A<br>N/A |

*Fig. 33*

| The flattening-related rules for the 2-breath test data set ||||
|---|---|---|---|
| RFS / FI | SR | IR | MR |
| VF | ΔP = 0.125 cm H₂O<br>RP = [4  18] cm H₂O | ΔP = 0.100 cm H₂O<br>RP = [4  16] cm H₂O | ΔP = 0.075 cm H₂O<br>RP = [4  14] cm H₂O |
| F | ΔP = 0.100 cm H₂O<br>RP = [4  16] cm H₂O | ΔP = 0.075 cm H₂O<br>RP = [4  14] cm H₂O | ΔP = 0.050 cm H₂O<br>RP = [4  12] cm H₂O |
| MF | ΔP = 0.075 cm H₂O<br>RP = [4  14] cm H₂O | ΔP = 0.050 cm H₂O<br>RP = [4  12] cm H₂O | N/A<br>N/A |
| SF | ΔP = 0.050 cm H₂O<br>RP = [4  12] cm H₂O | N/A<br>N/A | N/A<br>N/A |

*Fig. 34*

| The mixed flattening and snoring-related rules for the 3-breath test data set ||
|---|---|
| SI / FI | MS |
| VF | ΔP = 0.5 cm H₂O<br>RP = [4  18] cm H₂O |
| F | ΔP = 0.4 cm H₂O<br>RP = [4  16] cm H₂O |
| MF | ΔP = 0.3 cm H₂O<br>RP = [4  14] cm H₂O |
| SF | ΔP = 0.2 cm H₂O<br>RP = [4  12] cm H₂O |

*Fig. 35*

| Pressure increase rules for apneas ||||
|---|---|---|---|
| P_ave / FL_var | P < 6 | P = [6  12] | P ³ 12 |
| - 100 ml/s | ΔP = 2.0<br>RP = [4  20] | ΔP = 1.0<br>RP = [4  20] | ΔP = 0.5<br>RP = [4  20] |

*Fig. 36*

| Similarity Test | | | | | |
|---|---|---|---|---|---|
| Number of max-pairs (min-pairs) in the sequence | Mean Index | 1 | 2 | 3 | 4 |
| | 3 | 12 | 11 | 9 | 7 |
| | 4 | 13 | 12 | 10 | 8 |
| | 5 | 14 | 13 | 11 | 9 |
| | 6 | 15 | 14 | 12 | 10 |

*Fig. 37*

| | Maximum Flattening Index | | | Average Flattening Index | | |
|---|---|---|---|---|---|---|
| Flow Limitation Category \ Breaths | 2 | 3 | 5 | 2 | 3 | 5 |
| Severe | 0-23 | 0-25 | 0-25 | 0-8 | 0-10 | 0-10 |
| Large | 24-27 | 26-29 | 26-29 | 9-12 | 11-14 | 11-14 |
| Medium | 28-31 | 30-33 | 30-33 | 13-16 | 15-18 | 15-18 |
| Mild | 32-35 | 34-37 | 34-37 | 17-20 | 19-22 | 19-22 |

*Fig. 38*

| Flattening Index Context \ Peak Inspiratory Flow Context | Large Reduction | Small Reduction | No Reduction |
|---|---|---|---|
| Reduction | Clear Obstruction Context | Clear Obstruction Context | Mild Obstruction Context |
| No Reduction | Clear Obstruction Context | Mild Obstruction Context | No Obstruction Context |

*Fig. 39*

| Number of Breaths | Snore Detected | Leak Detected | Obstruction/ Peak Inspiratory Flow Reduction Context Category | Pressure Increase - Severe Flow Limitation cm $H_2O$ | Maximum Pressure - Severe Flow Limitation cm $H_2O$ | Reduction in Pressure Increase per Flow Limitation Category cm $H_2O$ | Reduction in Maximum Pressure per Flow Limitation Category cm $H_2O$ | Mildest Flow Limitation Category |
|---|---|---|---|---|---|---|---|---|
| 2 | No | No | Clear Obstruction | 0.125 | 18 | 0.025 | 2 | Mild |
| | | | Mild Obstruction | 0.100 | 16 | 0.025 | 2 | Medium |
| 3 | Yes | No | Any | 0.500 | 18 | 0.100 | 2 | Mild |
| | No | No | Clear Obstruction | 0.250 | 18 | 0.050 | 2 | Mild |
| | | | Mild Obstruction | 0.200 | 16 | 0.050 | 2 | Medium |
| | | | No Obstruction | 0.150 | 14 | 0.050 | 2 | Large |
| 5 | No | No | Clear Obstruction | 0.500 | 18 | 0.100 | 2 | Mild |
| | | | Mild Obstruction | 0.400 | 16 | 0.100 | 2 | Medium |
| | | | No Obstruction | 0.300 | 14 | 0.100 | 2 | Large |
| | | Yes | Flow Reduction | 0.250 | 18 | 0.050 | 2 | Mild |
| | | | No Flow Reduction | 0.150 | 14 | 0.050 | 2 | Large |

*Fig. 40*

| Actual rules: Pressure increase is calculated according to the table ||
|---|---|
| Average pressure cm $H_2O$ | Pressure increase cm $H_2O$ |
| 0-6 | 0.4* Confidence coefficient |
| 6-12 | 0.3* Confidence coefficient |
| 12-16 | 0.2* Confidence coefficient |
| 16-18 | 0.1* Confidence coefficient |

*Fig. 41*

ALGORITHM FOR AUTOMATIC POSITIVE AIR PRESSURE TITRATION

CROSS-REFERENCE TO RELATED APPLICATIONS

This application is a Continuation of PCT International Application No. PCT/IB2004/000704, filed Jan. 30, 2004, which designated the United States, and on which priority is claimed under 35 U.S.C. §120, and which claims priority under 35 U.S.C. §119(e) to U.S. Provisional Application No. 60/443,762, filed Jan. 30, 2003.

BACKGROUND OF THE INVENTION

1. Field of the Invention

This invention relates to a method for deriving inspiration periods, expiration periods and flow rates from raw breathing flow rate data by using a half duration breath method for determining breath flow rates, and to detect flow limitation, snoring, apnea and hypopnea while eliminating noise and breathing aberrations from the flow data such that a controller on machines for treating sleep disorders can appropriately optimize the air pressure applied.

2. Description of the Related Art

In some devices pressure measurements have been used to detect abnormal breathing. In other devices methods of detecting breathing patterns use a combination of pressure and flow rates. Still other devices use airflow measurements alone where the variance in the airflow detects an apnea at an indexed value of the mid point of a normalized inspiratory flow.

Some flow rate systems for determining if a patient is inhaling or exhaling calculate an average flow rate. When the flow rate exceeds the average the patient is inhaling, when the flow rate is below average the patient is exhaling.

Another method for detecting inspiration or expiration is by use of high and low thresholds compared to a first derivative of the gas flow curve of gas delivered to the patient.

None of the methods used to date accurately detect the beginning of inspiration, the beginning of expiration or the duration and flow rates of a breath. The detection devices used to date also fail to accurately analyze or monitor breaths for snoring, apneas, hypopneas, or pauses and shifts in breathing patterns. Further the current breathing measurement devices do not accurately remove noise from the measurements.

The present breathing detectors do not measure and balance the inspiration and expiation flows.

A more accurate breath measuring method is required to provide data for sleep breathing disorder studies, to control sleep aid breathing machines and to monitor patients.

SUMMARY OF THE INVENTION

The invention relates to a method for providing accurate patient breathing data. The data can be used for studies, for monitoring patients or for providing breathing information to a controller on a CPAP or other breathing aid to adjust the pressure and flow of air to a patient for improved treatment.

A mask is applied to a patient for providing air under pressure to the patient being monitored or treated for a breathing disorder. Sensors in the mask or tubes attached to the mask determine the flow rates of air to the patient. Mask and tube leak rates are subtracted from the raw data to determine the airflows actually received by the patent. The actual flow rate data is then analyzed to remove noise, perturbations and other signals to accurately determine when inspiration and expiration begin and end and determine the flow rates of air to the patient. The data is smoothed and checked for possible errors in the data to find the best fit of data representing an accurate representation of the patients breathing. The inspiration and expiration volumes are compared for accuracy and adjustments of the measurements. The data is then analyzed to detect the breathing of the patient and can be used to drive breathing aid devices. The data can be used to detect apneas, hypopneas, snoring, and other medical conditions as well as simply monitoring for if the mask is off, if the patient is breathing through their nose or mouth, if the patient has shifted positions or changed sleep stages and is now breathing differently.

The process for detecting the breaths of the patient includes the steps of measuring the pressure and flow rates of the air supplied to a patient through a mask. Approximating the break points of the breath for identifying the inspiration and expiration periods of each breath. Compiling inspiration flow rate data and expiration flow rate data separately into a continuous array of inspiration data and a continuous array of expiration data. Smoothing the inspiration and expiration data to establish an array of inspirations and expirations having a beginning point a peak point and an ending point. Forming an array of such smoothed data for both the inspiration flow rate data and the expiration flow rate data. Eliminating those inspiration and expiration periods from the array that have excessive noise in the flow rate data so as to compare signals without excess noise in the breath analysis. Comparing the inspiration flow volumes in the arrays to the expiration flow volumes as a check on the accuracy of the data manipulation in the arrays. Comparing adjacent pairs of inspiration periods (or expiratory periods) for similarity of the breaths so as to compare like kind breaths in the breath analysis. Comparing the inspiration start and end points to the expiration start and end points to check on the accuracy of the flow rate data. Compiling a series of like kind breaths for testing the breathing of the patient. Adjusting the beginning and ending points of the breaths and the maximum points of the breaths to fit the flow rate data collected. Performing a signal level verification test to eliminate breaths that are too close together or mask off situations from the data used for the breath analysis. Comparing the volumes of the inspirations and expirations of the breaths to make sure they are the same as a check on data quality. Then using the flow rate data to perform breath shaping and finalize the beginning and ending of inspiration times in the flow rate data based on the breath shape. The flow rate data can now be used for diagnosing the patient's breathing. To provide the diagnosis the data is used to produce a snoring index to show if the patient is snoring and to what extent, and a flattening index to show the degree of blockage in the patient's airway which is related to apneas and hypopneas. Inspiratory flow amplitude is used to identify apneas and hypopneas.

Many statistical measurements are used to determine breath similarity, beginning of inspiration and expiration times, ending of inspirations and expirations, breath durations, volumes of air in each breath, breaths per minute, the shape of each breath, and other measures all of which are useful in diagnosing the breathing problems experienced by a patient. Once the algorithm determines the problems being experienced by a patient it can control a machine for treating the patient to provide the best pressures for the best airflows at the best times to treat the patient for his breathing problems. The extensive statistical analysis of pressures and airflow rates applied to the patient provide a breath analysis useful for patient diagnosis and treatment.

OBJECTS OF THE INVENTION

It is an object of the invention to control the pressure delivered to a patient using a breathing mask during treatments for apnea, hypopnea and other breathing disorders.

It is an object of the invention to measure the breathes of a patient to apply the correct pressure at the correct time to treat the patient.

It is an object of the invention to provide an algorithm for measuring the breathing of a patient and calculating the pressure to be applied to the patient during his breathing cycles.

It is an object of the invention to detect snoring.

It is an object of the invention to detect inspiratory flow limitations.

It is an object of the invention to detect flow amplitude reduction.

It is an object of the invention to detect apnea.

It is an object of the invention to detect hypopnea.

It is an object of the invention to detect breathing periods and breath shapes.

It is an object of the invention to detect inspiration and expiration start and end points during the breathing cycle.

It is an object of the invention to eliminate noise and other perturbations of breath flow rate measurements.

It is an object of the invention to distinguish between changes in respiration patterns and a regular breath.

It is an object of the invention to provide accurate monitoring of a patient's breathing.

It is an object of the invention to detect abnormal breath periods.

It is an object of the invention to compare inspiration volumes to expiration volumes to control the accuracy of the data output.

Other objects, advantages and novel features of the present invention will become apparent from the following description of the preferred embodiments when considered in conjunction with the accompanying drawings.

BRIEF DESCRIPTION OF THE DRAWINGS

FIG. 6B is a graph of a decreasing noisy slope.

FIG. 7 table of noisy slope parameter limitations to be met.

FIG. 28 is a table showing reduction in flow signal levels from FIG. 27.

FIG. 29 is a table showing partitions for the snoring index.

FIG. 30 is a table showing snoring index control rules.

FIG. 31 is a table showing snoring index control rules.

FIG. 32 is a table showing flattening-related rules for 5-breath test data.

FIG. 33 is a table showing flattening-related rules for 3-breath test data.

FIG. 34 is a table showing flattening-related rules for 2-breath test data.

FIG. 35 is a table showing flattening and snoring-related rules for 3-breath test data FIG. 36 is a table showing pressure increase rules for apneas.

FIG. 37 is a table showing the similarity test values.

FIG. 38 is a table showing flattening flow limitations in the main breath test sequence.

FIG. 39 is a table showing flattening inspiratory flow contexts.

FIG. 40 is a table showing a flattening pressure change rules template.

FIG. 41 is a table showing snoring pressure change rules.

DESCRIPTION OF THE PREFERRED EMBODIMENTS

Figure 1:
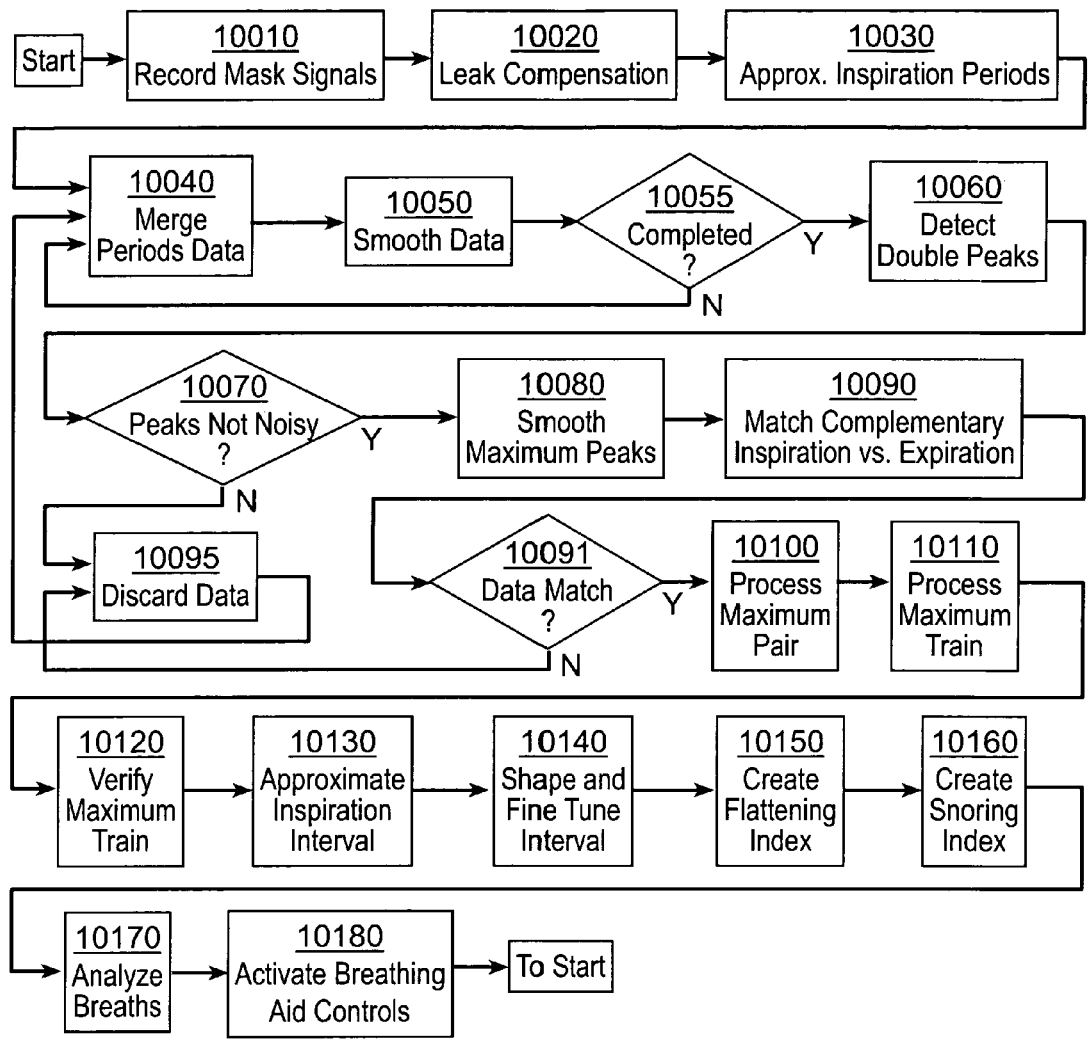
FIG. 1 is a flow chart of the algorithm for automatic positive air pressure titration.

The algorithm for the automatic positive air pressure titration is shown in FIG. 1. The first step in the algorithm is to receive and record the airflow rate signal data from the mask collected at specified time increments as shown at block 10010. The data from the mask is then compensated for leaks as shown at block 10020 and the data recorded. The raw flow rate data is searched at block 10030 and a first rebuttable approximation of an inspiration or expiration period is established. The data is then merged with a previously collected inspiration or expiration period data at block 10040 (or stored if no previous data is available) and then the data is smoothed and stored as part of an array of data at block 10050. If the data array is not complete as determined in block 10055 then more raw data is collected from block 10030 approximating the next inspiration or expiration period and merged into the array at block 10040 and the data is then smoothed and stored at block 10050. If the array is now complete as determined in block 10055 then the array is checked for double peaks at block 10060 and checked for noisy peaks at block 10070. If noisy peaks are detected at step 10070 they are smoothed by piecewise linear approximation at block 10080. All breaths are then checked to see if their inspiration volumes match their complementary expiration volumes in block 10090. In block 10091 a test is conducted to see if the inspiration volume matches the expiration volume. The inspiration volume should match the expiration volume otherwise there is an error in the data and the data will have to be discarded. Data not matching is discarded at block 10095. If the inspiration and expiration data match the algorithm proceeds to block 10100 for comparing pairs of inspirations or expirations for similarity. If they are similar the data is assumed to be good and no changes in breathing have occurred. The first maximum train test is the similarity test run in block 10110 of the algorithm. It tests the similarity between the maximum pairs in the maximum train. In the verification at block 10120 data is recalled from the initial global max-peak and min-peak array generated at block 10110 and compare the closest min-peak array, as the inspiration beginning point in the maximum peak array should match the expiration ending point of the minimum peak array and the expiration beginning point in the maximum peak array should match the inspiration ending point of the minimum peak array.

Block 10130 approximates the inspiration and expiration break points which are fine-tuned in block 10140 to determine a closer approximation of the inspiration and expiration points and shapes the breaths.

Block 10150 then checks for the flattening index from the inspiration flow signal.

The flattening index is used to measure the flow limitations such as occur in apneas.

Snoring is checked in block 10160 by the noise found in the flow signal. A snoring index is produced and is used in the control rules to increase or decrease pressure and flow volumes to a patient to reduce snoring.

A breath analysis is then performed in block 10170 to determine if the patient is experiencing an apnea, hypopnea or other breathing disorder, or is there is some airway restriction, if the mask has come off or if the patient is snoring.

In block 10180 a set of control rules are applied to treat the conditions identified in the breath analysis step. For example the pressure applied to the patient by a CPAP machine may be increased or decreased.

A more detailed explanation of the algorithm is now presented.

In treating a patient with continuous positive airway pressure (CPAP) a mask is utilized to provide air under pressure to a patient. Measurements of air flow and air pressure are made by transducers in the mask or in the tubes connecting the mask to an air pressure source to obtain flow and pressure signals for monitoring the patient and determining when the patient is inhaling, exhaling, snoring, or experiencing apnea or hypopnea. The raw pressure and flow data signals are collected at block 10010 in the algorithm. The signals have to be processed to provide meaningful and accurate readings of the patient's state and to determine the pressure to be supplied to the patient during treatment. There are many challenges to obtaining accurate data since a patient's breathing is not uniform and no two patients are alike. In each breath the patient may inhale at a different rate over a different period of time. Further the patient may pause for different amounts of time between inhaling and exhaling. The patient may then exhale at different rates over different periods of time and then pause again before inhaling. The patient will be shifting positions during the night, which will affect breathing rates. The patient may also be experiencing differing amounts of airway blockage during the night. Add to these variables snoring, apnea events and hypopnea events and it becomes very difficult to measure the patient's breathing to determine when he is inhaling, exhaling, snoring or experiencing apnea or hypopnea so that a CPAP device or BiPAP device can be adjusted to the right pressure to most efficiently and effectively aid the patient. Further the raw data gathered contain noise such as the air pump and motor, the air delivery circuit and other perturbations, which diminish the accuracy of the signals obtained. Possible aberrations in the signals are that the mask may have come off, a hose may have become disconnected or bent, or the patient may have begun breathing though his mouth.

When a patient dons a mask used in conjunction with his treatment the first problem to address is that the mask itself will leak so that a flow leak compensation factor must be used on the flow data signals received from the mask to reflect the difference between the measured flow and the flow actually applied to the patient. The mask leaks occur at the mask interface with the patient (mask edge leak flow) and the mask connection to the air supply hose (port leak flow).

The port leak flow is different for each mask type used and the pressure applied to the mask. A port leak flow look up table can be used to estimate the flow loss depending on the pressure. The port leak flow is subtracted from the measured flow to help approximate the actual flow to the patient. Similarly the mask edge leak flow can be estimated by using a low pass filter to filter out the flow going to the patient leaving the balance of the flow signal attributable to the mask edge leakage. With the leak flows determined the balance of the airflow goes to the patient and is recorded as the airflow data at block 10020 of the algorithm.

Although the leak rates have been formulated as shown above other means for determining the flow rates may be used in conjunction with various masks and port connections.

With flow and pressure signals of air actually supplied to the patient available at block 10020 analysis begins on the characterization of the individual breaths.

The algorithm uses half duration flow rates of the breaths. The algorithm determines the maximum flow rate during inspiration periods and the minimum flow rates during expiration periods for measuring the breaths of the patient and processes them separately for comparison and then combines them later on in the process. The algorithm used eliminates flow rate signal noise and time gaps between inspiration and expiration to provide a more accurate measure of inspiration and expiration periods and the flow rates experienced by the patient while breathing.

In order to identify inspiration and expiration flows with greater accuracy the algorithm takes in a jumble of raw data with noise and signal aberrations and smoothes out the data using a number of techniques to the eliminate noise and aberrations to provide an easier to read more accurate representation of the patient's breathing rate. The algorithm uses approximations and statistical techniques on the signal data collected to identify the beginning and ending of the inspiration and expiration cycles and the maximum and minimum flow rates in each breath. The data generated is used to control a breathing device such as a CPAP machine used to treat a patient.

Figure 2:
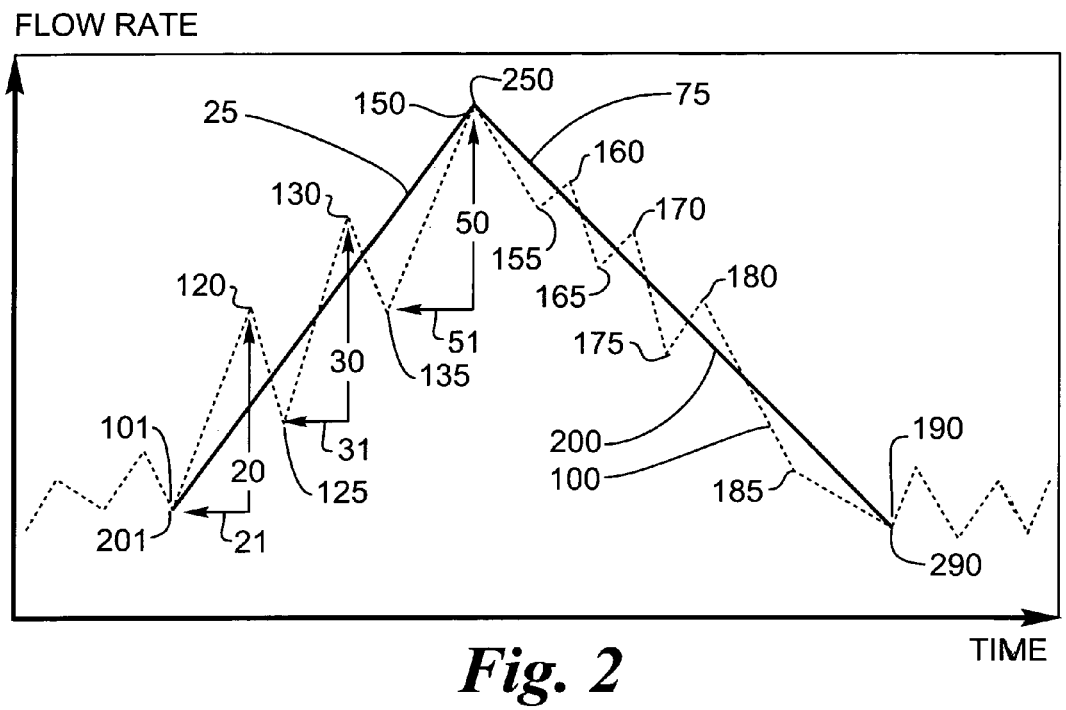
FIG. 2 is a graph of a smoothed maximum peak from raw inspiration flow data.

FIG. 2 shows a series of flow signal data points taken at specified time periods such as 10 hertz or 250 hertz and plotted with a dashed line 100 which represents the raw signal data collected. The starting point of inspiration is chosen at a point called a break point where the data indicates a positive flow rate and a significant increase in the flow rate begins thereafter. The selection of the break point is performed in block 10030 of the algorithm. The break point is chosen as point 101 marking the beginning of inspiration. The inspiration data is full of noise, perturbations and errors. The raw data points progress generally higher with inconsistently increasing values over time at points 120, 125, 130 and 135 to a maximum flow rate during inspiration at point 150 and then inconsistently decreases at points 155, 160, 165, 170, 175, 180 and 185 to an inspiration ending point 190. The noise and aberrations in the raw data providing the jagged signal shown by dashed line 100. The maximum flow rate point 150 is the highest of the peaks at about the middle of the inspiration period, and the end point of the inspiration 190 is at a point chosen by the algorithm to be at about the same flow rate as the start of inspiration at point 101. The end of inspiration at point 190 is also the beginning of expiration for the same breath.

FIG. 2 also shows a linear smoothing technique, represented by block 10050. The smoothing process is used to approximate the breath flow rate of the patient and eliminate signal noise and aberrations. The points 101, 150 and 190 of dashed line 100 are equal to the points 201, 250 and 290 respectively on the solid line 200. A first order linear technique shown in FIG. 2 simply connects the beginning of inspiration at point 201 and the maximum peak 250 by an upward sloping line 25. Similarly a downward sloping line 75 is defined by connecting the maximum peak 250 with the end of inspiration point 290. The resulting more ideal, easier to work with smoothed graph of a patient's inspiration is shown by solid line 200. The smoothed graph using line 200 has removed noise and variations of flow rates to more clearly show the start of inspiration at start point 201, the maximum flow during inspiration approximately in the middle of the inspiration cycle at flow rate peak 250 and the end of the inspiration cycle at end point 290 which should be equal to the beginning of the expiration cycle of the patient's breath. The duration of the breath is the time between points 201 and 290.

The algorithm is used to track expirations as well as inspirations but here we only track the inspirations for ease of explanation. It should be readily understood from graphing the inspirations that expirations are similarly graphed.

Figure 3:
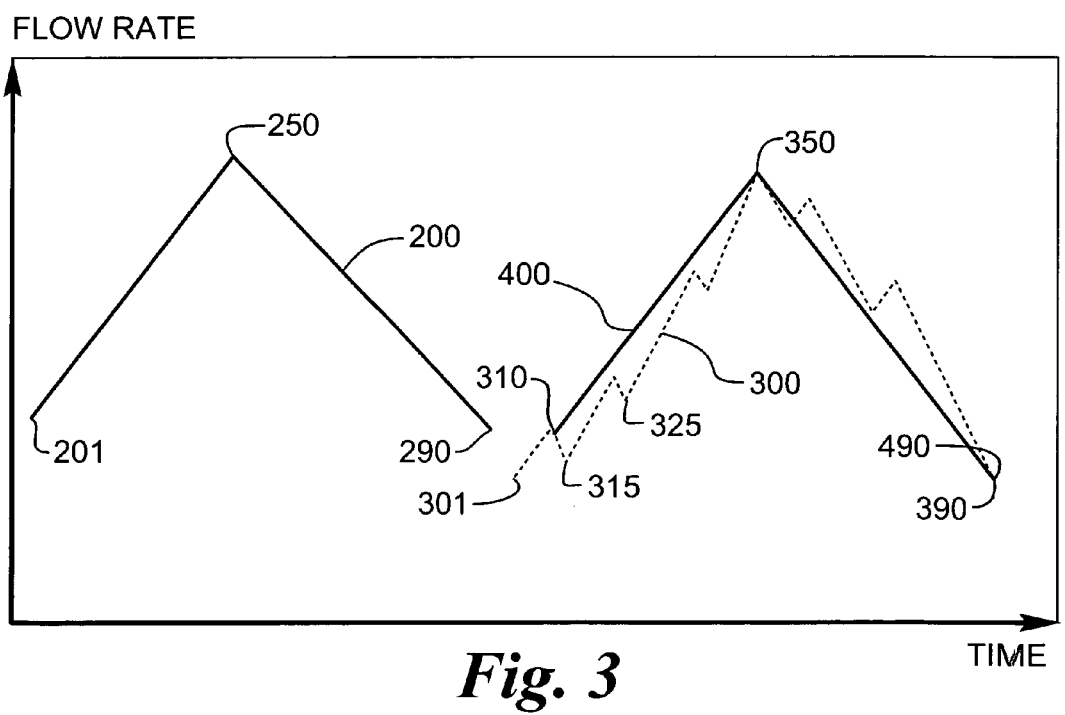
FIG. 3 is a graph of a raw data inspiration to be added to a prior smoothed inspiration.
Figure 5:
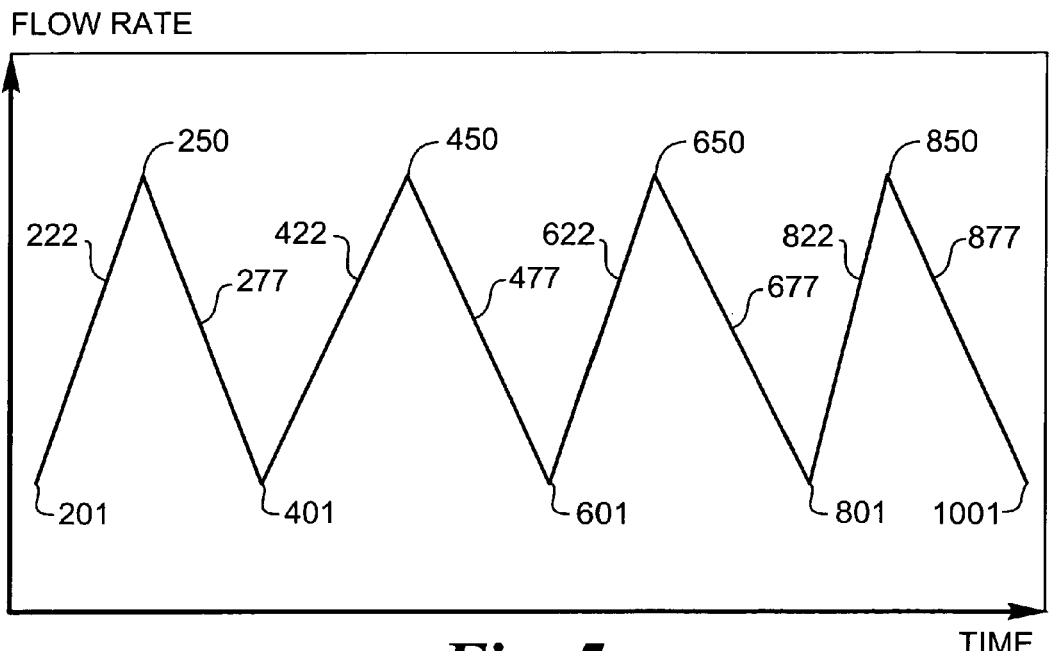
FIG. 5 is a graph of an array of smoothed inspirations.

The algorithm obtains a series of inspirations for analysis of breaths in real time. There are many possible methods for adding strings of inspiration data together. In order to make the most efficient use of time, data processing and storage resources, the technique presented here is to merge raw data from a succeeding inspiration period to the previously smoothed inspiration data at a time just after the processor has finished smoothing a previous inspiration, as depicted in algorithm block 10040. With the techniques used the starting point of the next inspiration is somewhat random compared to the ending of the previous inspiration. FIG. 3 graphically indicates a new raw flow inspiration data set represented by dashed line 300, with estimated inspiration start point 301, estimated maximum peak flow rate 350, and estimated end of inspiration point 390. This raw data set represented by dashed line 300 is merged with previously smoothed inspiration data represented by solid line 200. The data from lines 200 and 300 will be merged and then the second inspiration data from dashed line 300 is smoothed as solid line 400. The solid lines are added together to yield a smoothly connected series of smoothed inspiration flow rates as shown in FIG. 5.

The time that the new data represented by dashed line 300 is available may be before the end of the smoothing of the previous breath, concurrently with the ending of smoothing of the prior breath, or after the smoothing of the previous breath. Further, the flow rates at the beginning and end of the breaths will vary and have to be adjusted to fit smoothly on FIG. 5.

Figure 3A:
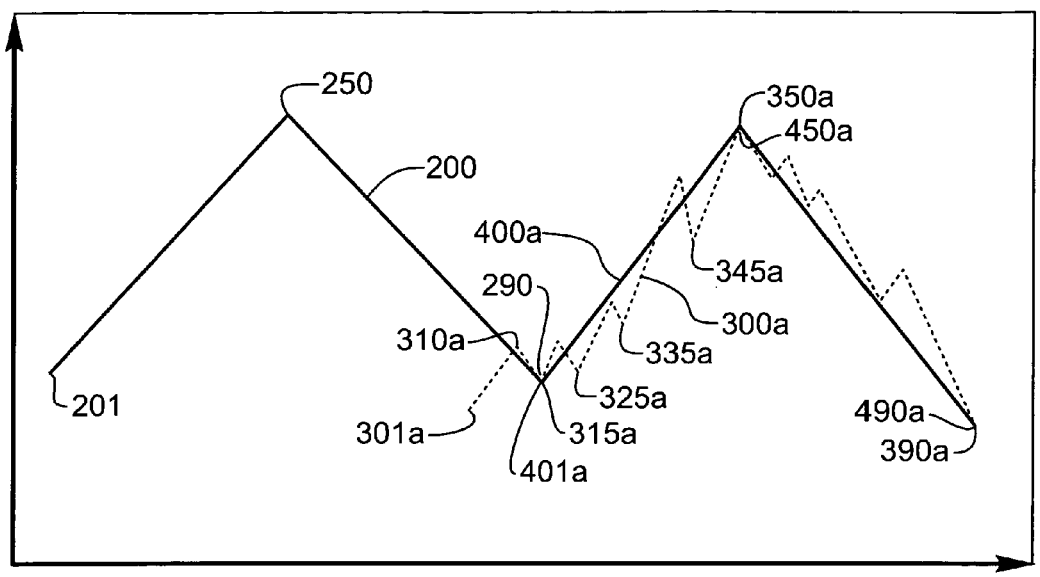
FIG. 3A is a graph of a raw data inspiration available early to be added to a prior smoothed inspiration with a trough point close to the end point.

There are five main scenarios for merging a new inspiration data set with a previous inspiration data set as shown in FIGS. 3A, 3B, 3C, 3D and 3E. In the first scenario as depicted in FIG. 3A, which is the most typical situation, smoothing ends at the flow rate point 290. The algorithm selected the approximate beginning of inspiration of the next breath with a flow rate shown at point 301a. This point was selected at a time before the ending of the smoothing process at point 290. Therefore the best fit in real time for the overlapping graphs is to match the nearest trough 315a of the new flow rates to the smoothed point 290 representing the end of inspiration from the previous breath. Here the flow rate at trough point 315a in the new inspiration matches, or is very close to, the flow rate value of the previous inspiration at point 290 so the gap between the end of the first inspiration at 290 and the beginning of the next inspiration data at point 301a is overlooked and the second inspiration is plotted as beginning from point 315a of the second breath raw data. The new raw data set has a peak flow rate at 350a and an end of inspiration period at 390a. The second breath is then smoothed to produce a plot of the inspiration as shown by solid line 400*a*. The smoothed second inspiration then has starting at point 401*a*, a maximum point at 450*a* and an ending of inspiration at point 490*a*.

Figure 3B:
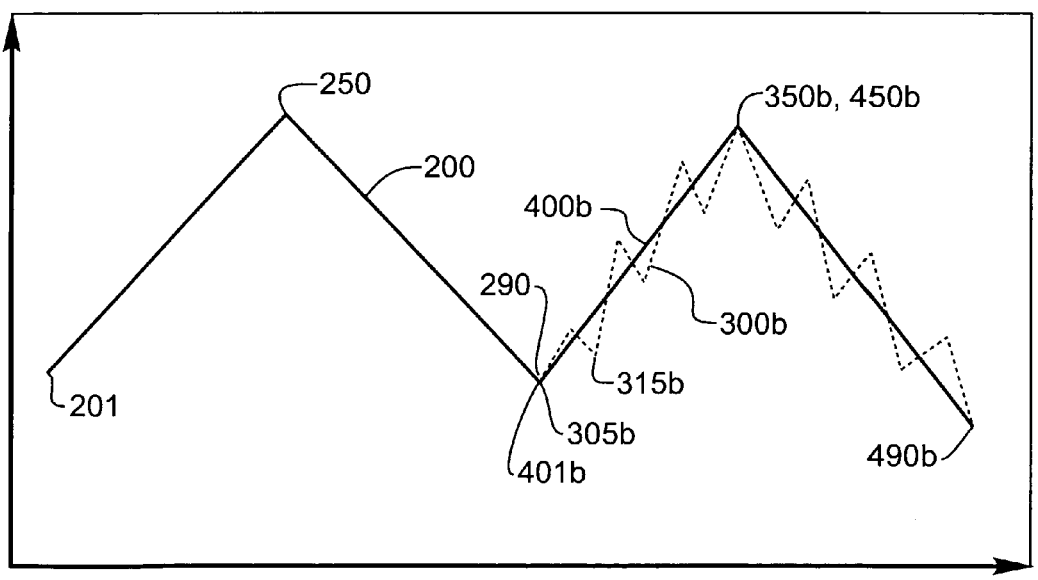
FIG. 3B is a graph of a raw data inspiration available just in time to be added to a prior smoothed inspiration.

In a special case scenario, shown in FIG. 3B, the ending flow rate of inspiration at point 290 of a first breath is the same, or close to, the beginning flow rate 301*b* of the second inspiration and the timing of the calculations is such that the smoothed inspiration ends at point 290 just as the new data is available at point 301*b*. The second inspiration raw flow rate data as shown by dashed lines 300*b* is then locally smoothed to yield the graph shown by solid line 400*b*, having a start of inspiration at 401*b*, a maximum peak at 450*b* and an ending of inspiration at point 490*b*.

Figure 3C:
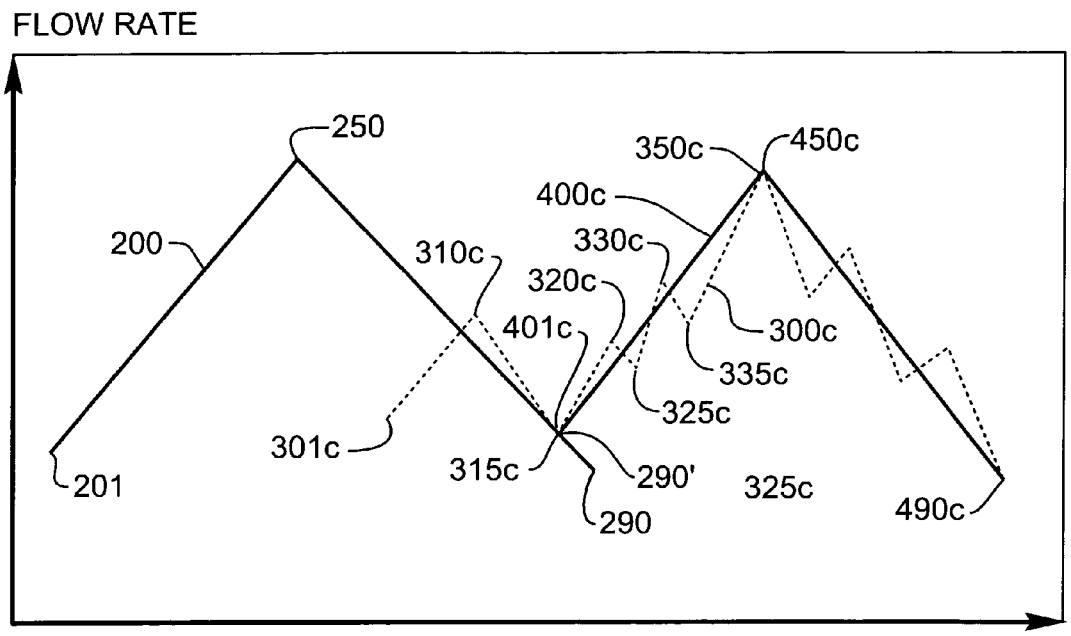
FIG. 3C is a graph of a raw data inspiration to be added to a prior smoothed inspiration with a trough point not close to the end point.

In the scenario shown in FIG. 3C the smoothed inspiration data ends at point 290. The next inspiration data shown by dashed line 300*c* is available at a time plotted by point 301*c*, which starts at a time well before the end of the smoothing calculations end at point 290. There can be many reasons for the variations in timing including shifts in the patients breathing patterns. The raw data for the next breath shown by dashed line 300*c* is stored and compared for the best fit to the smoothed data for the previous breath ending at point 290. The smoothed value of the inspiration flows from the previous breath 200 match the value in the raw data of inspiration flow of the new breath at trough point 315*c* for the best fit of time and values between the two graphs. The new breath 300*c* is therefore started at point 315*c* and smoothed to obtain graph 400*c*. Therefore the last portion of smoothed line 200 is ignored and the effective smoothed position of the end of the previous breath is moved up to 290' to match the beginning of the next inspiration at 315*c*. The new breath is then smoothed to start at 401*c*, peaking at 450*c*, and ending at 490*c*.

Figure 3D:
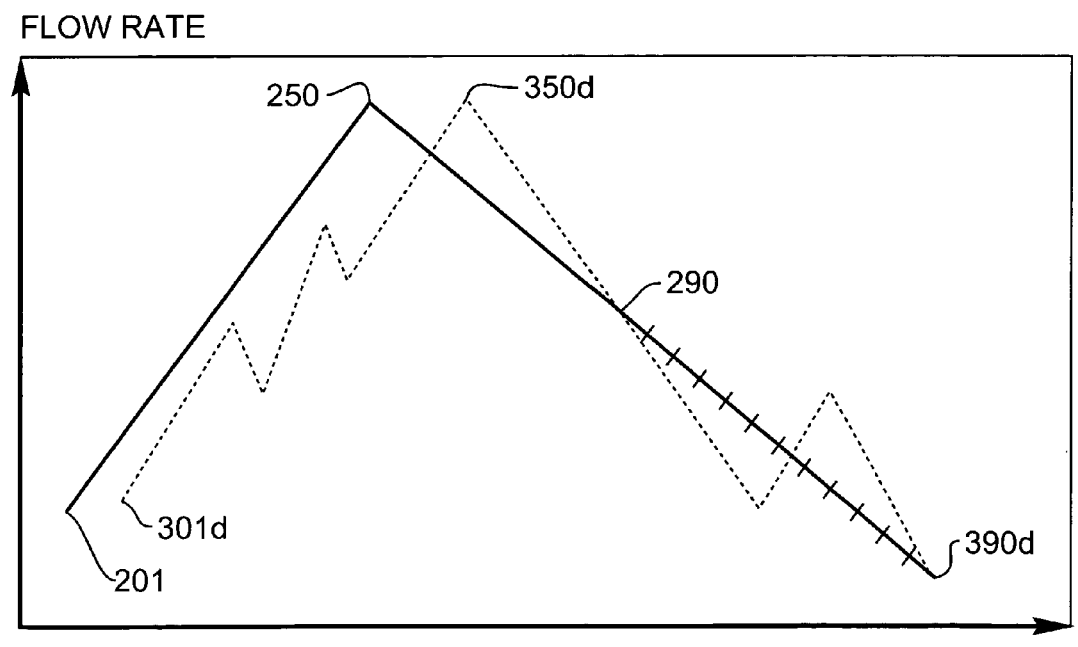
FIG. 3D is a graph of a raw data inspiration available very early to be added to a prior smoothed inspiration by extending the tail of otherwise essentially overlapping data.

In the scenario shown in FIG. 3D the prior smoothed breath begins at point 201 has a maximum peak at point 250 and ends at point 290. The next inspiration raw data beginning at point 301*d* is available immediately after the beginning of smoothed inspiration data at point 201. The beginning portions of the two breathes are approximately equal but the tail end of the inspirations are not. The new data extending to lower inspiration flow rates. The best fit begins at a point where the values of flow rate 290 and the downward slope of raw data from breath 300 are the same, and ends at the flow rate 390*d* at the end of breath 300. The downward slopes of breath 200 and 300 are added after point 290 to extend the smoothed graph to the end of inspiration at point 390*d* as shown by the hashed solid line.

Figure 3E:
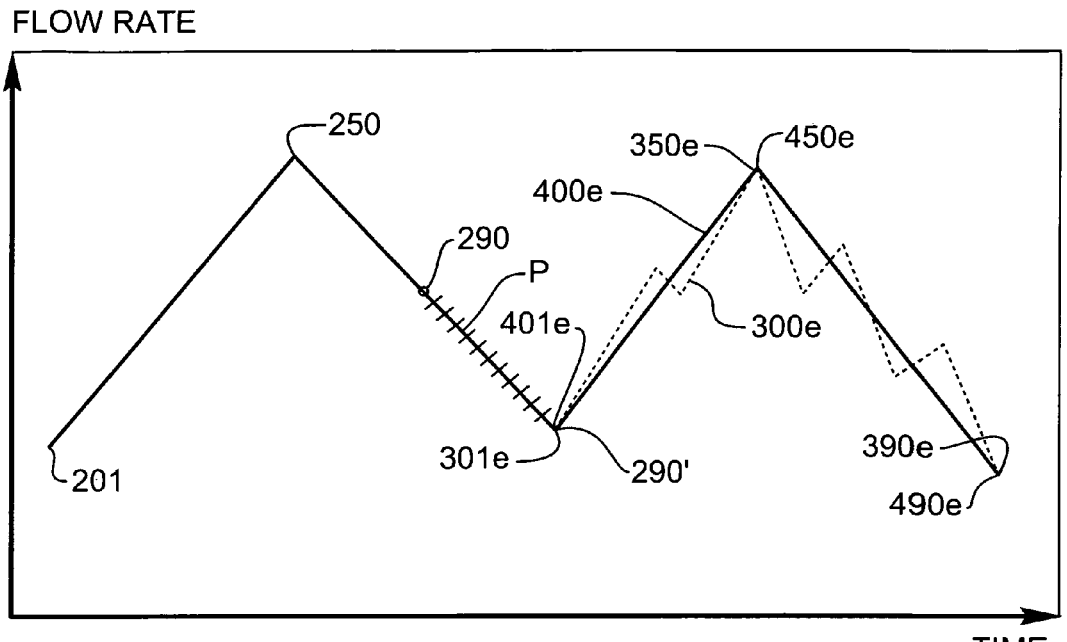
FIG. 3E is a graph of a raw data inspiration available late to be added to a prior smoothed inspiration by extending the tail of the first breath to cover non overlapping data.

In the scenario shown in FIG. 3E the smoothed inspiration has been plotted ending at point 290 and the algorithm has to wait for new raw data to become available for the next inspiration beginning at point 301*e*. A gap exists between the values, which must be patched in. The best fit is to add a patch P, shown by the hashed solid line between points 290 and 290', to cover the gap between the end of the prior inspiration at 290 and the beginning of the new inspiration at point 301*e* connecting the lowest flow rates from both the end of the last inspiration to the lowest flow rate of the new inspiration. The new breath raw data starting at point 301*e* extending to maximum at 350*e* and ending at 390*e* is then smoothed to add to the inspiration array from the beginning of inspiration at point 401*e*, to a maximum peak at point 450*e* and to the end of inspiration at point 490*e*.

Large delays of breaths are suspect in that changes in breathing patterns may be taking place.

Figure 4A:
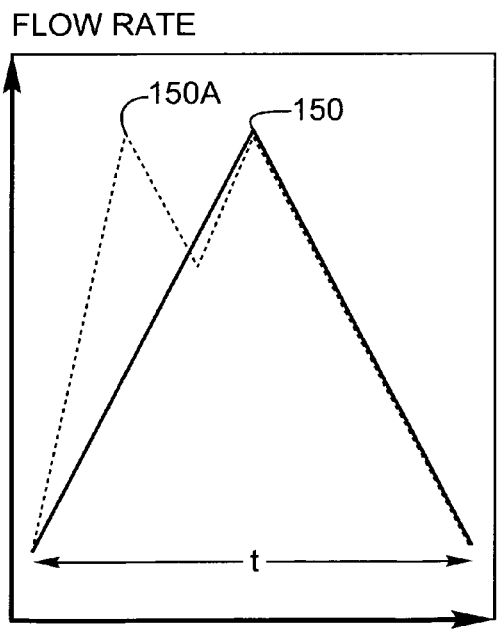
FIG. 4A is a double peak on the increasing slope of the inspiration.
Figure 4B:
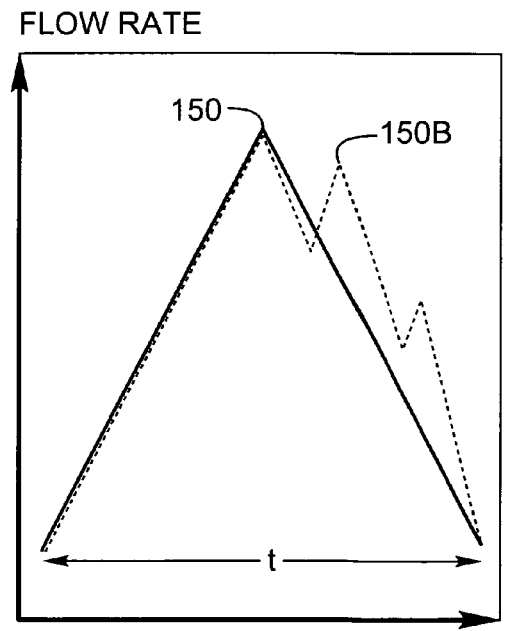
FIG. 4B is a double peak on the decreasing slope of the inspiration.

The array of smoothed inspirations as in FIG. 5 may produce two succeeding maximum peaks at short time intervals as shown in FIGS. 4A and 4B. Peaks at short intervals are suspect and must be checked. One possible cause for the error would be a noise induced large peak fooling the algorithm into misdiagnosing an inspiration period. Another possible cause for the error is the real time nature of processing the array of maximum peaks. FIG. 4A shows an increasing smoothed slope with two maximum peaks 150 and 150A very close together. FIG. 4B shows a decreasing smoothed slope with two maximum peaks 150 and 150B very close together. As shown in FIGS. 4A and 4B, two maximum peaks occur inspiration interval t. The true maximum flow rate is selected as the one closest to the middle of the inspiration time interval t. The dashed lines show the smoothed inspirations with two maximum peaks too close together during a time interval t. The continuous lines show the resmoothed inspiration eliminating the double peak. The double peaks are checked in the algorithm in block 10060.

After an array of 2 to 4 max peaks have been established as shown in FIG. 5 the algorithm, in block 10070, looks back at the maximum peaks 850, 650, 450 and 250 to disqualify some of them from representing inspiration maximum peaks due to excess noise making the raw data unreliable. If a noisy slope is disqualified the raw data is examined by a piecewise linear analysis to redraw the slope using 1, 2 or 3 lines as will be shown infra.

Figure 6A:
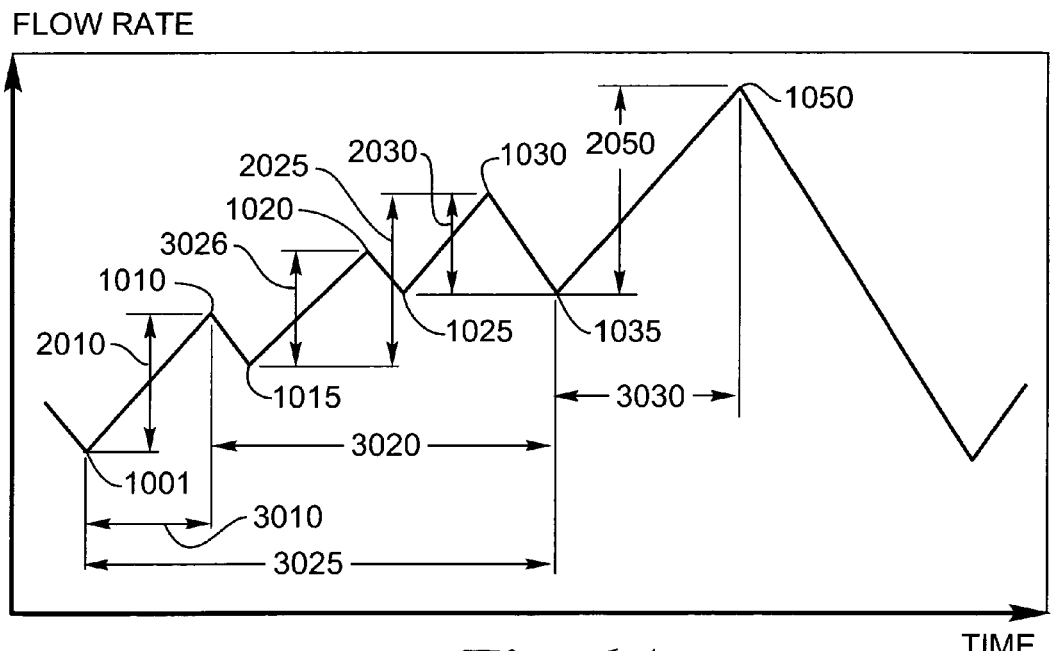
FIG. 6A is a graph of an increasing noisy slope.

The raw data used for producing the smoothed increasing slopes 222, 422, 622 and 822 are examined to see if they are noisy slopes. As seen in FIG. 6A the starting variation 2010 in the flow signal from the start of inspiration at point 1001 to the first peak 1010 and the ending variation 2050 from the trough at point 1035 to the maximum peak 1050 are compared and the smaller variation is defined as the external variation. Variations 2020 and 2030 for peaks 1020 and 1030 respectively are examined and variation between the lowest point 1015 and the highest point 1039 on the variations is defined as the internal variation 2025. If the slope has an external variation 2010 or 2050 larger than the internal variation 2025 then the test group is likely to be a noisy slope. If the increasing slope is not a noisy slop then the downward slope as shown in FIG. 6B is tested to see if it has a noisy slope. In FIG. 6B the starting variations 2060 and ending variations 2090 are measured for peaks 1050 and 1080 respectively representing the maximum and ending peaks on the decreasing slope to find the smaller of the two, which is designated as the external variation. Then the variations for the remaining peaks 1060 and 1070 are examined and variation between the lowest point 1075 and the highest point 1060 on the variations is defined as the internal variation 2025. If the slope has an external variation 2060 or 2090 larger than the internal variation 2075 between points 1060 and 1075, then the internal variation the test group is likely to have a noisy slope.

Only one noisy slope is selected for ease of conducting the noisy slope tests. To test the noisy slopes within the groups additional parameters are used. For the increasing slope shown in FIG. 6A there is a left duration 3010, an internal duration 3020 and the right duration 3030. The left duration 3010 is the time between the start of inspiration at point 1001 and the first peak at 1010. The internal duration is the time between peak 1010 and trough 1035. The right duration is the time between trough point 1035 and maximum peak point 1050. These parameters are used in conjunction with the starting variation 2010, between points 1001 and 1010, the internal variation 2025, between points 1015 and 1030, and the end variation 2050 between points 1035 and 1050.

Another parameter used is the number of peaks between the first peak in the slope and the last peak. For example in FIG. 6A there are two peaks 1020 and 1030 between the first peak 1010 and the last peak 1050. In FIG. 6B there are two peaks 1060 and 1070 between the first peak 1050 and the last peak 1080.

The break points are the beginning and ending of the inspiration flow rates. In FIG. 2 point 201 is the left break point and 290 is the right break point. In FIG. 6A the break point is 1001 and in FIG. 6B the break point is 1085.

Internal maximum peaks are now checked to see if they should be disqualified and excluded from the array. Two groups of measurements are used, the duration from the left and duration from the right.

The following definitions are used as shorthand on the charts used herein:
Duration from the left=Dur_fromleft
Duration from the right=Dur_fromright
Left Duration=Dur_left
Right Duration=Dur_right
Internal Duration=Dur_int
Start Variation=Var_start
End Variation=Var_end
Internal Variation=Var_int
Number of Peaks=Num_peak
The following are definitions for parameters used herein:
Dur_fromleft=Dur_left+Dur_int
Dur_fromright=Dur_right+Dur_int
Ratio_left=Var_left/Var_int–(Num_peak+1)/5
Ratio_right=Var_right/Var_int–(Num_peak+1)/5

If the left and right variations in the duration of the breaths and the ratios of the variations in flow rates for the left and right portions of the breath over the internal variations averaged over the number of breaths in the test groups are not within certain parameters the noise is excluded by approximating the data by a 1, 2, or 3 line piecewise linear method.

The table in FIG. 7 can be used to exclude breaths not falling within acceptable parameters.

The tests for breaths are conducted as follows:

Using the duration from the left measurements (Dur_fromleft) 3010 and the duration from the right measurements (Dur_fromright) 3030, where, as shown in FIG. 6A, the left duration 3010 is the time between points 1001 and 1010 and the interval duration 3020 is the time between points 1010 and 1035 such that the duration from the left 3025 is the time between point 1001 to point 1035. Dur_fromleft=Dur_left+Dur_int.

The duration from the right 3075 is shown in FIG. 6B the right duration 3090 is the time between points 1080 and 1085 and the interval duration 3070 is the time between points 1055 and 1080 such that the duration from the right is the time between point 1055 to point 1085. Dur_fromright=Dur_right+Dur_int.

The variation left 2010 is shown in FIG. 6A. var_left=var_start

The variation right 2090 is shown in FIG. 6B. var_right=var_end.

The Ratio_left=Var_left/Var_int–(Num_peak+1)/5
The Ratio_right=Var_right/Var_int–(Num_peak+1)/5

If the duration is small and the internal signal variation is relatively small compared to the external ratio, left ratio, or ratio right, then the internal max-peaks are highly likely to be excluded. If the duration is large the threshold for the variation ratio is high.

If any of the conditions in the tables of FIG. 7 are met then the internal max peaks 1010, 1020 and 1030 within the group as shown in FIG. 6A group are disqualified. FIG. 7 is a table of threshold values for the ratios used in the comparisons.

For the combinations of durations from the left and durations from the right values the threshold values in each box on the table in FIG. 7 have to be true according to the following formula to have a non-noisy slope.

RatioLeft>=Left_Threshold1 and
RatioRight>=RightThreshold1 or

RatioLeft>=Left_Threshold2 and
RatioRight>=Right_Threshold2 or

RatioLeft>=Left_Threshold3 and
RatioRight>=Right_Threshold 3 or

RatioLeft>=Left_Threshold4 and
RatioRight>=Right_Threshold4 or

RatioLeft>=Left_Threshold5 and
RatioRight>=Right_Threshold5

Each box of quintet pair the table of FIG. 7 are for the left and right threshold values as follows:
Left_Threshold1; Right_Threshold1
Left_Threshold2; Right_Threshold2
Left_Threshold3; Right_Threshold3
Left_Threshold4; Right_Threshold4
Left_Threshold5; Right_Threshold5

For example 2.25 and 1.33 are the Left_Threshold1 and RightThreshold1 thresholds for the first set of values in the duration from the left and duration from the right being less than 0.75 s. The second threshold values 2 and 1.5 are the Left_Threshold2 and RightThreshold2 thresholds for the first set of values in the duration from the left and duration from the right being less than 0.75 s.

If any of the max peak test groups meets one of the conditions in the table of FIG. 7, the internal max-peaks within this group are considered disqualified and need to be excluded because the raw data used was too noisy to give a good result.

Figure 9A:
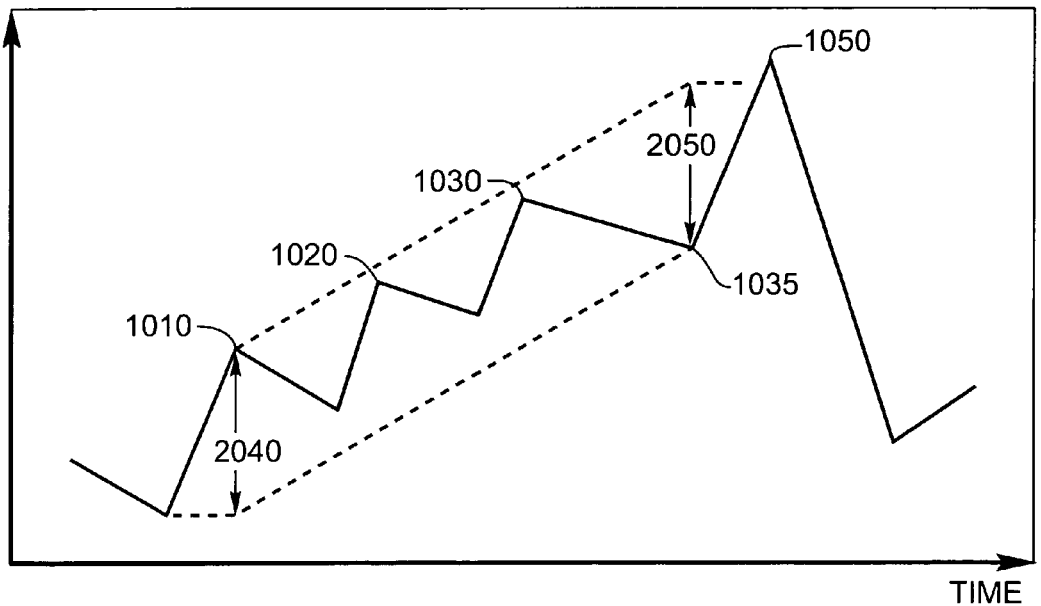
FIG. 9A shows a graph of small peak detection on an increasing slope by use of a parallelogram.
Figure 9B:
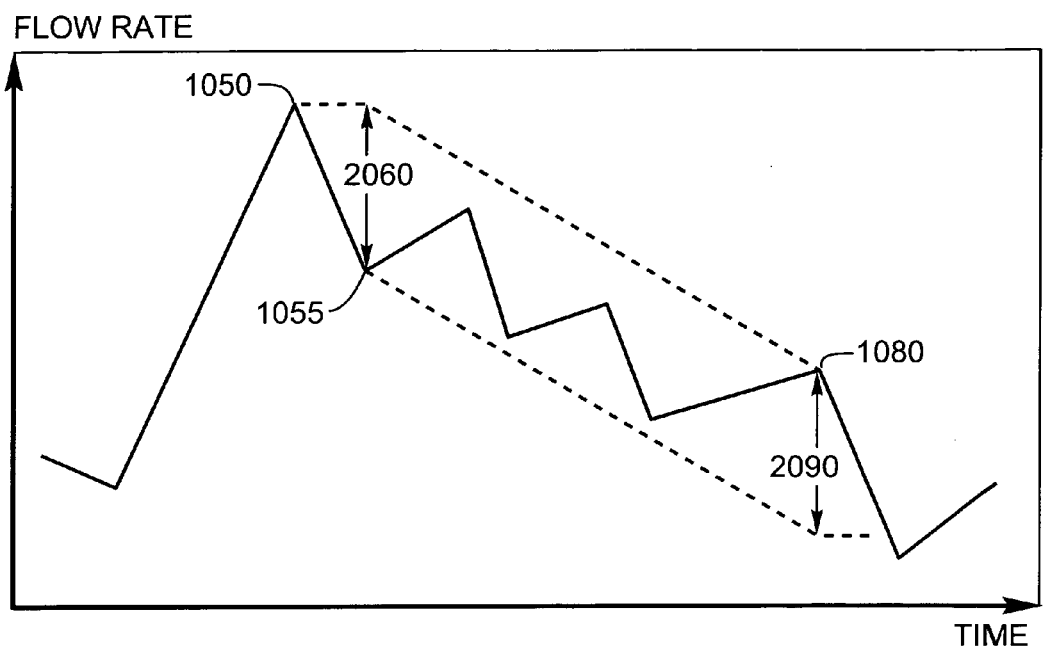
FIG. 9B shows a graph of small peak detection on a decreasing slope by use of a parallelogram.

The nature of the tests presented in the Table in FIG. 7 can be more readily understood by reference to the parallelograms shown in FIGS. 9A and 9B, wherein the raw data for the smoothed array of FIG. 5 is tested for finding excessive signal noise levels. As shown in FIG. 9A an increasing noisy slope with an external variation Var_ext 2040 and the end variation Var_end 2050 has a parallelogram drawn between them. If the raw signal data are inside of the parallelogram the raw data are considered to contain noise but are not too noisy. Similarly for a decreasing noisy slope, as shown in FIG. 9B, if the peaks are within the parallelogram defined by external variation Var_ext 2060 and end variation Var_end 2090 the peaks are considered noise. The decreasing noisy slope in FIG. 9B is within the parallelogram and so it is not a noisy slope.

Thus, for example if the increasing slope 422 in FIG. 5 is considered a noisy slope by testing the raw data in the above conditions, the maximum peak 450 is eliminated from the maximum peak array by deleting the inspiration flow rates from point 401 to 601 and replacing it with a piecewise linear approximation which smoothes these maximum peak patterns by a linear approximation using a first, second or third order linear equation having one, two, or three lines to approximate the inspiration flow rates, respectively. An error rating for each on the first, second or third order approximation methods is used to see which produces the least error and should therefore be the method selected. The first second and third order approximations and error rankings will be explained infra.

Figure 8A:
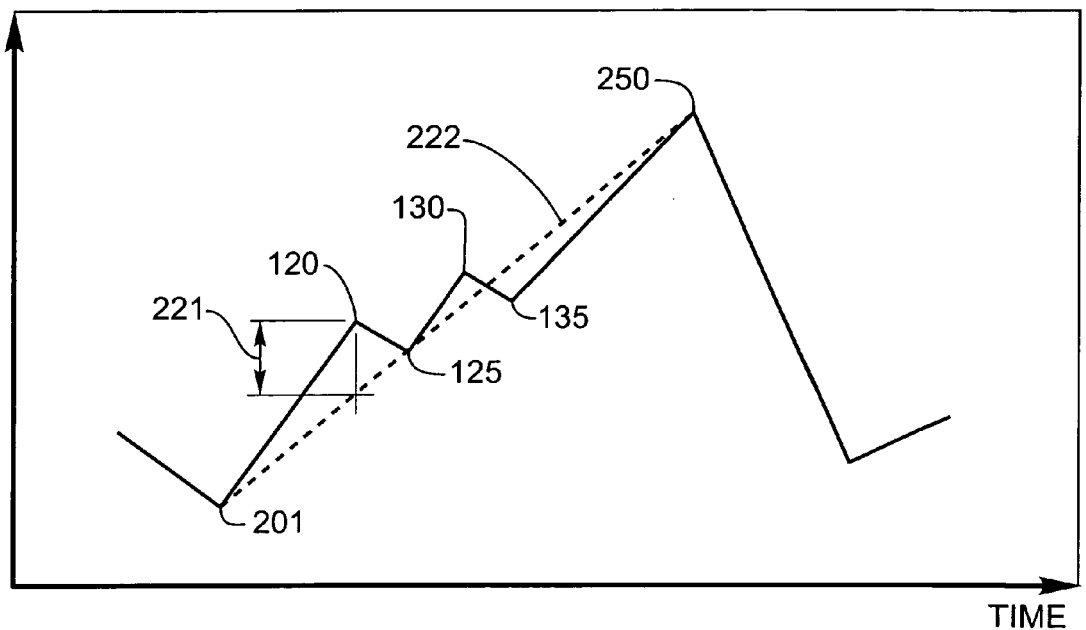
FIG. 8A shows a graph of the first order piecewise linear methods for approximating the flow rates.
Figure 8B:
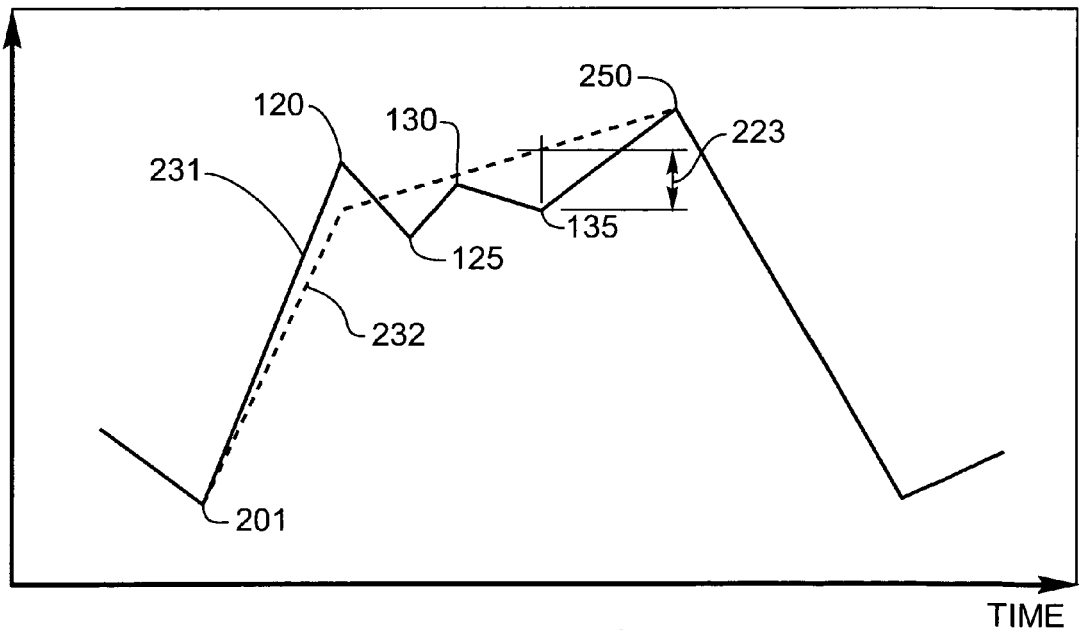
FIG. 8B shows a graph of the second order piecewise linear methods for approximating the flow rates.
Figure 8C:
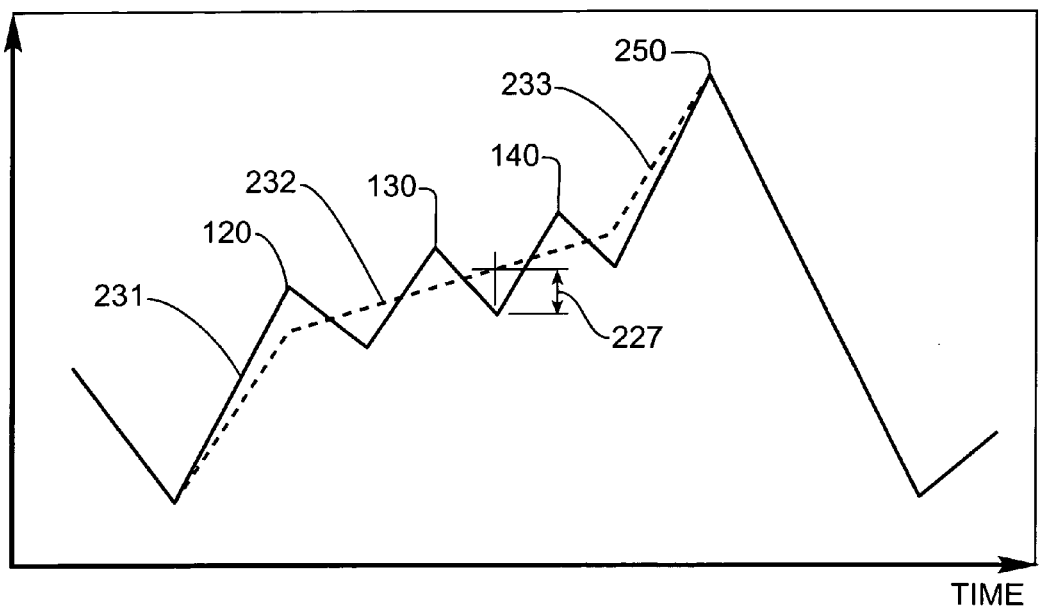
FIG. 8C shows a graph of the third order piecewise linear methods for approximating the flow rates.

FIGS. 8A, 8B and 8C show graphs of the first second and third order piecewise linear methods for approximating the flow rates.

FIG. 8A shows a noisy slope having a start of inspiration point 201 and a maximum peak 250. A single dashed line 222 between the start of inspiration point 201 and a maximum peak 250 is the approximation for the first order piecewise linear method. The error 221 is the linear distance from the local peak 120 to the line 222. Note that the distance from local peak 130 or from trough 135 was not as great as from local peak 120 so local peak 120 was selected for the error.

FIG. 8B shows the second order, two line, piecewise linear approximation. FIG. 8B has an exaggerated difference from FIG. 8A to help show the principles involved. In FIG. 8B two lines 231 and 232 are selected after comparing all possible pairs of lines for the combination with the least error. Error 223 is the maximum difference between either line 231 or 232 and the raw data. Error 223 is compared to error 221 to see which of the first order or second order linear approximation has the lowest error.

FIG. 8C shows the third order, three line, piecewise linear approximation. FIG. 8C has an exaggerated difference from FIG. 8A and FIG. 8B to help show the principles involved. In FIG. 8C the three lines 231, 232 and 233 are selected after comparing all possible combinations of lines for the combination with the least error. Error 227 is the maximum difference between lines 231, 232, 233 and the raw data. Error 227 is compared to error 221 and 223 to see which of the first order, second order, or third order linear approximations has the lowest error.

The lowest error rate piecewise linear approximation slope is then selected to fill the noisy slope in the array of maximum peaks.

Since methods of fitting first, second and third order piecewise linear approximations to graphs is well understood by those skilled in the art the details of the methods used are not presented here.

As can be readily understood from the above inspiration flow data the same methods are applied to expiration flow data to eliminate noisy slopes.

While breathing the volume of air inhaled must equal the volume of air exhaled. Therefore this is tested for in block 10090 of the algorithm to show the smoothed linear piecewise corrected maximum peak inspiration data match the smoothed linear piecewise corrected minimum peak expiration data. The above tests noisy signals with relatively small amplitude and short duration. However large noise and artifacts have not yet been screened for. Large noises and artifacts can be caused by changes in respiration patterns and presents a difficult problem in breath detection. Typical examples of these changes are the patient changing positions, mouth breathing, severely flow limited breaths, and abnormal breathing after a respiratory period. The following techniques are used to detect unlikely maximum and minimum peaks, which pass the smoothing tests presented so far.

Multiple consecutive breaths are now checked to further disqualify some of maximum peaks and minimum peaks. Maximum peak pairs and trains of maximum peak pairs are used to check multiple consecutive breaths to further disqualify some maximum peaks from the list of candidates for inspiration peaks. For up to 3.5 minutes pairs of successive maximum peaks and sets of maximum peak pairs of maximum peaks are formed and tested by the algorithm in block 10100 for obtaining a train of maximum peaks. The maximum pair and maximum train tests are for testing breaths over a longer period of time. The maximum pairs test covers an entire breathing cycle and the maximum train test covers the maximum peaks correlated to inspiration and expiration over many breaths. Testing over several breaths, usually 2 to 5 breaths, provides a sample of breathing, in which, if the breaths are normal, data about the patient can be used to control a machine.

From an array of maximum peaks such as shown in FIG. 5 the breath periods are checked between any two successive maximum peaks to form maximum pairs such as 250 and 450, or 450 and 650, or 650 and 850.

In the detection of maximum pairs, we obtain three groups of parameters to represent a max-pair. The first group of parameters are related to the duration. The second group of parameters are related to 'shape' of signal, which includes variation of signal level in external duration, and position indexes for different signal levels in internal duration. The third group of parameters are the noise index during the signals in internal duration.

First the maximum peaks are tested to see if the duration of the inspiration is at least 0.75 seconds which is the minimum duration of inspiration for our test purposes.

Second the duration between maximum peaks are tested see if they are less than 10 seconds.

Third the signal level between the max peaks cannot exceed a threshold "T" defined by the following formula:

$$T = \text{the maximum peak of the lower of the two peaks} - (\text{maximum peak of the lower of the two peaks} - \text{minimum peak therebetween})/5.$$

Figure 10:
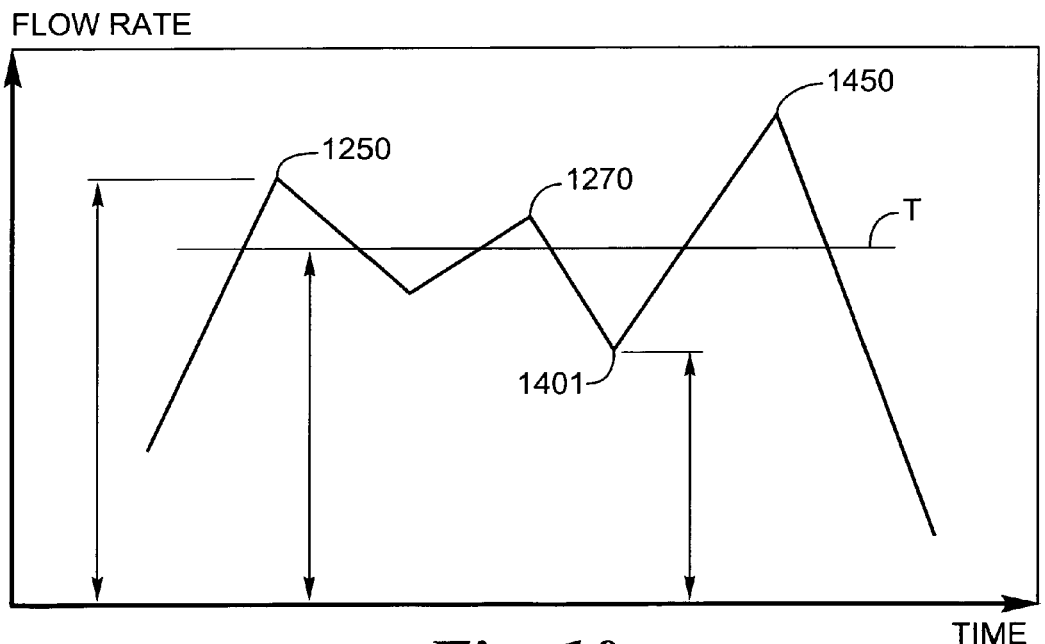
FIG. 10 shows a graph of a threshold for intermediate maximum peaks.

FIG. 10 shows a maximum peak 1250, a maximum peak 1450, a minimum peak 1401 and a threshold T. In FIG. 10 peak 1270 is between peaks 1250 and 1450 and above threshold T therefore the maximum pair of maximum peaks 1250 and 1450 is eliminated as a pair in the maximum train.

Figure 11A:
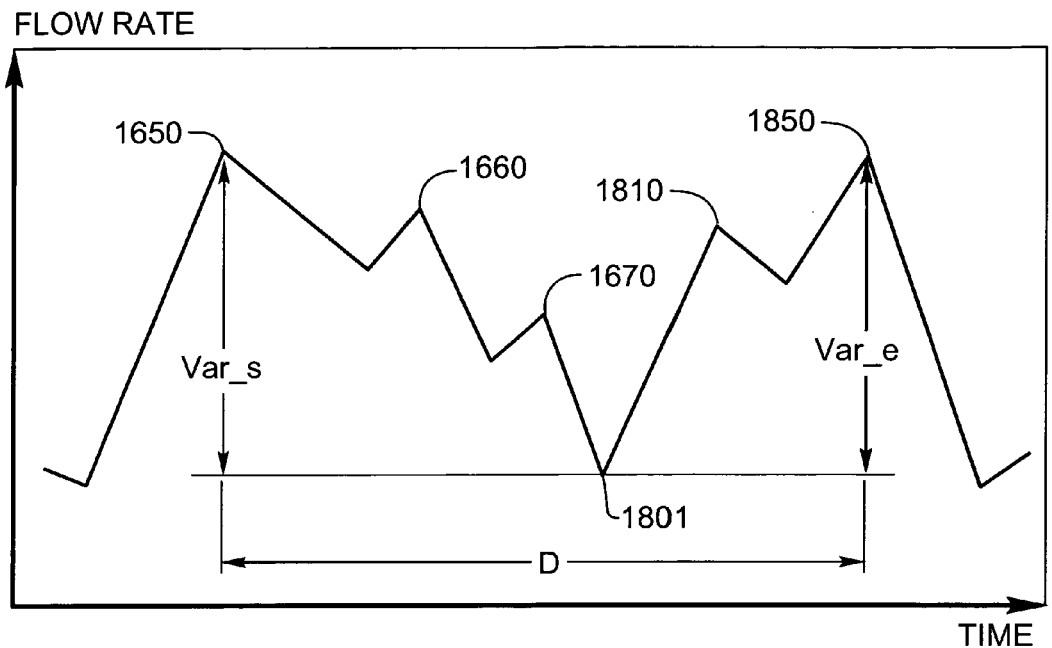
FIG. 11A shows a graph of parameters in a maximum pair of maximum peaks.
Figure 11B:
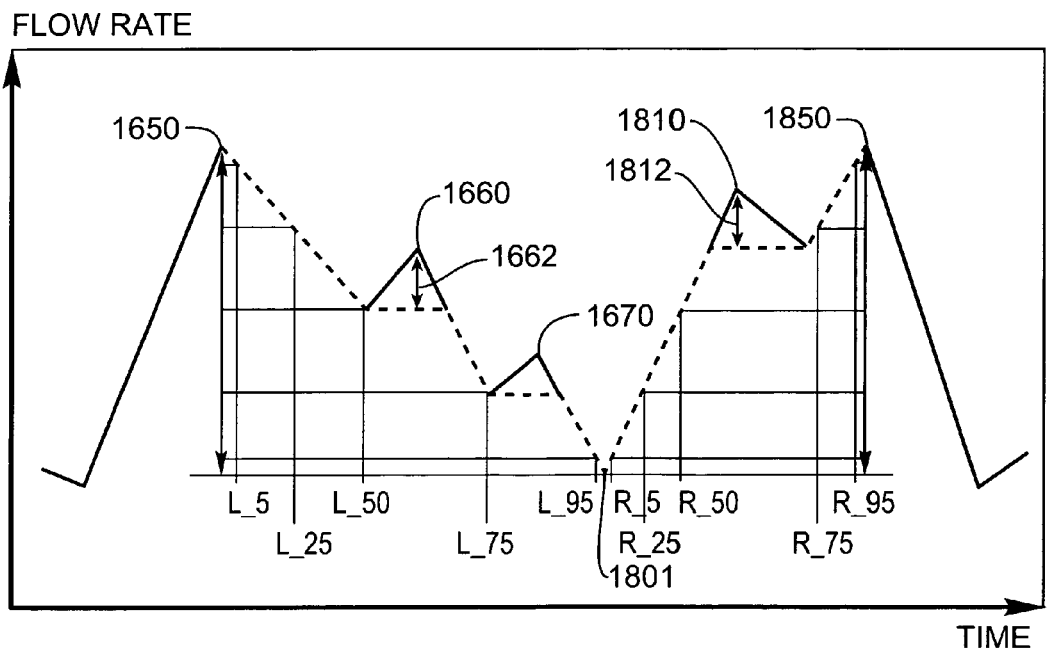
FIG. 11B shows a graph of smoothed parameters from FIG. 11A with percentages of the maximum peak signal levels marked thereon.

For each acceptable maximum pair further tests are performed to define the shape of the maximum pair. As shown in FIG. 11A a maximum pair having a maximum peak 1650 and a second maximum peak 1850 are shown. The duration of the maximum pair is the duration D between the maximum points 1650 and 1850 of inspiration flow rates which has to be between 0.75 seconds and 10 seconds. The variation of the signal level at 1650 is the variation at the start Var_s and the variation of the signal level at 1850 is the variation at the end, Var_e. The variation is measured from the minimum signal value therebetween at 1801. In FIG. 11B the values of the signals are smoothed as dashed line L for decreasing signal values and dashed line R for the increasing signal values. The dashed lines L follow the signal values when they are decreasing and then are graphed horizontally until the values drop further. Similarly the dashed lined R follows the signal values when they are increasing and then are graphed horizontally until the values increase further. Based on the left and right signal values for dashed lines L and R in FIG. 11B the times for signal values of the left or decreasing portion of the inspiration and the right or increasing portion of the inspiration are shown measured at the points L_5, L_25, L_50, L_75 and L_95 representing 5%, 25%, 50%, 75% and 95% respectively of the max peak signal level 1650. The signal values are also recorded at R_5, R_25, R_50, R_75 and R_95 representing 5%, 25%, 50%, 75% and 95% respectively of the maximum peak signal level 1850.

The difference between the actual inspiration flow signals and the approximation lines L and R are determined for the 5%, 25%, 50%, 75% and 95% positions. The average and maximum noise levels are then calculated.

For example the variation 1662 is the difference between the peak 1660 and the 50% of 1650 value on the decreasing signal flow L and variation 1812 is the variation between the peak 1850 and the 50% value of the increasing flow R.

Statistical measurements for the maximum pairs are now used for determining acceptable maximum trains. The first maximum train test is the similarity test run in block 10110 of the algorithm. It tests the similarity between the maximum pairs in the maximum train.

There are seven (7) elements in the similarity test for maximum pairs. Referring to FIG. 11A the elements are duration D, signal variation in external duration, average signal level in internal duration, signal 'shape' in external duration, signal 'shape' in internal duration, average noise level, and maximum noise level. These elements are defined as:

Duration of the max-pair is the time between the beginning maximum peak and end max peak in the max-pair.

Variation of signal level in external duration of the max-pair, denoted as Var, which is defined as the average of variations of starting variation Var_s and the ending variation Var_e, i.e.

$$Var=(Var\_s+Var\_e)/2$$

Average signal level in internal duration, denoted as Aver, which in defined as:

$$Aver=(Value\_s+Value\_e+2*Value\_m)/4+C$$

Where Value_s and Value_e are the maximum peak values at the beginning and the end of the maximum pair, Value_m is the minimum value in between the maximum peaks of the maximum pair, and C is a constant related to setting of data acquisition. C can be ¼ of the dynamic range of the patient flow rate values so as to reduce the impact of small flow values on the average flow value.

Asymmetry measures of the 'shape' of signal in max-pair, denoted as Asy, which is defined as the relative difference in signal variations between the start and the end of the max-pair, i.e., $$Asy=(Var\_e-Var\_s)/(\max(Var\_e, Var\_s)+1)$$

Where Var_s and Var_e are the signal variations between the start and the end of the max-pair, and max (Var_s ,Var_e) is the maximum value, such as at point 1810, between Var_s and Var_e.

The measure of the signal 'shape' of a max-pair. The shape is determined by the left and right 5%, 25%, 50%, 75% and 95% positions of line L and line R as shown is FIG. 11B. The signal shape compares the values at the 5%, 25%, 50%, 75% and 95% positions for indicating the shape of the breaths.

Average noise level, denoted as Noise_aver, is defined as:

$$Noise\_aver=(Noise\_averS/Var\_s+Noise\_averE/Var\_e)/2$$

Where Noise_averS and Noise_averE are the average noise level at the beginning and end of max-pair, Var_s and Var_e are the signal variations between the start and end of the max-pair.

Maximum noise level, denoted as Noise_max, is defined as:

$$Noise\_max=(Noise\_maxS/Var\_s+Noise\_maxE/Var\_e)/2$$

Where Noise_maxS and Noise_averE are the maximum noise level at the beginning and end of maximum pair, Var_s and Var_e are the signal variations between the start and the end of the maximum pair.

For each element of the seven elements, a number of statistical measurements are calculated, which include the mean, the standard deviation, the average and the maximum errors defined as follows:

For a given data set $d_i$, i=1, 2, ..., N, the mean of this data set, Mean_d, is defined as:

$$Mean\_d=(\Sigma d_i)/N, i=1, 2, \ldots, N$$

The standard deviation of this data set, Std_d, has the following equation:

$$Std\_d=((\Sigma d_i)^2/N)^{0.5}, i=1, 2, \ldots, N$$

The average and maximum errors are defined as the average and maximum error between the individual value of the data set and its mean value.

We first calculate seven elements from individual maximum pairs, and obtain four statistical analysis results for each element from all the maximum pairs in the sequence. Finally, we define two indexes for a "similarity" test, namely a mean index and an error index. The mean index is:

$$Mean\ index=duration\ index+asymmetry\ index+noise\ index.$$

The duration index is a measure of how close to the mean duration a sequence of maximum pairs is formed to a 'standard' duration. The duration of a maximum pair is classified into five categories, namely small, small-medium, medium, large-medium, and large durations. If the mean duration is closer to the category of medium duration, a small number is given to the mean index, otherwise a larger number is given to mean index. The asymmetry index is proportional to (Asy-1), i.e., if the 'shape' of a max-pair has more symmetry (Asy~=1), a small value is given to asymmetry index. The noise index is a measure of close the signal level of a max-pair is to a 'standard shape' of signal that is represented by the average and maximum noise level.

The mean index is calculated by initiating the mean index to 1 and adjusted by the following:

The duration categories are as follows:

If the mean duration is excessively small≦2 s the mean index is incremented by 2.

If the mean duration is relatively small between 2 s and 3 s the mean index is incremented by 1.

If the mean duration is relatively large≧7.5 s and <8.5 s the mean index is incremented by 1.

If the mean duration is excessively large≧8.5 s the mean index is incremented by 2.

If the asymmetry is small (mean Asymmetry−1≦0.3) the mean index is incremented by 1.

If mean symmetry is medium (mean Asymmetry−1≦0.5) the mean index is incremented by 2.

Otherwise the mean index is incremented by 3.

If the mean noise is small (mean average noise≦0.16 and mean maximum noise≦0.4) or (mean average noise≦0.2 and mean maximum noise≦0.33) the mean index is incremented by 1.

If the mean noise is medium (mean average noise≦0.33 and mean maximum noise≦0.75) or (mean average noise≦0.4 and mean maximum noise≦0.66) the mean index is incremented by 2.

Otherwise the mean index is incremented by 3.

The resulting mean index is reduced by 3 and restricted by the range of from 1 to 4. Thus the mean index can have the values of 1, 2, 3 or 4 and a smaller value means that the max pair is most likely from a subsequent breath.

The mean index is designed based on a principle of "classification", we have first a "standard" signal shape in mind (medium duration, symmetry, and 'noise-free'), the mean index is then a measure of how close to the 'standard' pattern is each signal pattern from individual maximum pairs. The error index is based on measurement of distribution of sample data (same type of elements) from all maximum pairs in a sequence, if the sample data are close to each other (more similar), the error or standard deviation is small, and the error index will be small as well.

Error sub-indexes are calculated based on the values of average error and maximum error for the parameters of duration, variation, average signal level, asymmetry, left slope shape and right slope shape. The error index is the sum of sub-indexes for average and maximum error from all elements except asymmetry. The closer to each other a type of element from all maximum pairs is within the sequence, the smaller the value in the sub-index, and therefore the smaller the value of error index.

The value of the error sub index depends on a discrete category. Each category is defined as follows:

Average error not more than a threshold and the maximum error being not more than another threshold and the conditions for a previous category do not hold.

The categories are as follows:
(average error and max error thresholds)
Category 1 if (0.12 and 0.33) or (0.18 and 0.24)
Category 2 if (0.18 and 0.48) or (0.27 and 0.36)
Category 3 if (0.25 and 0.75) or (0.37 and 0.50)
Category 4 if (0.32 and 0.96) or (0.48 and 0.64)
Category 5 if (0.40 and 1.20) or (0.60 and 0.80)
Category 6 if (0.50 and 1.50) or (0.75 and 1.00)
Category 7 Otherwise By using a mean index and error index, we carry out a "similarity" test. If a sequence of maximum pairs has passed the test, a maximum train is found. In other words, a maximum train is a collection of the maximum pairs with a similar pattern. The number of maximum pairs in a maximum train is preferably from 3 to 6 maximum pairs. It should be noted that the maximum train is simply an index vector, and each element of the vector is the index of a maximum pair.

As shown in the similarity table in FIG. 37 for every combination of sequence size of max pairs there is a corresponding mean index which has a threshold error index which can not be exceeded for the sequence to be acceptable.

The train of similar breaths shows the patient is breathing in a stable pattern and the breaths can be analyzed for controlling a CPAP machine or other breathing aid.

After the maximum train processing is completed, which has eliminated some maximum pairs from the maximum train, the maximum train is verified in block 10120. During the verification processing it may be necessary to add maximum peak pairs to the maximum peak train that were deleted in the maximum train processing of block 10110.

In the verification at block 10120 we first recall the data from the initial global max-peak and min-peak array generated at block 10110 and compare the closest min-peak array, as the inspiration beginning point in the max peak array should match the expiration ending point of the min peak array and the expiration beginning point in the max peak array should match the inspiration ending point of the min peak array.

Figure 12A:
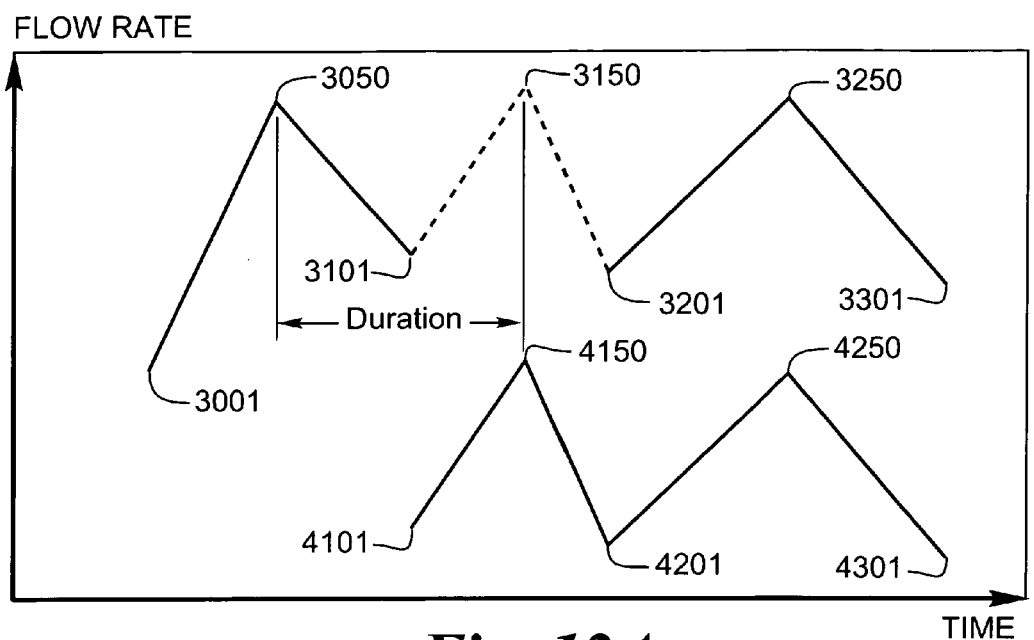
FIG. 12A graph for maximum peak verification.
Figure 12B:
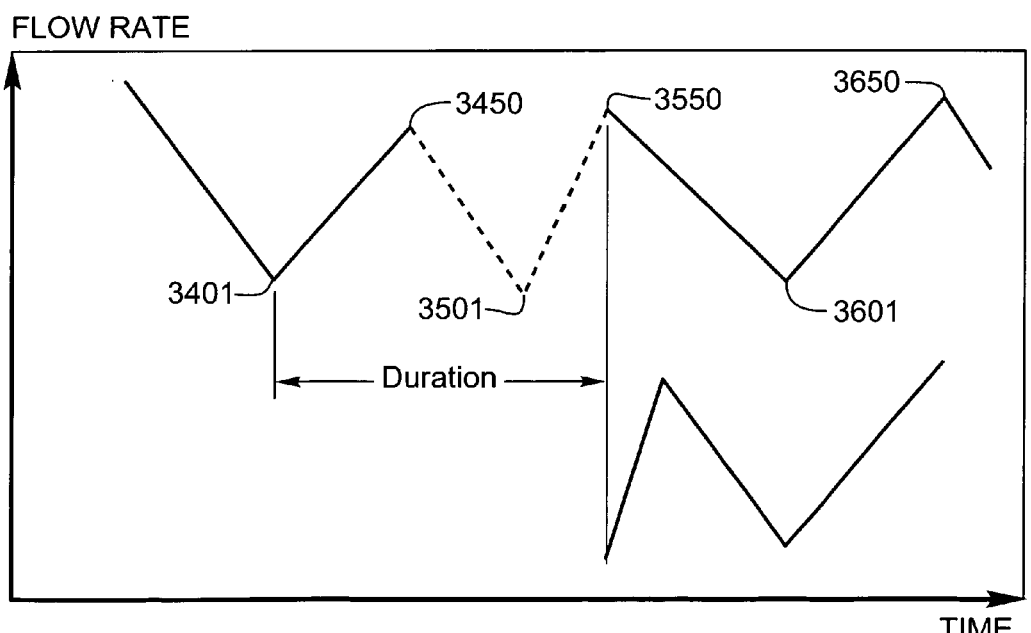
FIG. 12B graph for minimum peak verification.
Figure 13:
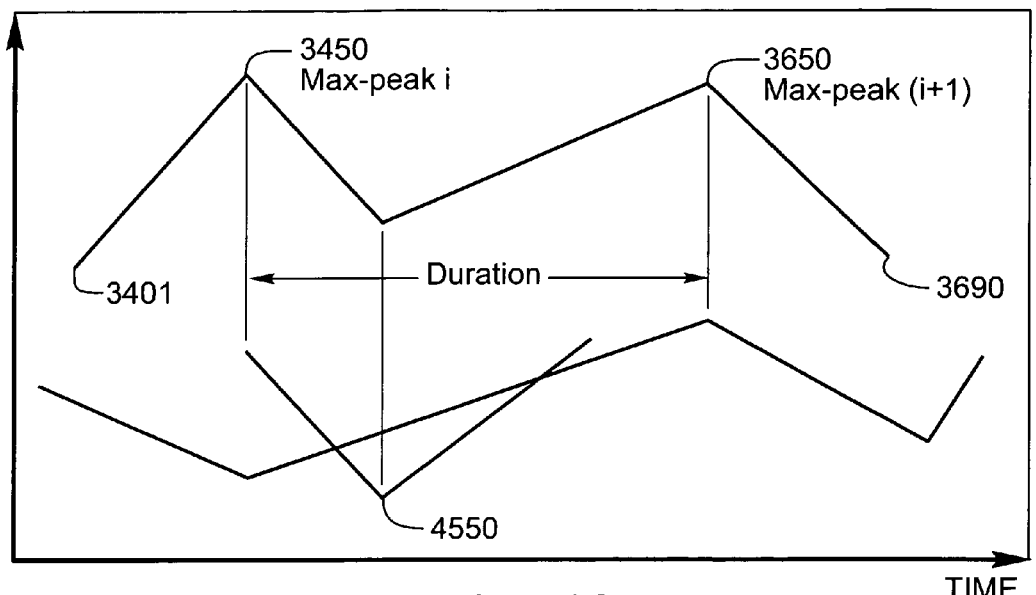
FIG. 13 graph for adding a new minimum peak based on maximum peak based verification.

Therefore, for a given maximum peak 3050 we calculate the duration between the position of the maximum peak 3050 to the closest left position 4150, denoted as left_min, from the minimum peak array as shown in FIG. 12A. If the duration is longer than a pre-defined threshold, it means that we might have deleted a global maximum peak as the result of smoothing processing in the maximum train-processing step in block 10110. Therefore a new max-peak 3150 is added to the initial global maximum peak array, and this 'missed' max-peak should be not 'far' from the closest left position 4101 of the minimum peak. In order to add a new maximum peak, we try to recover the "missed" peak position from the original maximum peak data, i.e., the max-peak_org from block 10030. The peak position is then defined as the maximum peak index which is closest the left positions, i.e., left_min 4101, and the left 3101 and right 3201 positions (indexes) of this added max-peak could be arbitrary as these will be defined later. This processing is called as the maximum peak "left-side" verification. The same method can be applied for the max-peak "right-side" verification, in which we calculate the distance between the position of the maximum peak 3250 to the closest right positions, right_min, 4201, from the minimum peak array. An extra maximum peak could be included if the duration is longer than a predetermined threshold. We also have minimum peak "left-side" and "right-side" verifications as shown in FIG. 12B. Therefore, we have four 'side-base' verifications. After the side based data the algorithm checks for new peaks with "peak-based" data. The peak based check as shown in FIG. 13 examines whether between a pair of any max-peaks such as 3450 and 3650 from the initial global maximum peak array there could have been a minimum peak. If there is no data for a minimum peak, we need to add a new minimum peak 4550, and this new minimum peak index (position) is defined as the position where the signal level is the minimum point inside of this maximum pair, and the left and right positions (indexes) 3401 and 3690 of new maximum pair are also arbitrary. We use the same method to add a new maximum peak based on the 'min-peak-based' verification if necessary.

Figure 14:
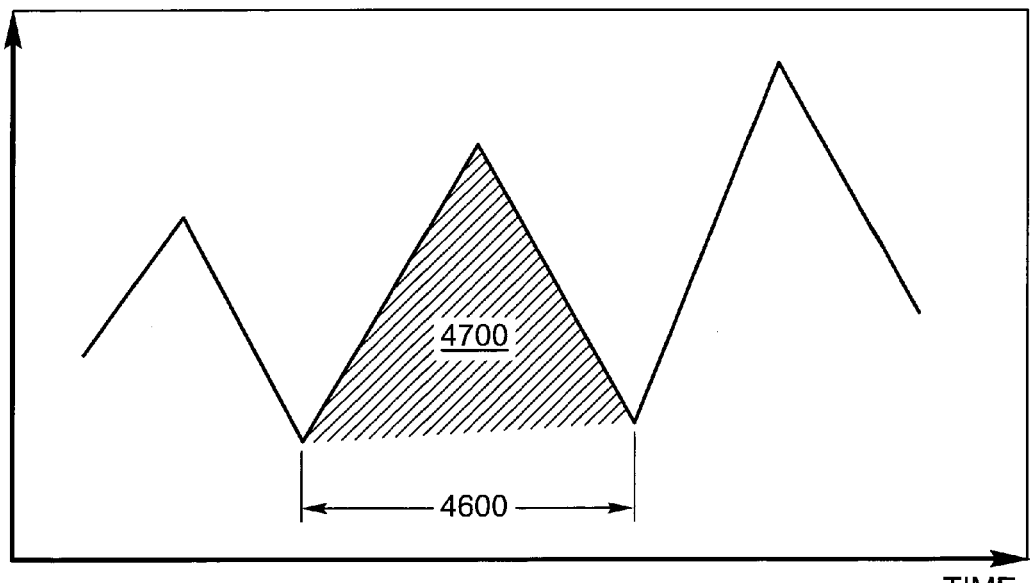
FIG. 14 shows the area and duration between two maximum peaks in a maximum peak pair.

The next test in the verification algorithm is an exclusion process using two measures to further check the maximum peak and minimum peak arrays. The first measure is the signal level verification. If the signal level inside of any maximum pair or minimum pair remains unchanged this maximum pair or minimum pair must be deleted, and the corresponding minimum pair or maximum pair also needs to be excluded from the array. This verification is aimed at removing the maximum peaks or minimum peaks with a constant signal level. This will eliminate conditions where the mask came off or other malfunctions where there is no change in the flow rate signal. The second measure is the duration 4600 between two successive maximum pairs or minimum pairs and the area 4700 which shows the duration and volume of a breath. If two pairs have a duration which is too short the pairs are too "close" to each other. The maximum pair or minimum pair with the smaller signal level amplitude at the peak position should be excluded from the array, as the breath is too short. In order to define an index of the "proximity" between two successive maximum pairs or minimum pairs, we first calculate the duration (Dur) 4600 and area (Area) 4700 of these two maximum pairs as shown in FIG. 14. For given the ith and (i+1)th max-pairs, the Dur(i, i+1) and Area(i,i+1) are examined. We then obtain the relative duration Dur(i,i+1)r, average area Area(i,i+1)ave, and maximum area Area(i,i+1)max as follows:

$$Dur(i,i+1)r = 2*Dur(i,i+1)/(Dur(i-1,i)+Dur(i+1,i+2))$$

$$Area(i,i+1)ave = Area(i,i+1)/(Area(i-1,i)+Area(i+1,i+2))$$

$$Area(i,i+1)max = Area(i,i+1)/\min(Area(i-1,i), Area(i+1,i+2))$$

Where min(Area(i−1,i), Area(i+1,i+2)) is the minimum value of

Area(i−1,i) and Area(i+1,i+2).

The two max-pair are defined as too "close" if the one of the following conditions is met:

Dur(i,i+1)r<=0.5 and Area(i,i+1)max<=0.5 and Area(i,i+1)aver<=0.1     1.

Dur(i,i+1)r<=0.5 and Area(i,i+1)max<=0.33 and Area(i,i+1)aver<=0.125     2.

Dur(i,i+1)r<=0.75 and Area(i,i+1)max<=0.4 and Area(i,i+1)aver<=0.08     3.

Dur(i,i+1)r<=0.75 and Area(i,i+1)max<=0.25 and Area(i,i+1)aver<=0.1     4.

Dur(i,i+1)r<=1 and Area(i,i+1)max<=0.33 and Area(i,i+1)aver<=0.066     5.

Dur(i,i+1)r<=1 and Area(i,i+1)max<=0.2 and Area(i,i+1)aver<=0.08     6.

Figure 15A:
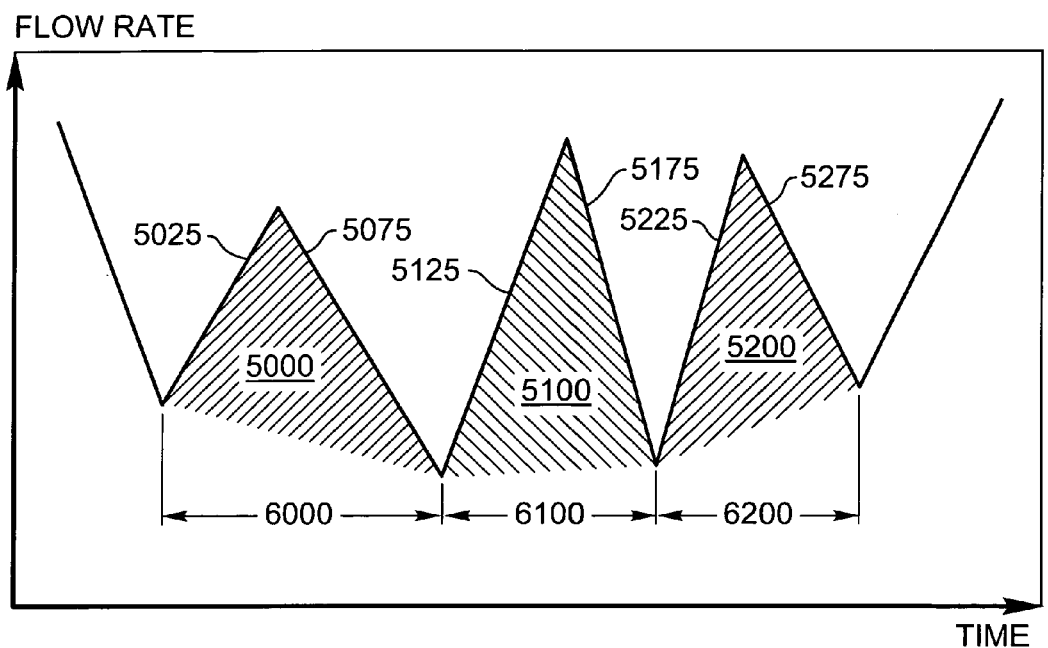
FIG. 15A graphs maximum peaks before the maximum pair excluding process.
Figure 15B:
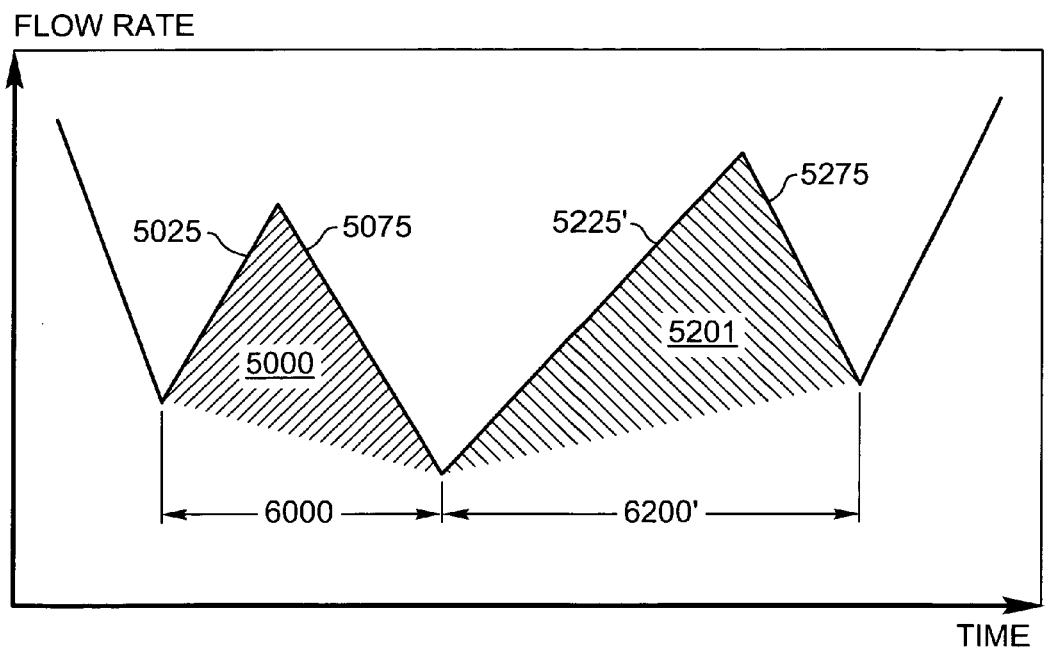
FIG. 15B graphs the maximum pair after the maximum pair excluding process.

If the two max-pair are found to be too "close", the max-pair that has the smaller amplitude of signal level at the peak position is excluded from the array. As shown in FIG. 15A, the (i+1)th max-pair should be deleted, FIG. 15B shows the max-pair array after excluding the (i+1)th max-pair. At the same time, the min-pair associated with the deleted max-pair should be also excluded. The same method can be applied to min-pair check up processing.

As shown in FIG. 15A and FIG. 15B when area 5100 is eliminated, downward slope 5025 remains in place and upward slope 5275' fills in the gap left by the removal of area 5100. The duration 6000 remains the same before and after the elimination of area 5100 whereas duration 6200 increases by duration 6100 to become duration 6200'. The slope and length of upward slope 5225' has changed from slope 5225 while all other slopes remain unchanged.

Figure 16:
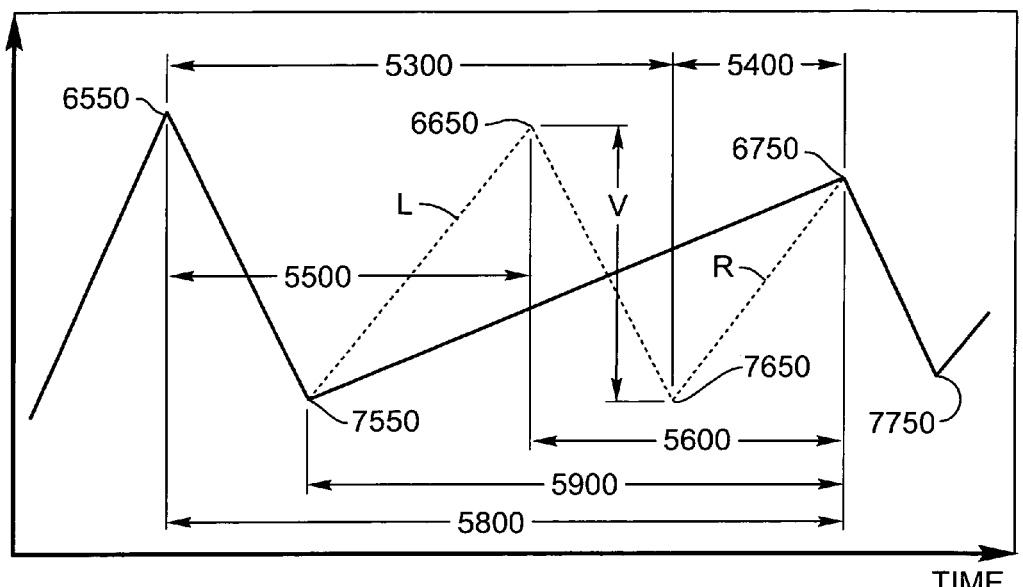
FIG. 16 shows a new maximum and minimum peak being inserted between a maximum peak and minimum peak pair.
Figure 17:
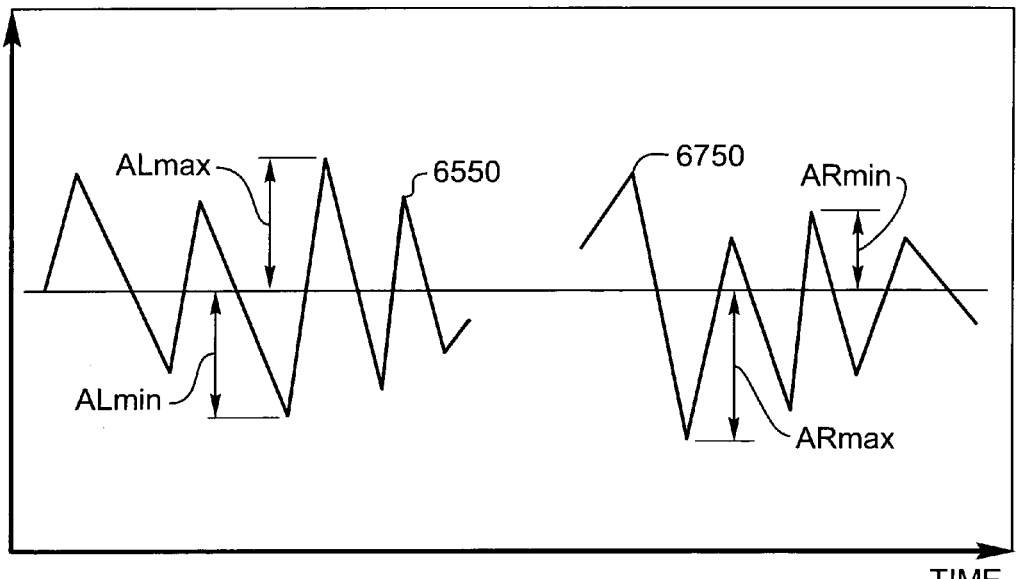
FIG. 17 shows the amplitude thresholds.

The previous verification excluded some maximum pairs and minimum pairs for being too close to one another. The next step in the algorithm checks for pairs of adjacent maximum peaks or minimum peaks to see if they are too far apart. If they are too far apart some real maximum peaks or minimum peaks may have been accidentally deleted. The main criterion used here is the measure of duration between the maximum peaks and the minimum peaks. If this duration is longer than a pre-defined threshold, we look at the original local maximum peak or minimum peak data to see if any peaks were qualified as an additional global maximum peak or minimum peak. There are two types of "long-distance" measurements to be used in this verification, the "4-second" verification, and the "10-second" verification. In the "4-second" verification, the algorithm steps are:

1 Calculate the duration between any peak position in each max-pair and the peak position from the closest min-pair.
2 If the duration is longer than $T_d$=4 seconds, a new max-peak and new min-peak are searched from the original local max-peak and min-peak sets. The possible candidate must meet three conditions, namely position, signal amplitude, and smoothing. FIG. 16 shows a new pair of max-peak and min-peak inserted between peak positions 6550 and 6750. Three conditions are defined as:
a. Position condition: The minimum duration 5500 or 5600 from maximum peak 6550 or maximum peak 6750 respectively to the new maximum peak 6650 must not be shorter than 1 second. Similarly the minimum duration 5300 or 5400 from maximum peak 6550 or maximum peak 6750 respectively to the new minimum peak 7650 must not be shorter than 1 second. Further, the new max-peak 6650 should be located half way between the maximum peak 6550 and maximum peak 6750 while the new minimum peak 7650 should be located half way between minimum peak 7550 and minimum peak 7750.
b. Amplitude condition: The amplitudes of new maximum peak 6650 and minimum peak 7650 must be larger than a threshold $A_p$ that depends on the amplitudes of neighbouring max-peak and min-peaks as shown in FIG. 17. Where $Ap=Amin+0.75*Avar$ Amin=minimum values of ALmin and ARmin Avar=average of (ALmax+ARmax) minus the average of (ALmin+ARmin)

The reference character L represents the left hand or prior in time data and R represents the later in time data to the newly inserted maximum or minimum peaks.

The parameters of ALmax and ALmin are calculated from a number of pairs (up to 4 pairs is suggested) before peak position of 6550, and ARmax and ARmin are calculated from a number of pairs (up to 4 pairs as well) after peak position of 6750.

c. Smoothing condition: The added maximum peak 6650 and minimum peak 7650 in FIG. 16 is considered to be relatively smoothed, and which is tested by comparing the noise levels of Line L and R with the signal variation inside of these two peaks (as shown in FIG. 16 as internal variation V. To calculate the noise level in Line L and R we first define a "monotonous line" for Line L and Line R as shown in FIG. 16. Then we calculate the difference between the Line L or Line R and the actual flow signal data level at a few points such as the 5, 25, 50, 75, and 95 percentage points to the maximum point. Finally, we define the average and maximum noise levels. If the average noise is less than 12.5% of internal variation V and the maximum noise level less than 50% of value of V, then the new maximum peak and minimum peak pass the smoothing condition test.

If all three conditions (a, b and c) are satisfied, a new pair of max-peak and min-peak are inserted between peak position 6550 and 6750.

The algorithm then tests for the long duration or the 10 second verification. The duration threshold is defined as 10 second, i.e., if the duration between any peak position in each maximum pair and the peak position from the closest minimum pair are greater than 10 seconds, then a new pair of maximum peak and minimum peaks must be added. There are also three measurements for possible candidates for the newly added maximum peaks and minimum peaks, namely duration ratio, signal level ratio, and noise ratio.

a. Duration ratio: For any under-tested pair of maximum peak and minimum peak pairs, we first calculate the average duration between all pairs of successive maximum peaks and minimum peaks after the under-tested pair of the maximum peak and minimum peak. Then, we define a measure of ration of duration Dur_ratio as:

$Dur\_ratio=Dur/Dur\_aver$ if $Dur\_aver>Dur$ otherwise $Dur\_ratio=Dur\_aver/Dur$ b. Signal level ratio: Starting from the point of the under-tested pair of max-peak and min-peak, we obtain the minimum and maximum point form all pairs of max-peaks and min-peaks, denoted as S_min and S_max. The signal level ratio S_ratio is defined as:

$$S\_ratio = S\_diff/(S\_max - S\_min)$$

Where S_diff is the different signal levels between the under-tested maximum peak and minimum peak.

c. Noise ratio: the noise level inside of the under-tested pair of maximum peaks and minimum peaks, and the similar 'five-point' measure at 5%, 25%, 50% 75% and 95% of the flow rate values is used to find the average noise level, N_aver. The noise ratio N_ratio is then defined as:

$$N\_ratio = N\_aver/S\_diff$$

Unlike in the previous method, we define a measure Comb_ratio that is the combination of three ratios to test the pair of maximum peak and minimum peak. The Comb_ratio is defined as:

$$Comb\_ratio = S\_ratio * Dur\_ratio * (1 - N\_ratio)$$

The pair of maximum peaks and minimum peaks with the largest value of the Comb_ratio is added as a new pair in the globe maximum peak or minimum peak array. The measure of the Comb_ratio can be interrupted as a "similarity test", which means that the closer a pair of maximum peaks and minimum peaks is to other pairs, the more likely the pair can be added into the global maximum peak and minimum peak array.

The last step of global smoothing processing is to update the global maximum peak and minimum peak arrays. As a result, we can find the following information from the updated global max-peak and min-peak arrays.

Each max-peak is followed by a min-peak.

Each max-peak is associated with a possible inspiration period, and the following min-peak is likely to indicate an expiration period.

The algorithm then uses the above adjusted global flow data to determine the inspiration intervals in block 10130.

Figure 18:
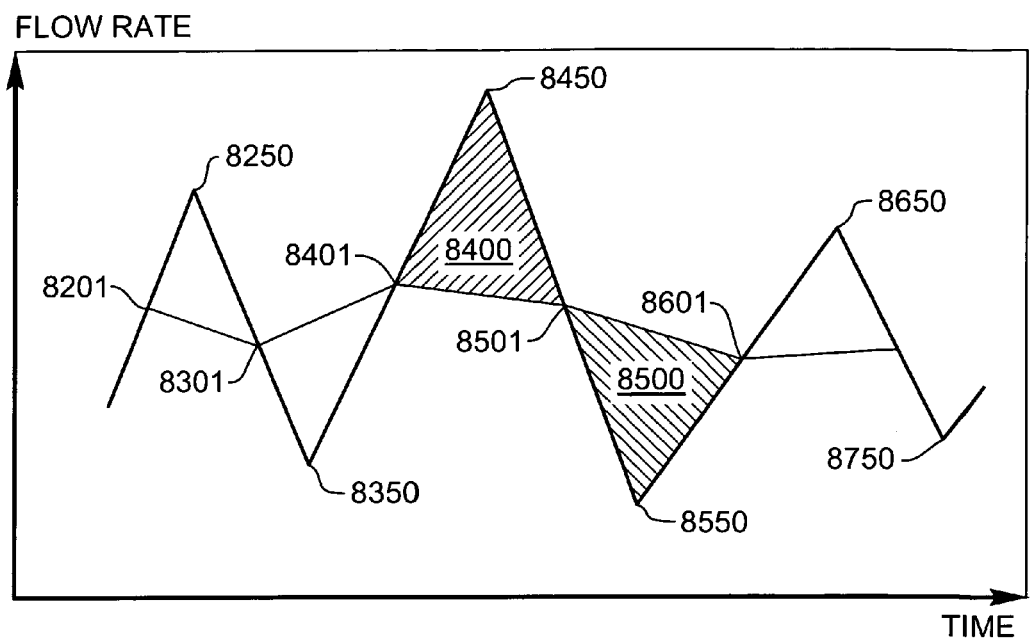
FIG. 18 is a graph of inspiration and expiration flow areas.

The estimated breath inspiration and expiration beginning and end points are the break points where the inflows and outflows of breath occur. At these break points the flow data start to significantly increase. When the inspiration data and the expiration data are joined in one graph, as shown in FIG. 18, the inspiration flow peaks 8250, 8450 and 8650 are shown as well as the expiration flow peaks 8350, 8550 and 8650. The break points are where the flow changes from zero to significantly increase or decrease for inspiration at points 8201 8401 and 8601 and for expiration at points 8301, 8501 and 8701. The graphs show inspiration area 8400 and expiration area 8500. The start of the inspiration period is the end of the expiration period.

To estimate the inspiration intervals the maximum peaks and minimum peaks are identified. The index points associated with the maximum peaks are preferably selected from the 250 hertz original data measurements rather than the 10 hertz adjusted global data from the adjusted data above. This will shift the points at which the maximum and minimum flows occur. The 10 hertz data was used to cut computation time by using fewer data points. Once the peaks are established the break points are selected and the area of the inspirations and expirations are calculated. The inspiration area should be about equal to the expiration area. The break points for inspiration and expiration should have about equal values. FIG. 18 shows the break points 8201, 8301, 8401, 8501, 8601 and 8701. The maximum peaks are 8250, 8450 and 8650. The minimum peaks are 8350, 8550 and 8750. The inspiration areas 8400 and expiration areas 8500 are shown in FIG. 18 as triangular areas. The triangle corners are 8401, 8450 and 8501 for inspiration area 8400 and 8501, 8550 and 8501 for expiration area 8500. 8501 should be the same value or nearly the same value for the inspiration break point and the expiration break point.

Figure 19:
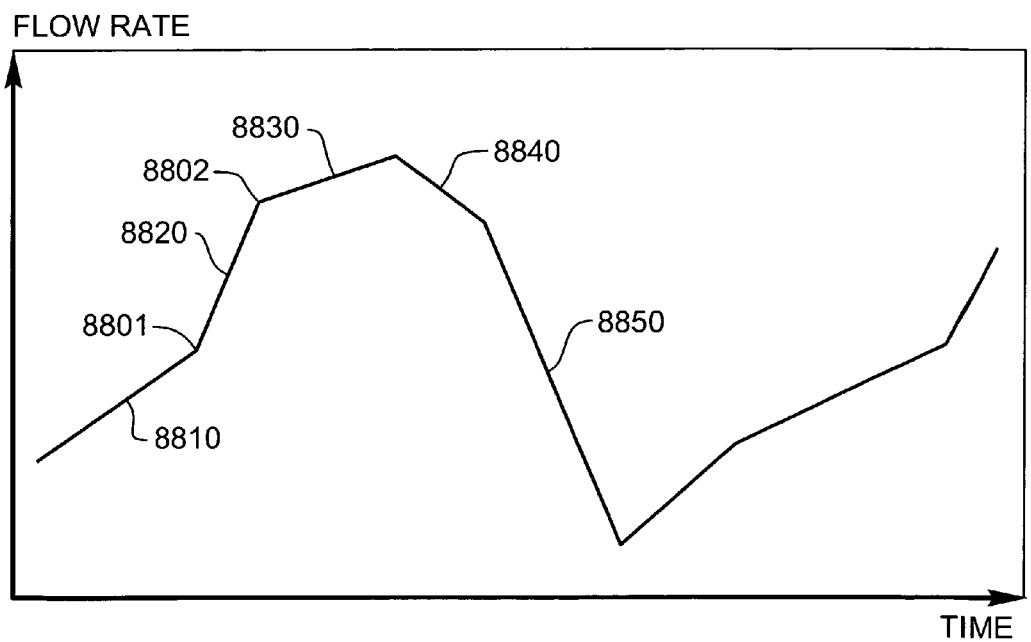
FIG. 19 is a graph of a noise free shaped breath pattern.

The above approximation of inspiration and expiration break points of block 10130 are now fine tuned in block 10140 to determine a closer approximation to the inspiration and expiration points by examining the data in greater detail as shown in FIG. 19 which more closely approximates the shape of a real breath.

When the airflow is measured at the mask the amounts of flow during the inspiration period and the expiration period may not be the same, especially when patients use their mouth to breath, this is known as a "flow imbalance". Further the data collected suffer from an "area insensitivity" problem. This occurs because when patients start inspiration the flow signal level rapidly increases, but the measurement of flow area is an integration process and is much slower than the change of flow signals themselves. In other words, the change of flow area is not sensitive enough to accurately measure the start point of inspiration where the flow signal is changing rapidly. Although the problems of "flow imbalance" and "area insensitivity" affects the accuracy of detection of inspiration interval, a simple and inexpensive computation of calculating the flow area provides a good method for estimating inspiration intervals with reasonable accuracy. With the estimated results, further fine-tuning of the start point of inspiration based on detecting the change of flow signal patterns is performed. From the signal measurement point of view, a start-point of an inspiration period can be defined as the point where the flow signal starts to "significantly" increase. This definition of start point of an inspiration is reasonably robust. A third-order linear approximation method is employed to detect the start point of inspiration. By using a third order piecewise linear approximation method three slopes will more closely approximate the inspiration and expiration rather than a single slope to further define the shape of the breath.

FIG. 19 shows a first slope line 8810 a second slope line 8820 and a third slope line 8830 on the increasing slope of the inspiration and two more sloped lines 8840 and 8850 approximating the decreasing slope of the inspiration.

Figure 20A:
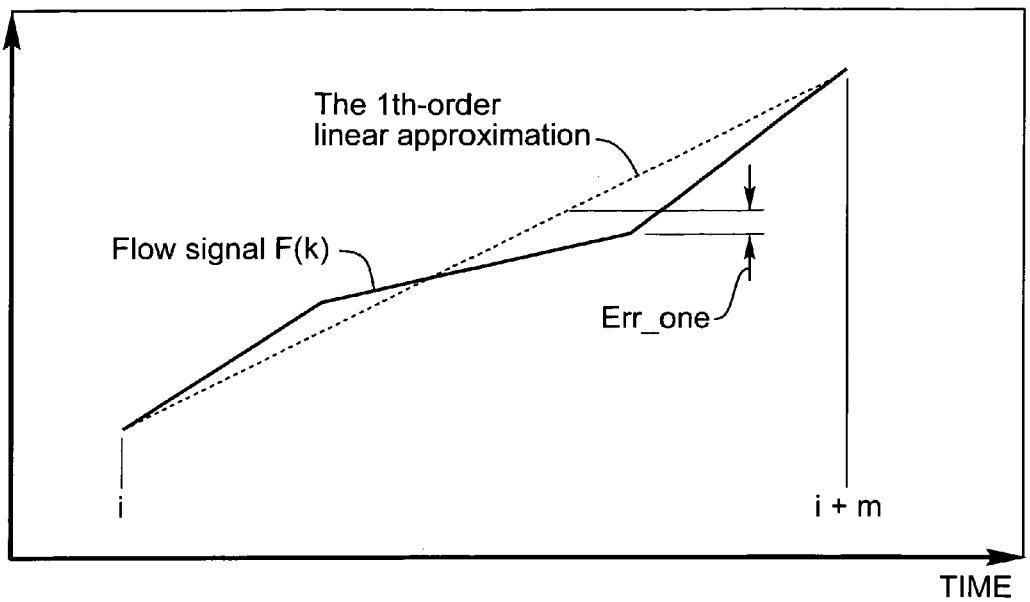
FIG. 20A shows a first order linear approximation of an inspiration.

The first second and third order equations are calculated as follows:

1. The first order linear approximation is shown in FIG. 20A.

For a given flow signal $F(k)$, $k=i, i+1, \ldots, i+m$, as shown in the first order linear approximation method defines a linear equation $F'(k)$ as $$F'(k) = a + b*(k-i),$$

Where, constant $a = F(i)$, and slope $b = (F(i+m) - F(i))/m$.

The different between the $F(k)$ and $F'(k)$ can be calculated as $$Diff(k) = |F(k) - F'(k)| = |F(k) - a - b*(k-i)|$$

The error of the approximation in this study is defined as $$Err\_one = \max(Diff(k))$$

Where, max $(Diff(k))$ is the maximum value of $Diff(k)$.

The first order approximation is then shown in FIG. 20A by the dashed line.

Figure 20B:
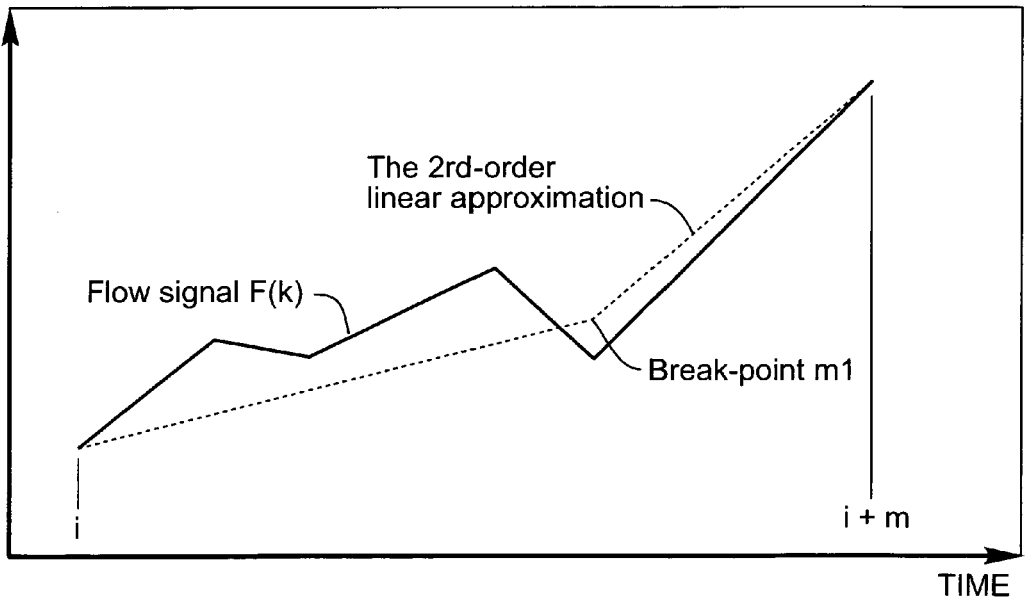
FIG. 20B shows a second order linear approximation of an inspiration.
Figure 20C:
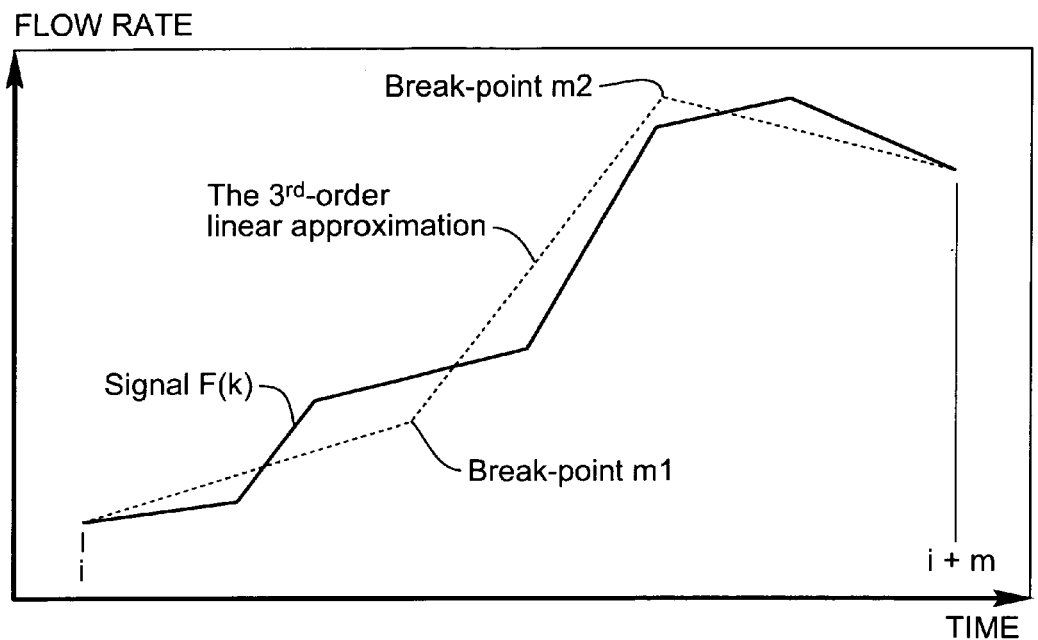
FIG. 20C shows a third order linear approximation of an inspiration.

2. The second order linear approximation is shown in FIG. 20B.

For a given flow signal $F(k)$, $k=i, i+1, \ldots, i+m$, the second order linear approximation method is to define a piecewise linear equation $F'(k)$ as $F'(k)=a1+b1*(k-i), k=i, i+1, \ldots, m1$ for the first slope and $F'(k)=a2+b2*(k-m-1), k=m1+1, m1+2, \ldots, i+m$ for the second slope.

Where, two constants a1 and a2 are defined as $a1=F(i),$ $a2=F(m1+1)$

Two slopes, b1 and b2, are calculated by $b1=(F(m1)-F(i))/(m1-i)$ $b2=(F(i+m)-F(m1+1))/(I+m-m1-1)$ The different between signal F(k) and the F'(k) is obtained by $Diff(k)=|F(k)-F'(k)|=|F(k)-a1-b1*(k-i)|, k=i,i+1,\ldots, m1$ for the first slope $Diff(k)=|F(k)-F'(k)|=|F(k)-a2-b2*(k-m1-1)|, k=m1+1, m1+2, \ldots, i+m$ for the second slope.

The approximation error is then defined as $Err\_two=\max(Diff(k))$

The approximation error Err_two is a function of m1, and m1 is a so-called the break-point (as shown in FIG. 20B). A search processing is used to find this break-point. Starting from m1=i+1, an approximation error Err_two (i+1) is obtained. While the m1 increased from i+2, i+3, . . . , i+m−1, we have a set of approximation errors Err_two(i+2), Err_two (i+3), . . . , Err_two(i+m−1). The break-point m1=j is defined if the error Err_two (j) is the minimum value of the error set. As we can see from the FIG. 20A, at the break-point m1 the flow signal appears to be changing (increasing) significantly.

3. The Third order linear approximation.

In the third order linear approximation, we need to define two break-points m1 and m2 based the minimum approximation error as shown in FIG. G-1-1c. For a give signal F(k), k=i, i+1, . . . , i+m, the third order linear approximation can be represented as:

$F'(k)=a1+b1*(k-i), k=i, i+1, \ldots, m1$ for the first slope.

$F'(k)=a2+b2*(k-m1-1), k=m1+1, m+2, \ldots, m2$ for the second slope $F'(k)=a3+b3*(k-m2-1), k=m2+1, m2+2, \ldots i+m$ for the third slope And the difference between F(k) and K'(k) is $|F(k)-F'(k)|=|F(k)-a1-b1*(k-i)|k=i,i+1,\ldots,m1$ $|F(k)-F'(k)|=|F(k)-a2-b2*(k-m1-1)|k=m1+1,m1+2,\ldots,m2$ $|F(k)-F'(k)|=|F(k)-a3-b3*(k-m2-1)|k=m2+1, m2+2, \ldots i+m$ Where, the constants a1, a2, and a3 are defined as $A1=F(i), a2=F(m1),$ and $a3=F(m2).$ The three slopes are calculated as follows:

$b1=(F(m1)-F(i))/(m1-i)$ $b2=(F(m2)-F(m1+1))/(m-2m1-1)$ $b3=(F(i+m)-F(m2+1))/(i+m-m2-1)$

The approximation error is then $Err\_three=\max(|F(k)F'(k)|)$

A similar search method is used as in the second order linear approximation to determine the value of the m1 and m2. That is that we change the values of m1 and m2, and obtain a set of approximation errors Err_three. Then the break-points m1 and m2 are chosen when the Err_three reaches the minimum.

The break point can now be more accurately determined which will be used to more accurately pinpoint the beginning of inspiration.

The single slope inspiration graphs of FIG. 5 do not show a realistic breath shape. Inspiration flow rate changes are not constant. FIG. 19 shows a more realistic inspiration flow breath shape. For the purpose of detecting start of inspiration, we can focus on the period between the flow signal between the minimum value to the maximum value. During this period, the typical flow change pattern has three 'phases' according to the flow speed, for the FIG. 19 case, which has the pattern such as slow change, fast change, and slow change again. In this pattern, there are two break points 8801 and 8802 which indicate the speed of flow change, the first break-point 8801 is where the flow signal appears to be increasing significantly is defined as the start of point of inspiration. It should be noted that there are many breath patterns, but in most circumstances three piecewise lines are accurate enough to approximate the increased-phase of inspiration for the purpose of detecting the start point. The three pieces-wise linear third-order linear approximation method is used to approximate 'optimally' the flow signal located in the increased-phase of inspiration. The results of the third-order linear approximation processing include two break-point positions 8801 and 8802 and three slope values, S1, S2, and S3 for slopes 8810, 8820 and 8830 respectively. The break points 8801 and 8802 are the main candidates for the start of inspiration. The criterion of detecting the start point is then simply a comparison of the relative changes of flow signal level at the break points 8801 and 8802. When testing if break point 8802 is a start point, we first calculate four parameters; two of them are variations of signal level, and two duration. These parameters are defined as follows:

$Var\_ref=F\_B2-F\_min$ $Var\_B2=F\_max-F\_B2$ $Dur\_ref=B2-P\_min$ $Dur\_B2=P\_max-B2$ If one of the following conditions is met, then 8802 is defined as the start of inspiration.

| | |
|---|---|
| Var_B2>=1.5*Var_ref and Dur_B2<0.5*Dur_ref | 1. |
| Var_B2>=2*Var_ref and Dur_B2<0.6*Dur_ref | 2. |
| Var_B2>=2.5*Var_ref and Dur_B2<0.75*Dur_ref | 3. |
| Var_B2>=3*Var_ref and Dur_B2<Dur_ref | 4. |
| Var_B2>=3.5*Var_ref and Dur_B2<1.2*Dur_ref | 5. |
| Var_B2>=4*Var_ref and Dur_B2<1.5*Dur_ref | 6. |
| Var_B2>=4.5*Var_ref and Dur_B2<2*Dur_ref | 7. |
| Var_B2>=5*Var_ref and Dur_B2<3*Dur_ref | 8. |
| Var_B2>=7*Var_ref and Dur_B2<4*Dur_ref | 9. |

Var_B2>=9*Var_ref and Dur_B2<5*Dur_ref     10.

Var_B2>=12*Var_ref and Dur_B2<6*Dur_ref     11.

For testing break point 8801, we also calculate four parameters in a similar way, i.e., $Var\_ref = F\_max - F\_B1$ $Var\_B1 = F\_B1 - F\_min$ $Dur\_ref = P\_max - B1$ $Dur\_B1 = B1 - P\_min$ Break-point 8801 is detected as the start of inspiration if the one of the eleven (11) conditions is met, the only change of conditions for testing for break point 8801 compared to break point 8802 is to replace Var_B2(Dur_B2) by Var_B1 (Dur_B1).

The break-point 8801 could also be defined as the start point of inspiration using the same eleven (11) conditions but we need to re-calculate four (4) parameters as follows:

$Var\_ref = F\_B2 - F\_B1$ $Var\_B1 = F\_B1 - F\_min$ $Dur\_ref = B2 - B1$ $Dur\_B1 = B1 - P\_min$ After detecting the start point of the inspiration, we then search end point of the inspiration in the decreasing flow signal segment. The end point of the inspiration is detected where the signal level is the same as the signal level at the start point of the inspiration.

This fine-tuning processing is carried out to fine-tune all estimated start and end points of each inspiration. We then have an inspiration interval array that includes the all indices for the start and end positions for each inspiration.

The end of the inspiration is taken as the point having the same value of the inspiration on the decreasing slope.

The beginning and ending points of the inspiration and expiration of each breath are now calculated and can be used to control a SPAP machines. The flow rates of each breath are also known and can be used in the control of SPAP machines.

Figure 21A:
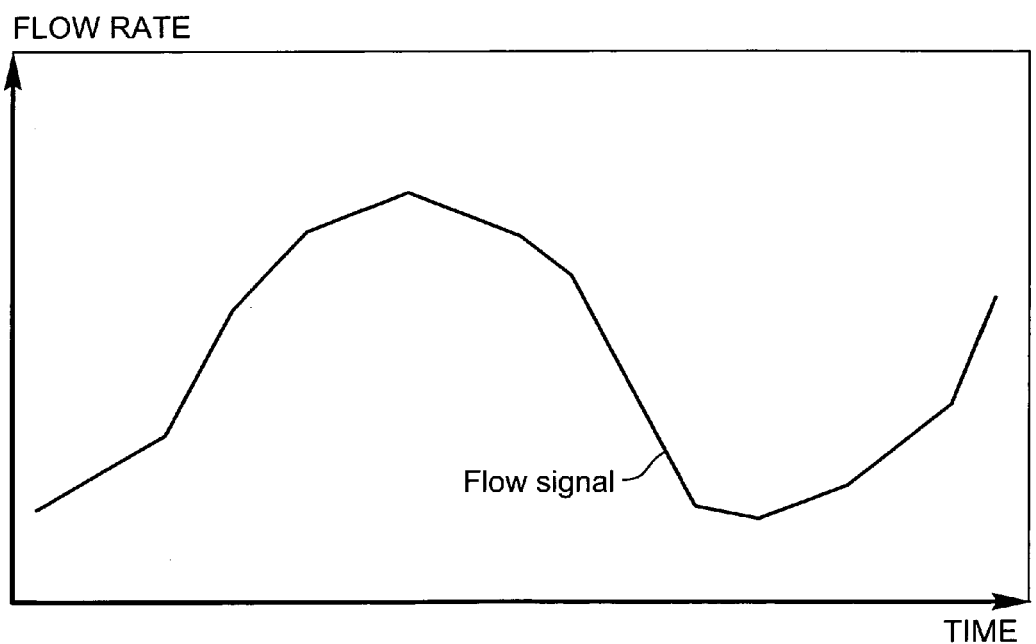
FIG. 21A shows the profile of a normal breath.
Figure 21B:
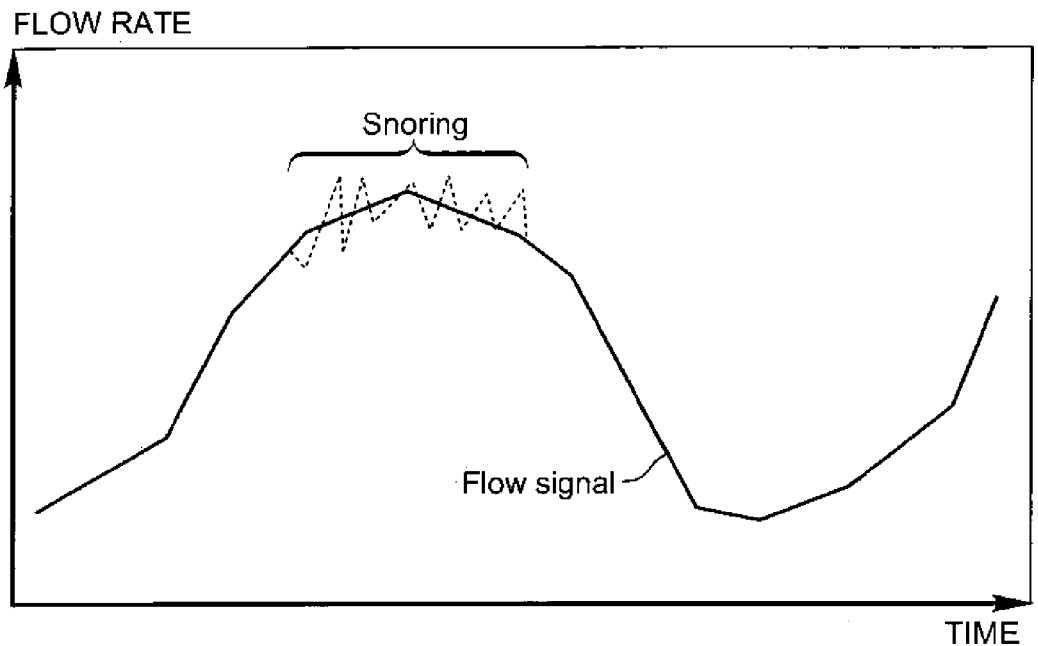
FIG. 21B shows the profile of snoring during a breath.
Figure 21C:
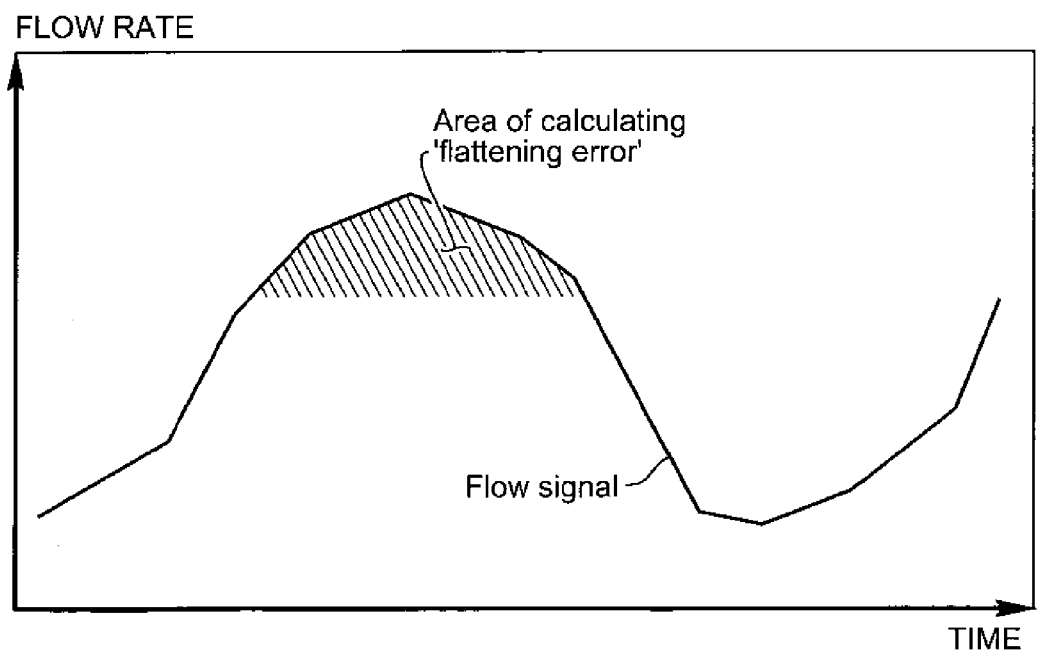
FIG. 21C shows the profile of an inspiration flow limitation.
Figure 21D:
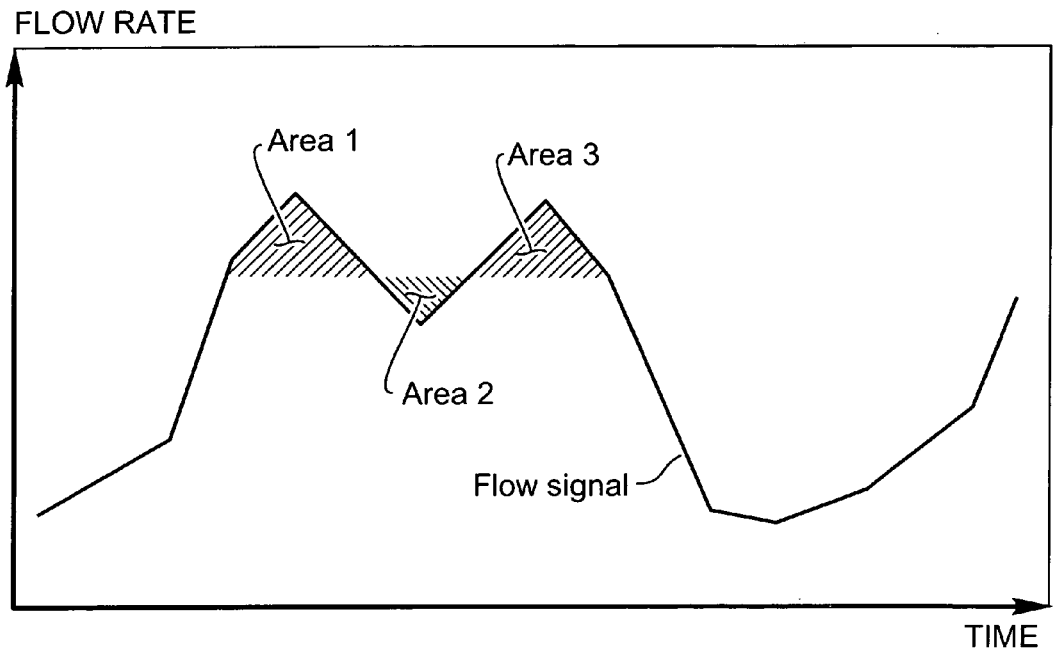
FIG. 21D shows the profile of a severe inspiration flow limitation.

With the data collected the SPAP machine needs to detect three types of respiratory events, namely apneas and hypopneas, snoring, and inspiration flow limitation. The first type of events (apneas and hypopneas) is associated with reduction of inspiration flow, which is detected directly from the breath flow rate data collected. Both snoring and inspiration flow limitation are more likely to occur during "abnormal" breath periods. For a "normal" breath, the "shape" of signal on the top of inspiration flow appears "rounded" and relatively smooth as shown in FIG. 21A. When snoring is present the high frequency flow signal is visible during inspiration as shown in FIG. 21B. Inspiration flow limitations are defined as events when the patient is unable to generate continuous flow increase during the first half of an inspiration period. As a result, the flow signal on the peak of inspiration flow becomes 'flat' as shown in FIG. 21C. In flattening analysis, carried out in block 10150 we determine a reference "flat" line using a best fit method of the flow signal at the top of inspiration graph according the least square error (LSE) method, and the difference between the flow signal and the reference "flat" line during this period is calculated as a flattening error as shown in FIG. 21C. The flattening error with the smallest value is defined as a flattening index. The flattening index is then used to measure the flow limitation. The smaller the flattening index, the more severe is the inspiration flow limitation. In the case of FIG. 21D, the flow limitation is more severe than that in the FIG. 21C. Therefore the signal data in area 1 and 2 are the only data used to calculate the flattening error so that a smaller flattening error and flattening index can be obtained. A snoring index has been developed to indicate the degree of the snoring. The snoring index is defined as measurement of the amount of high frequency signal on the top of inspiration flow.

The flattening index measures the inspiration flow limitation. There are two steps in the flattening index analysis. First a reference 'flat' signal level is determined. The reference 'flat' signal level approximates the inspiration flow. It is found by using the least square error (LSE) method. Then the flattening index is calculated. The flattening index is found by calculating the error of the flow signal relative to this reference 'flat' level.

Figure 22A:
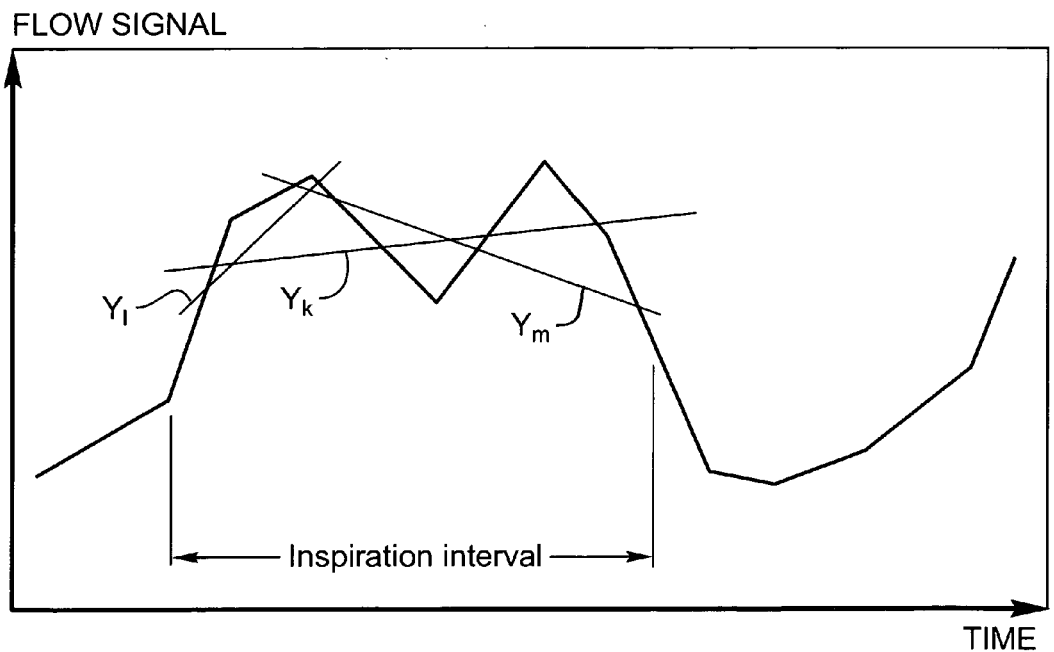
FIG. 22A graphs the flattening index candidate reference lines during horizontal searching.
Figure 22B:
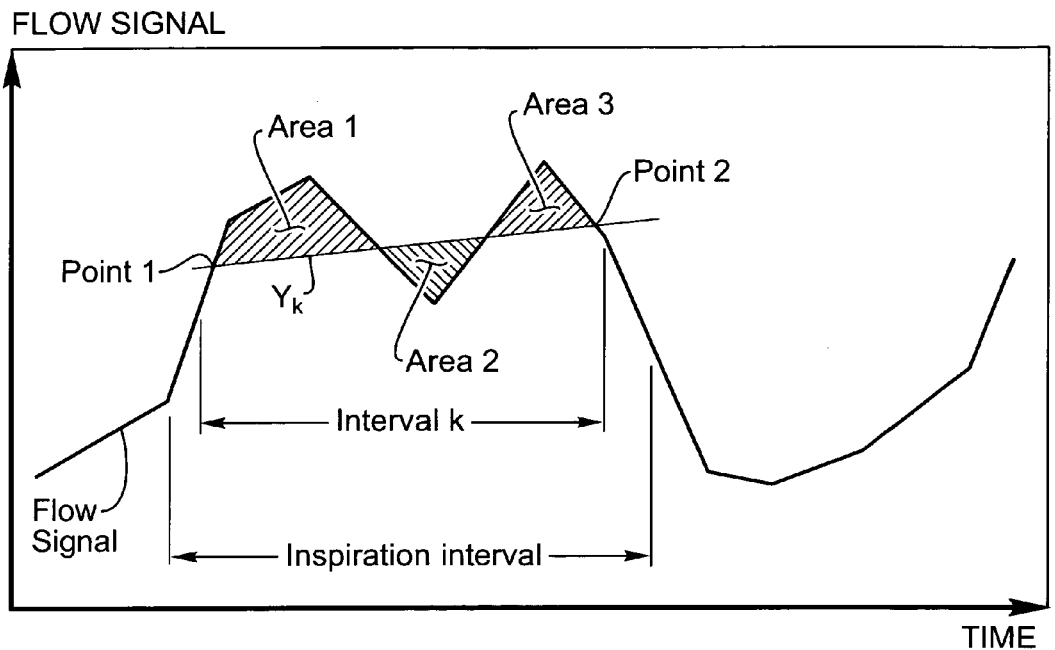
FIG. 22B graphs the chosen flattening index.

1. The reference 'flat' signal level:

A reference 'flat' signal level for a given inspiration flow is defined as a straight line with a length of 60 percentage of inspiration interval. The straight-line slope can be flat, increasing, or decreasing. In addition the 'flat' signal level for each inspiration period must be a straight line best fitted to the flow signal within the given interval (60% of total inspiration period) based on the least square error method. A 'two-dimension' (2-D) searching method is used to find a reference flat signal level, which includes horizontal (Time) and vertical (Flow) searching. The 2-D searching method is as follows:

In horizontal searching processing, as shown in FIGS. 22A and 22B, for a given flow signal F within an inspiration interval (between Ins_start Ins_end) the length of the straight line is defined as 0.6*(Ins_end−Ins_start). Starting from the point of Ins_start+0.05*(Ins_end−Ins_start), we find a straight line that fits the signal flow with LSE. This processing continues in every 10 ms until the end point of the 'flat' line is equal or less than the point of Ins_end−0.05*(Ins_end−Ins_start). Horizontal searching results in a set of straight lines $Y_i$ as shown in FIG. 22A with the following equation:

$Y_i = A_i + B_i X_i$

Where, i=1,2,..., m, m=0.4*(Ins_end−Ins_start)/10 is the number of straight lines in the set, $X_i$ is the time (flow signal) index, $A_i$ and $B_i$ are the parameters of the of straight lines, which are defined as:

$A_i = (\Sigma F(X_j) - B_i \Sigma X_j)/L$ $B_i = (L * \Sigma(F(X_j) * X_j) - (\Sigma F(X_j)) * (\Sigma X_j))/D$ Where, $L = 0.6 * (Ins\_end - Ins\_start)$ $D = (L * (\Sigma(X_i) - (\Sigma X_i)^2),$ Using the change of time index, we have a set of reference 'flat' lines $Y_i$ as shown in FIG. 22A, i=1,... k...,m. The line k is the best candidate as the reference 'flat' line for calculating the flattening error and index as it is the flattest and is replotted in FIG. 22B. However, according to the definitions for the flattening error and index, there are three problems here. Number one, the signal before point 1 and signal after point 2 in FIG. 22B should not be used to calculate flattening error and index. Number two, the difference between the signal in area 2 and line $Y_k$ needs to be excluded from the calculation. Number three, after excluding these portions of like k the signal no longer has the calculated LSE for the remaining signal.

Figure 23A:
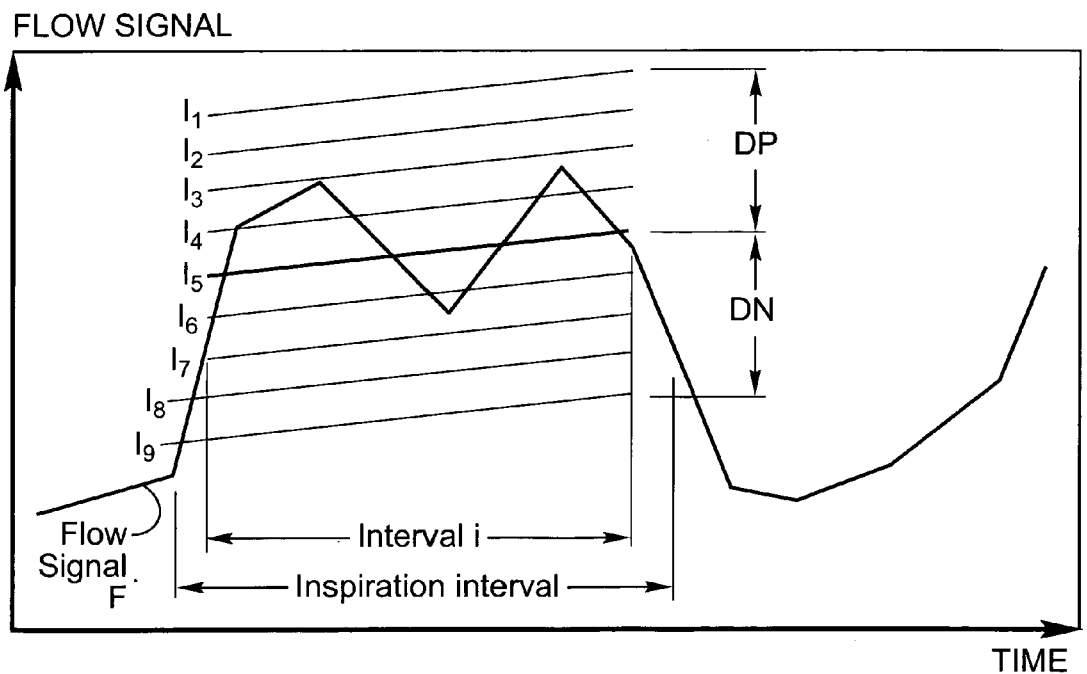
FIG. 23A is a graph of up and down flattening indexes.

The first problem can be solved by detecting the crossing-point from the start and end point of the interval k, points 1 and 2 in the FIG. 22B, and only using the signal between these two crossing points to calculate the error and index. The second and third problems are solved by adjusting the reference 'flat' line set based on the vertical searching process. For a given reference 'flat' line I resulting from the horizontal searching we calculate the difference between the flow signal F and the 'flat' line over the interval i as shown in FIG. 23A. The maximum and minimum deflections are denoted as DP and DN. Keeping the slope of the line I the same, we increase both the start and end points of the line I by DP/4, DP/2, 3*/DP/4, and DP to form four lines $I_1$, to $I_4$ which are parallel to the line $I_5$. In the similar way we decrease both the start and end points of the line I by DP/4, DP/2, 3*/DP/4, and DP to form another four parallel line $I_6$ to $I_9$. As a result, we obtain a group of nine (9) parallel lines from line $I_1$ to $I_9$, and based on these nine (9) parallel lines we further calculate the flattening error and index.

There are four phases in the calculation of flattening error. For a given time index I, we have a set of nine (9) parallel lines, namely $I_1$ to $I_9$. For a given line (i,j) from the set of Line-I, j=1,2, . . . 9, we find the crossing-point from the start of the interval i as point 1, and the second crossing-point from the end of the interval i as point 2, both point 1 and 2 are shown in the FIG. 23B. Starting from the crossing point 1, we calculate the average difference between the flow signal and the line (i,j) until the signal reaches the crossing point 2, but excluding the signal at the area 2 where the flow signal is below the line (i,j). The average difference is denoted as E' (i,j_start_end), which indicates how 'close' the inspiration flow is to the reference 'flat' line, i.e., the line (i,j). In the flattening analysis, we need to know not only the inspiration flow 'closeness' to a straight line, but also how 'flat' this straight line is. It is useful to measure the average flow signal during the inspiration period. In order to measure this 'flattening', we calculate a weighted flattening error E (i,j_start_end), which is defined as:

$$E(i,j\_start\_end) = F\_mean1 * E'(i,j\_start\_end) + F\_mean2 * D\_f$$

Where:
F_mean1 and F_mean2 are related to the average flow signal during the inspiration period, which are defined as:

$$F\_mean1 = C1/F\_mean$$

$$F\_mean2 = C2/F\_mean$$

F_mean is the average flow signal during the inspiration period, and its range varies from 150 to 30, C1=1000, and C2=60 is limited to D_f is the difference between the flow signal at the end and start of the interval i.

Figure 23B:
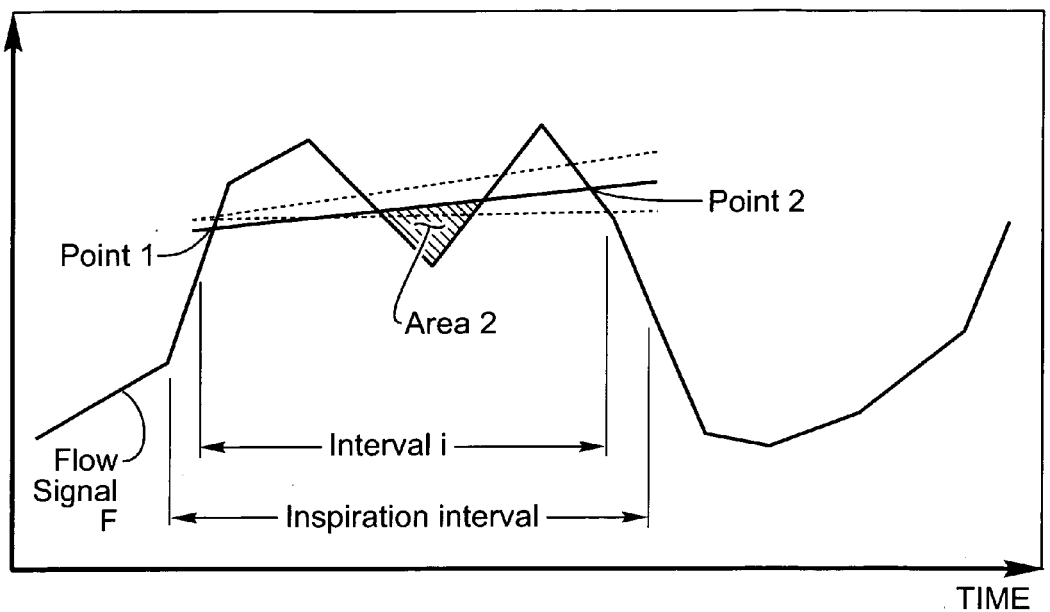
FIG. 23B is a graph of left side flattening indexes.
Figure 23C:
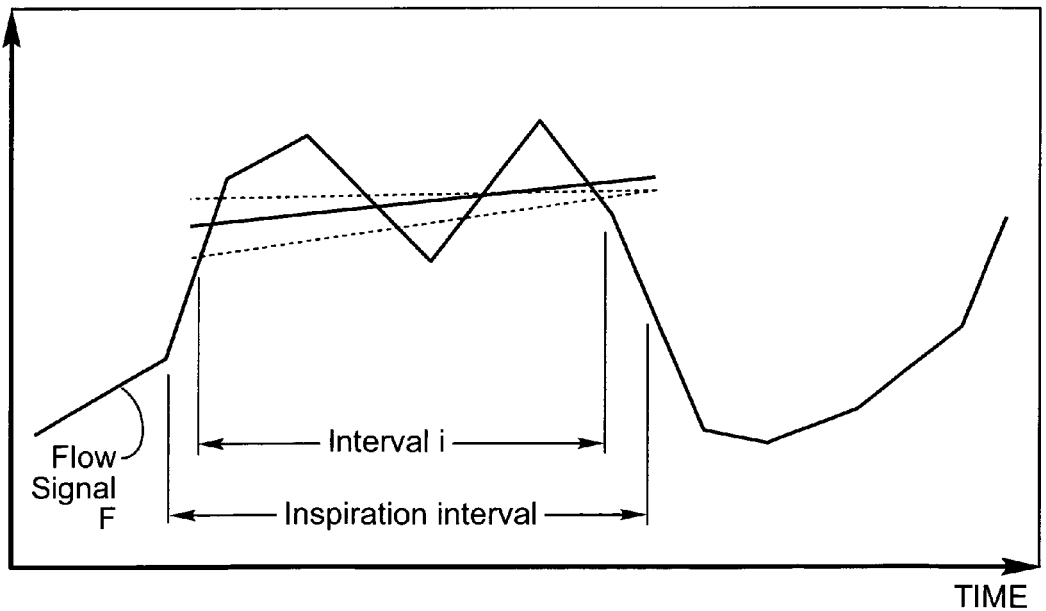
FIG. 23 C is a graph of right side flattening indexes.

Therefore, the weighted flattening error E (i,j_start_end) is then proportional to the absolute value of the slope of the reference line (i,j). This processing is the first phase of calculation of error. We then fix the start point of the line (i,j), and increase the end of the line (i,j) by DP/4 as shown in FIG. 23B, and the phase I is carried out again to obtain error E(i, j_end_+). By decreasing DN/4 to the end point of the line (i,j), we have error E(j_end_−). As shown in FIG. 23C, we also fixed the end point of the line (i,j), and change the start point of the line (i,j) to obtain errors E(j_start_+) and E(j_start_−). Among of these five errors, we define the smallest error as E (i,j), and this processing is the second phase of the calculation flattening error. In the third phase, we repeat the phase 1 and 2 to calculate a set of nine (9) errors, E(i,j), for each line (i,j) from the set of Line-I, j=1,2 . . . 9. The minimum value of E (i,j) is then defined as E (i) which represents the flattening error at the time index i. As the find phase, the time index i changed from 1 to m, i.e., the m sets of reference 'flat' lines are calculated and adjusted to obtain a set of m error, E (i), i=1,2, . . . m. The minimum value of error among of them is then defined as the flattening error for this inspiration period, denoted as E. This weighted flattening error is then used as the flattening index in this study, denoted as F_index.

Figure 22C:
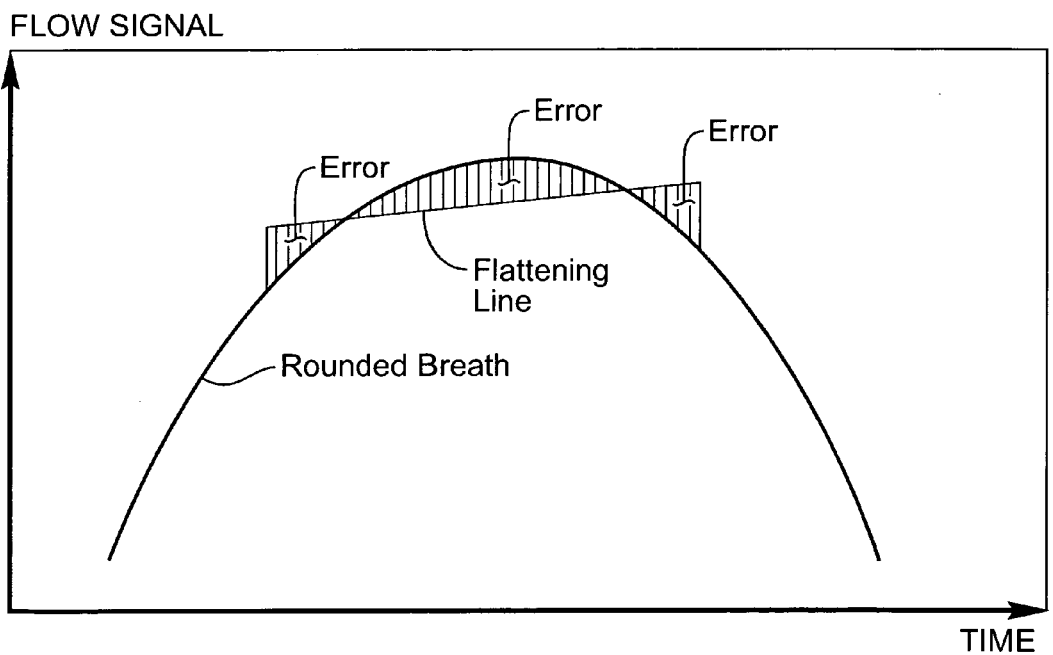
FIG. 22C graphs the flattening index error on a rounded breath.
Figure 22D:
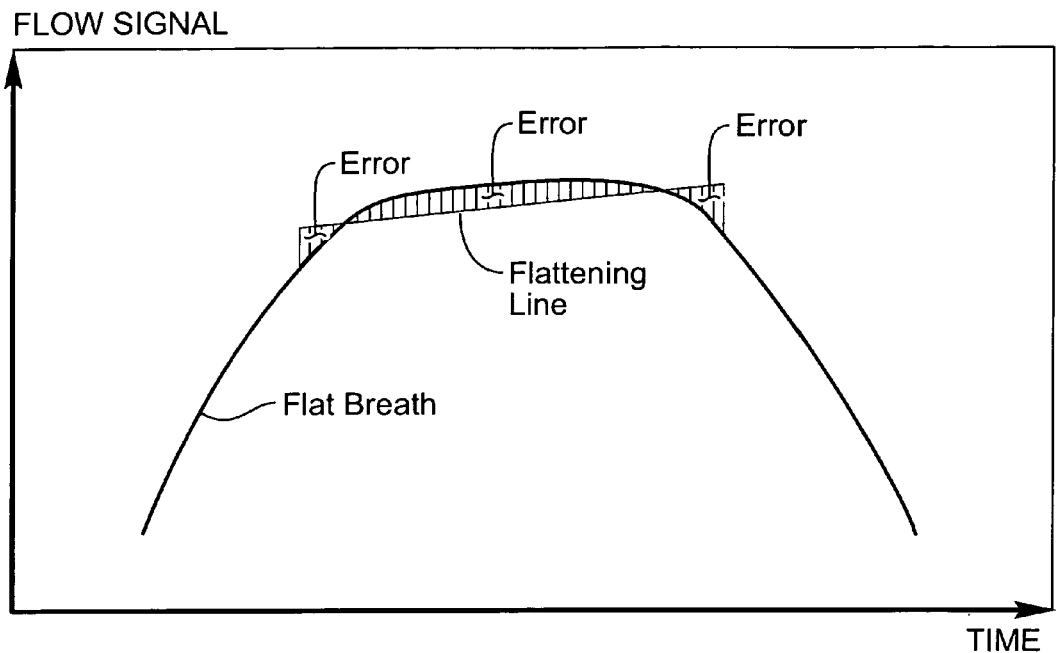
FIG. 22D graphs the flattening index error on a flat breath.
Figure 22E:
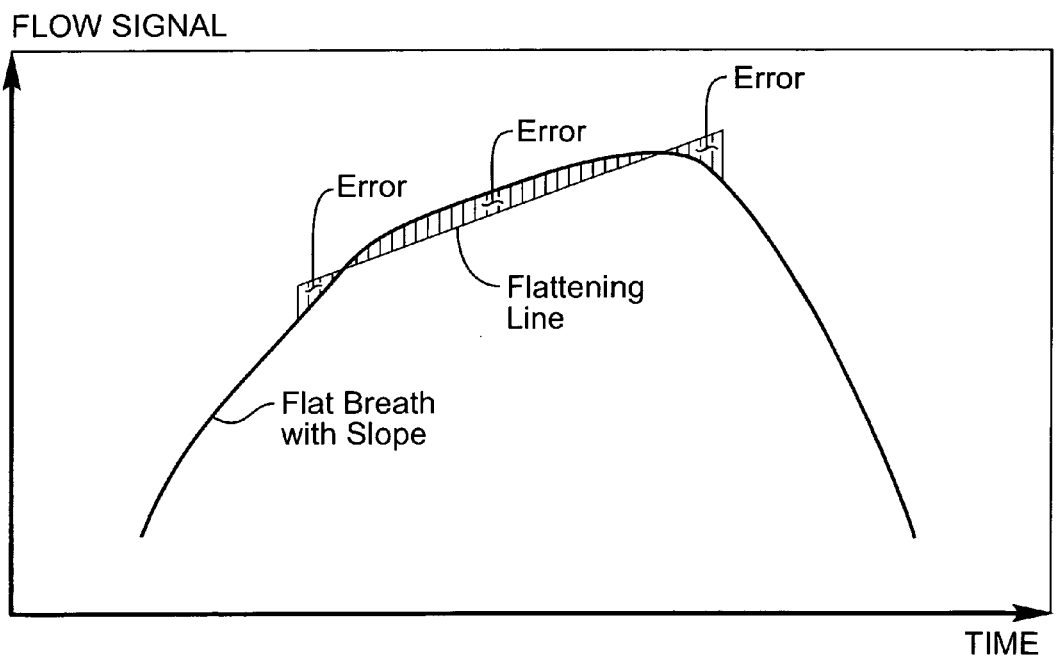
FIG. 22E graphs the flattening index error on a sloped flat breath.
Figure 22F:
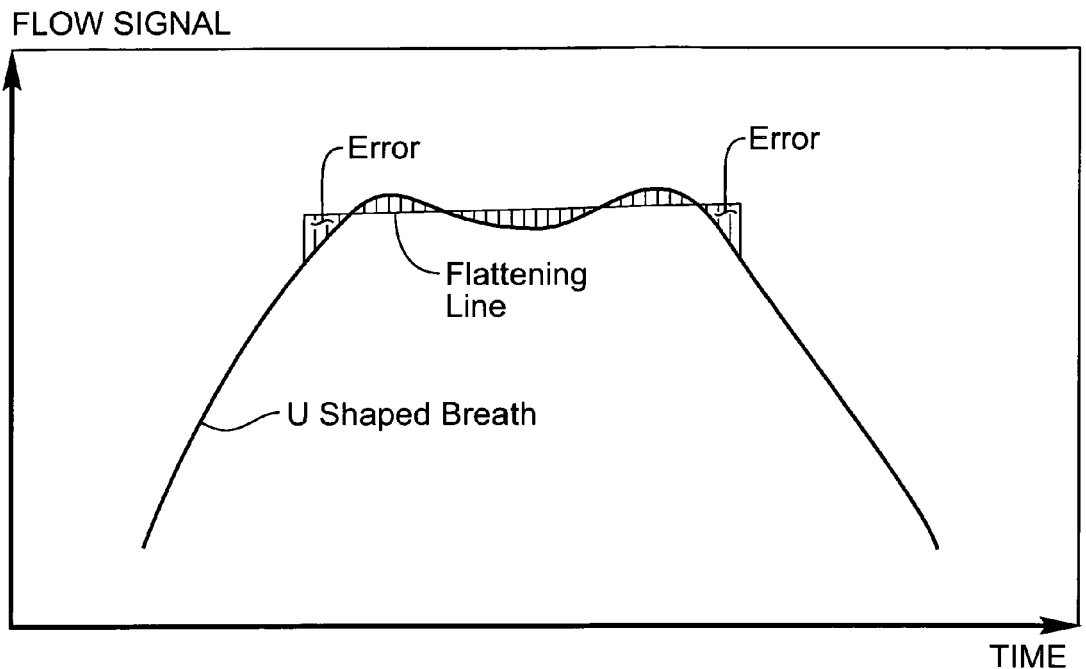
FIG. 22F graphs the flattening index error on a U shaped breath.

The LSE errors are shown for different breath shapes in FIGS. 22C-22F. In FIG. 22C a rounded breath with errors in three areas are shown. FIG. 22D shows a flat breath with on error area. FIG. 22E shows a sloped flat breath with a sloped breath error area. FIG. 22F shows a U shaped breath with a two error areas. The middle error area is not counted below the line to reflect the fact that U shaped breaths represent a larger increase in upper airway resistance than flat breaths. The flattening line would be fairly accurate if the flow signals were noise free, but patient flow signals are not only determined by upper airway resistance but also by snoring and noise due to dynamic leak and flow turbulence. Since these factors distort the underlying inspiratory flow and the LSE approximations a randomized testing method is used to improve the robustness of the LSE flattening index. The testing involves using multiple tests with the original straight line being slightly modified and then choosing the least error as the best fit.

With the flattening index calculated the degree of blockage of the patient's airway can be determined for an aid in diagnosing apnea and hypopnea events. Flow amplitude data is used to identify apnea and hypopnea event.

The snoring index is now determined in block 10160 of the algorithm. From the flow signal processing point of view, a snoring signal is defined as a 'high frequency noise' in the peak of inspiration flow signal, and the snoring index is a measure of the 'degree' of snoring. Therefore, the detection of a snoring index can be considered as a measurement of the amount of 'noise' signal in terms of amplitude and frequency, the more noise in the peak flow signal, the larger snoring index, and more severe in the event of snoring. In this study, we use the following steps to calculate the snoring index.

Figure 24:
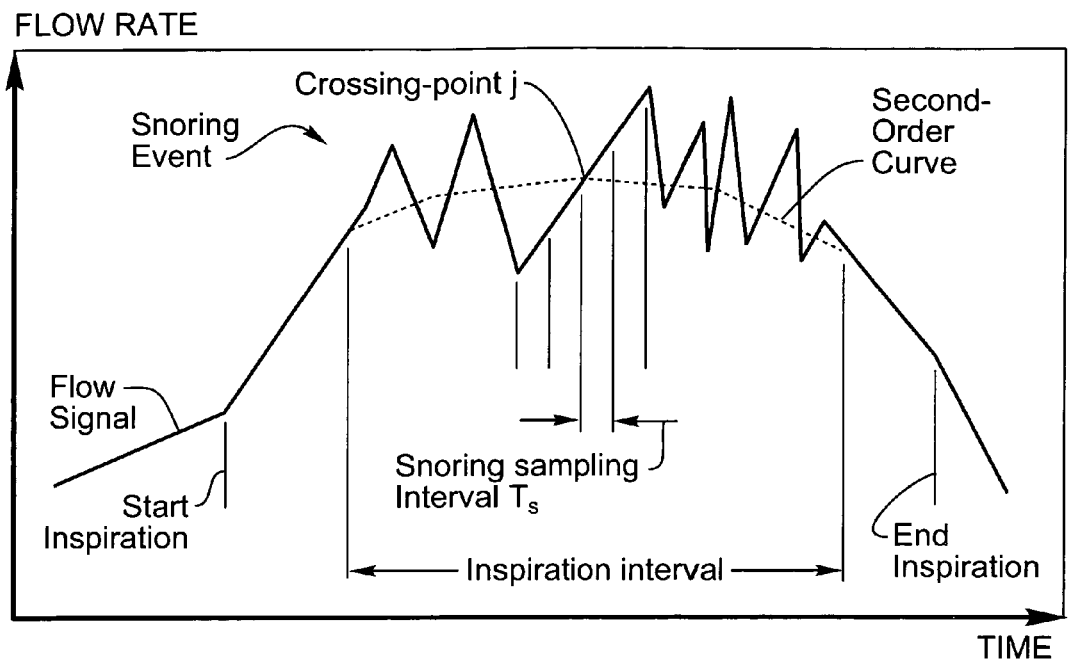
FIG. 24 is a graph of the snoring index.

Step 1: For a given inspiration period from the time index Ins_start to Ins_end, we define the half duration of the inspiration interval as the snoring test duration (Ds) which is located on the middle of the inspiration duration, as shown in FIG. 24. The flow signal in the snoring test duration (Ds) is approximated using a second-order curve-fitting technique, and the second-curve $Y_s$ is the bold line as shown in the FIG. F-1. The second-order curve $Y_s$ has the expression:

$$Y_s = Coef_0 + Coef_1 * (i - Ins\_start) + Coef_2 * (i - Ins\_start)^2$$

Where i is the time index, i=Ins_start+1, . . . , Ins_end, and coefficients $Coef_0$, $Coef_1$, and $Coef_2$ are defined as:

$$Coef_2 = ((\Delta X_2 Y) * \Delta X_2 - (\Delta X_1 Y) * \Delta X_3)/D$$

$$Coef_1 = (\Delta X_1 Y - Coef_2 * \Delta X3)/\Delta X_2$$

$$Coef_0 = (Y_1 - Coef_2 * X_2 - Coef_1 * X_1)/X_0$$

$$\Delta = \Delta X_4 * \Delta X_2 - \Delta X_3^2$$

$$\Delta X_2 = X_2 * X_0 - X_1^2$$

$$\Delta X_3 = X_3 * X_0 - X_2 * X_1$$

$$\Delta X_4 = X_4 * X_0 - X_2^2$$

$$\Delta X_2 Y = (X_2 Y_1)*X_0 - Y_1 * X_2$$

$$\Delta X_1 Y = (X_1 Y_1)*X_0 - Y_1 * X_1$$

$$X_0 = Ins\_end - Ins\_start$$

$$X_1 = \Sigma(i - Ins\_start)$$

$$X_2 = \Sigma(i - Ins\_start)^2$$

$$X_3 = \Sigma(i - Ins\_start)^3$$

$$X_4 = \Sigma(i - Ins\_start)^4$$

$$Y_1 = \Sigma F(i)$$

$$X_1 Y_1 = \Sigma(i - Ins\_start) * F(i)$$

$$X_2 Y_1 = \Sigma(i - Ins\_start)^2 * F(i)$$

Step 2: Using a 'zero crossing' method, to estimate the 'frequency' and amplitude of the snoring signal within the snoring test duration Ds as shown in FIG. F-1, we search the flow signal from the start to end of Ds in every time interval Ts=2 ms. For any 'crossing points' j where the flow signal and the approximation curve Ys cross each other (see FIG. F-1), a snoring amplitude at this crossing-point S_j is calculated and defined as:

$$S\_j = F\_var * Ts * N\_Tc$$

Where, F_var is the change of the flow signal over this crossing-point, and F_var=(F(j+1)−F(j−1)), Ts is the snoring sampling interval, which is 2 ms, and N_Tc is the number of sampling intervals around the crossing-point. In the case of FIG. 24, because the flow level at the crossing-point j is exactly equal to the value of Ys, there are two snoring sampling intervals to be included, which results in N_Tc=2, however, in most cases, N_Tc=1.

Step 3: Calculate the snoring index. If the number of 'crossing-points' over the snoring test duration is N, the total snoring amplitude is the sum of all S_j, i.e., $$S\_a = \Sigma S\_j, j=1,2,\ldots,N$$

The snoring index, S_index, is then defined as:

$$S\_index = S\_a/Ds$$

Where, Ds is the snoring test duration.

Now that we have mapped the breaths of the patient and have located the beginning of inspiration the ending of inspiration, the beginning of expiration the ending of expiration and have derived the breath durations, determined the flow rates, looked for apnea, hypopnea, and snoring, the data gathered can be used to control a machine used to treat sleep disorders. The data about the breaths can also be used to record a patient's breathing for medical studies, and for patient monitoring in general. The data can also be used in many ways to treat patients or drive machines for aiding patient breathing. The breaths are analyzed in block 10170 and divided into partitions of breath values for flow rates, snoring indexes, reduction of flow signal ranges and other parameters.

A Sleep linked Positive Air Pressure system (SPAP) controller has a collection of control rules, in block 10180 of the algorithm, that is the core of a system for controlling breathing machines.

The controller follows a number of IF-THEN statement rules for controlling breathing machines. An example of such rule structure is:

IF A is a and B is b, or C is c and D is d, THEN X is x and Y is y.

The IF part of the statement is called the antecedent or condition of the rule, and THEN part is the conclusion of the rule. The condition may include two or more parallel sub-conditions jointed together by an 'or' operator, and each sub-condition may have two or more elements connected by an 'and' operator. The conclusion of the rule may have one element or it may have two or more elements with an 'and' operator. In our nomenclature capital letters A, B, C, D, X, and Y are the variables of the condition and conclusion, and the lower cases letters a, b, c, d, x, and y are a values for each variable.

For instance, if we define the flattening index (FI), the reduction of the flow signal (RFS), inspiration flow signal level (FL), and Snoring Index (SI) as the variables of the condition in a control rule, and the changes of the pressure ($\Delta P$) and the pressure range (PR) as the variables of the conclusion. We may then define a control rule such as:

Rule: If FI is very flat (VF) and RFS is intermediate (I), or FL is moderate high (MH) and SI is mild (M), THEN $\Delta P$ is a moderate change (MC) and RP is a large range (LR).

At each control sample time, we test all the conditions in rule 1. If all elements in the conditions and any sub-condition are satisfied, then the rule 1 is active, and a command is sent to the pump such as increasing pressure to the patient. For example the pump may be directed to increase the pressure by 0.5 cmH$_2$O and keep the pressure between 4 and 20 cmH$_2$O.

It is useful to divide up the values for some of the variables into ranges such as three ranges of high, medium and low, or five ranges such as very high, high, medium, low and very low in order to define what range of a parameter is in. The ranges will help the controller in providing instructions to the machine it is controlling by setting ranges of values, which trigger different settings on the machine.

Figure 25:
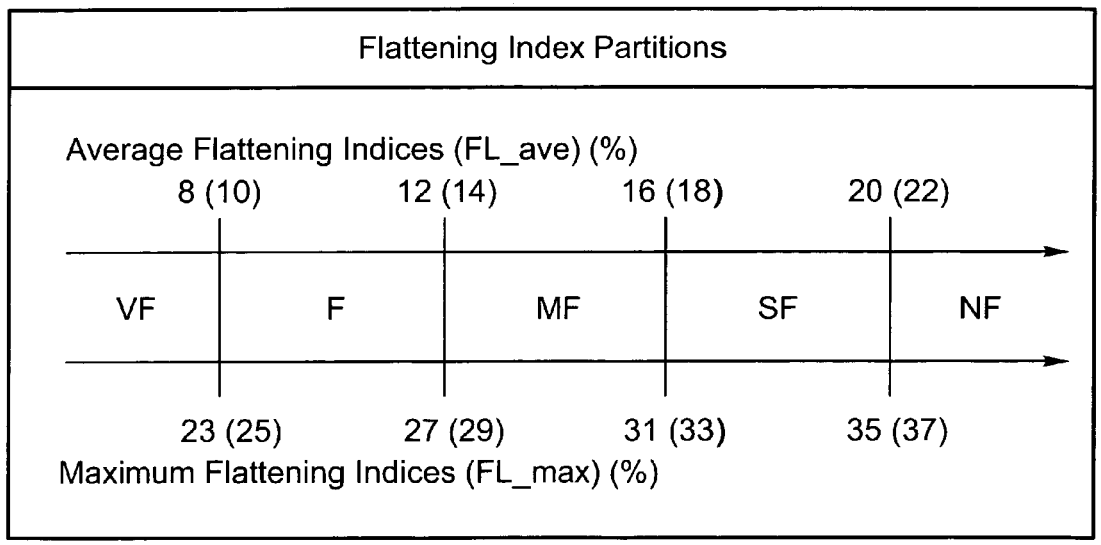
FIG. 25 is a chart showing five partitions of flattening index.
Figures 26, 27:
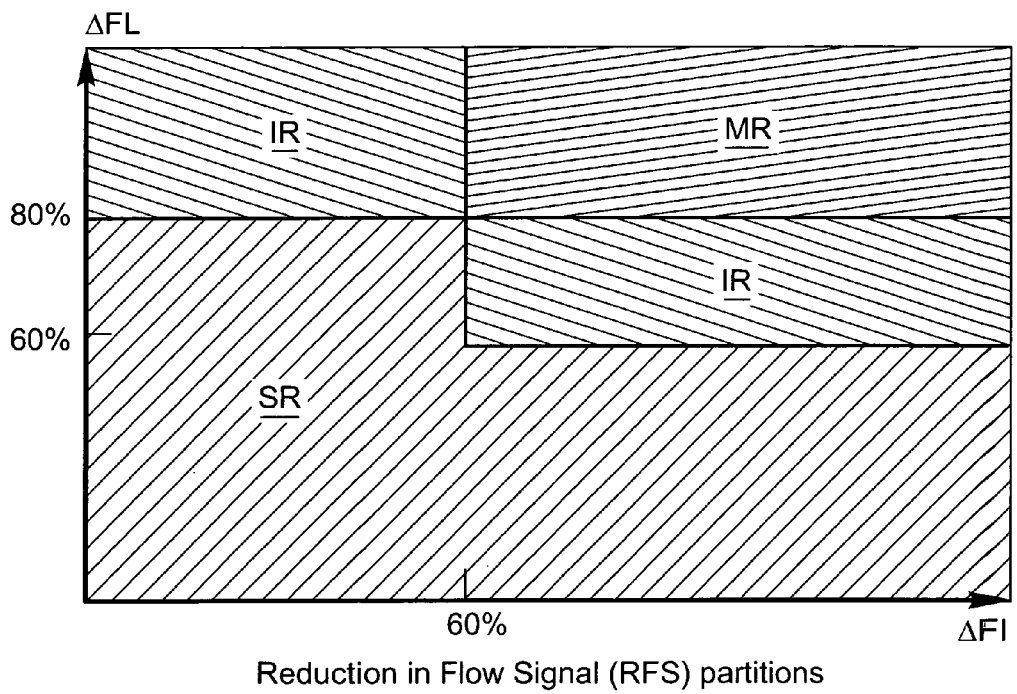
FIG. 26 is a table showing five partitions of flattening index from FIG. 25.
FIG. 27 is a chart showing reduction in flow signal levels.

Referring now to FIG. 25, which is a chart showing partitions for the FI (flattening index) values, taken from the table in FIG. 26. The spectrum of FI values are divided up into ranges or partitions defined as VF (Very Flat), F (Flat), MF (Moderately Flat), SF (Mildly Flat), and NF (Not Flat). As the chart and table shows the average flattening index is VF between 0 and 8 with a maximum flattening index of between 0 and 23. The average flattening index is F between 8 and 12 with a maximum flattening index of between 23 and 27. The average flattening index is MF between 12 and 16 with a maximum flattening index of between 27 and 31. The average flattening index is SF between 16 and 120 with a maximum flattening index of between 31 and 35. The average flattening index is NF 20 or greater and 12 with a maximum flattening index 35 or greater. The values in the brackets on the chart in FIG. 25 represent thresholds for 2 subsequent breaths and the values before the brackets represent thresholds for 3 and 5 subsequent breaths. Similarly in the table in FIG. 26 the first listed value is for 3 and 5 breaths and the second value is for two subsequent breaths.

The lower the value of the flattening index the higher the value of the upper airway resistance showing the airway is obstructed. The controller then increases the pressure applied to the patient in response to a higher degree of upper airway obstruction to treat the patient. By defining five patient states based on the average and maximum values of the flattening index different pressure increases and different maximum pressures can be applied to treat the patient according to the severity of airway obstruction.

FIGS. 26 and 27 show a table and chart respectively of values for three partitions of the RFS (reduction of the flow signal). The partitions of values are for Severe Reduction (SR), Moderate Reduction (IR) and (3) Mild Reduction'

(MR). The x-axis on the chart in FIG. 27 has FI (Flattening Index) values and the y axis has FL (flow signal level) values.

The reduction of the flow signals (RFS) used in FIGS. 26 and 27 are calculated by a combination of the changes of flattening indexes (ΔFI) and the changes of maximum flow signal levels (ΔFL). The ΔFI is defined as the relative reduction of FI_ave between the current test set and the previous test set, and the ΔFL is the relative reduction of the maximum value of the flow signal level for the current test set and that from the pervious test set. That can be represented with the following mathematical formulation:

$$\Delta FI(i) = FI\_ave(i-1)/FI\_ave(i) \%$$

$$\Delta FL(i) = FL\_max(i-1)/FL\_max(i) \%$$

The partitions shown above in the FI and FL charts and tables in FIGS. 25-28 are used extensively in the rules followed by the controller for adjusting the performance of the breathing aid machine. A set of SPAP control rules using the partitions are shown in tables 32-36. Although these rules are followed to control one type of breathing aid machine other rules may be used to accomplish the same or other goals on other machines.

The controller is alerted to a relatively more severe airway obstruction when a reduction in peak inspiratory flow and in the value of the flattening index are detected. The controller responds by relatively large pressure increases and a large maximum pressure to treat the patient.

FIGS. 29 and 30 show tables for partitions used in snoring related rules and rules with a snoring condition as part of the IF-THEN statement.

In FIG. 29 the SI is defined as a minimum value of the snoring indexes from a given test set. The SI is divided into two partitions namely No Snoring (NS) and Snoring (S) with the threshold value as 3 l/min.

In FIG. 30 the SI is the averaged value of indexes from the test set and the SI is divided into two partitions with the threshold value as 2 l/min. The range of SI is divided into two partitions namely No Snoring (NS) and Moderate Snoring (MS).

In FIG. 31 a table of snoring related control rules is shown applying the partition of table 29 to the control rules to control the average pressure applied to the patient during various snoring conditions.

The detection of snoring is another indication of upper airway obstruction and therefore a pressure increase is called for by the controller to treat the patient. If snoring is detected in conjunction with a flow limitation (i.e. a low flattening index) the controller provides a larger pressure increase than for snoring detection alone. The controller takes into consideration what the current pressure being applied is and increases the pressure in smaller increments if the pressure is already high.

Other measurements such as averaged flow leak (LK), current pressure level (CP), and time interval based flow signal and leak signal parameters may be used in control rules. The partitions of these variables differ from rule to rule.

In most cases the conclusion of the control rules change of the pressure (ΔP) and the range of pressure (RP) of air applied to the patient.

SPAP control rules can be classified into three groups according to the core variable to be used, namely flattening-related rules, snoring-related rules, and event-related rules.

The flattening-related rules are mainly for treating inspiration flow limitations. The flattening index (FI) and the measurement of reduction of flow signal (RFS) are the principal measurements used in the control rules. Since the test data was run over sets of 2, 3, and 5 breaths to calculate FI and RFS, three sub-groups of control rules are used according to different number of breathes in the test set.

FIGS. 32, 33 and 34 show tables for the control rules related to flattening of breaths for the 5 breath, 3 breath and 2 breath tests respectively.

As shown in FIG. 32 the control rules as an example, IF the Flattening Index FI is Very Flat VF and the reduction of flow signal (RFS) is a Severe Reduction (SR) THEN (according to the table) the change in pressure ΔP=0.5 cm H$_2$O and the range of pressure RP=[418] cm H$_2$O.

In the 3 breath tests the change in pressure AP for each FI/RFS combination on the table is ½ that of the 5 breath test. Similarly for the 2 breath tests the change in pressure AP for each FI/RES combination is ½ that of the 3 breath test.

A 'duplicate-rule' is used for most rules in the SPAP controller. For example, in the 5, 3 and 2 breath tables on FIGS. 32, 33 and 34 the values of the Range of Pressures are the same in each combination of FI/RES. The change of pressure ΔP is different for each test but the range of pressure is the same to avoid conflicts in the rules. The duplicate rule requires measurements from several of the most recent breaths to avoid errors due to false data, real time analysis difficulties or other anomalies.

Some common elements are used for all of the sub-groups of the flattening-related rules in the tables of FIGS. 32, 33 and 24. These common elements include: (1) The average snoring index (SI_ave), (2) the average flow leak (LK_ave), and (3) the minimum value of inspiration flow signal level from the test set (FL_min). In the 5-breath test data set, and the common elements include:

SI_ave<=2 l/min, LK_ave<=18 l/min, and
FL_min>=9 l/min

The flattening-related rules depend on the accuracy of detecting flow signal flattening which is subjected to the assumption of a reasonably small flow leakage. If the flow leak becomes larger the accuracy of detecting the flow signal flattening is limited, and as a result the control rules should become 'soft'. If the averaged flow leak is larger than 18 l/min but smaller than 47 l/min then a new set of control rules replace those in the tables of FIGS. 32, 33 and 34. In the new set of control rules the values of ΔP are the half value of that in the Tables.

In the snoring-related rules, the measurement of the snoring index and pressure play the most important roles. The two main variables are the minimum value of snoring index from the pervious breath or two consecutive breaths, denoted as SI_min, and the averaged pressure value from the previous two consequences breathes P_ave. The common elements include:

FL_min>=12 l/min and FL(i)>0.5*FL(i-1)

Where FL (i) is the flow level for the previous i-th breath.

The Table in FIG. 31 shows the snoring-related control rules for the P_ave pressure ranges and the snoring index of greater than or equal to 3 l/min.

The mixed flattening and snoring-related rules are shown in FIG. 35.

The common elements in the flattening and snoring-related rules are:

LK<=18 l/min and FL_min>=12 l/min

If there exists a case with simultaneous snoring a flattening there is clearly an obstructive event. A quick response is needed for the SPAP to increase the pump pressure, and that is the purpose of this group of the rules. The controller therefore instructs the breathing aid device to increase the by a large increment and to have a large pressure threshold for the increase in pressure. The quick response is desirable to preemptively avoid the most severe and unambiguous manifestations of obstructive sleep apnea. The main variables in this group are flattening measurement (FI) and snoring measurement (SI), and the number of breathes used in the test set is three (3) as it is necessary for the control system to detect the event within reasonable short period of time. The table in FIG. 31 shows the control rules for the 5 partitions of the flattening index FI and the Moderate Snoring (MS) partition of the Snoring Index SI.

Apnea-related rules control rules are shown in the Table of FIG. 36 shows the pressure increase rules for obstructive apneas.

Obstructive apneas are detected in two steps. The first step is detection of apnea itself with the subsequent start of forced oscillation. The condition is that the flow signal level is reduced to a low level for a longer period of time. The algorithm looks for peak to peak variation over the most recent 8 seconds—FL_var (i) as well as the previous 8 seconds—FL_var (i−1), compares the two variations and then tests the following conditions:

$FL\_var(i) <= 0.1 * FL\_var(i-1)$ $FL\_var(i) <= 0.15 * FL\_var(i-1)$ and $FL\_var(i) <= 75$ ml/s $FL\_var(i) <= 3$ l/min After forced oscillation starts, the condition is calculated and if it is small enough the apnea is considered to be obstructive and the pressure response is generated according to the Table in FIG. 36.

In the detection of hypopneas, testing is performed to see if there was any period of time in which the amplitude of the inspiration flow signal has decreased compared to nearby periods by more than a pre-defined threshold. The longer the reduced period of flow is, the more severe the hypopneas event, and the larger amount of pressure that need to be applied to the patient. The test period has a number of breathes, and the number of the breathes in the algorithm varies from 3 to 10. Both forward and backward periods consist of 2 breaths, which are the reference breaths for the flow signal in the test period. The condition for hypopneas is the maximum inspiratory flow in the test period should be smaller than minimum inspiratory flow in the reference area by at least 25%. To pick up hypopneas with gradual reduction and increase of inspiratory flow a single breath can be between the test period and any of reference period without the need of being included into the flow reduction rule.

If a hypopneas is detected the increase in pressure is defined as:

$\Delta P = 0.05 * P\_period$ (cmH2O)

With the range of pressure $RP = [4\ P\_up]$(cmH2O)

$P\_up = \max(10 + 20 * P\_period, 15)$(cmH2O)

Where, P_period is the number of breathes in the test period.

For instance, if the number of breathes in the test period is 10, we then have $\Delta P = 0.05 * P\_period = 0.05 * 10 = 0.5$(cmH2O) and $P\_up = 10 + P\_period = 10 + 10 = 20$(cmH2O), i.e., the range of the pressure is $RP = [4\ 20]$(cmH2O)

If P_period=9, and a event of hypopneas is detected, we have then needed to increased the pressure by $\Delta P = 0.5 * P\_period = 0.5 * 9 = 0.45$(cmH2O) with the range of $RP = [4\ 19]$ as $P_{13}\ up = 10 + P\_period = 10 + 9 = 19$(cmH2O), The control rules described above are all related to increasing pressure for respiratory events, such as snoring, or inspiration flow limitations are detected. After increasing the pressure to the patients, breathing can be improved and the breaths have 'normal' patterns. Once normal breathing is established, the pressure delivered to the patient is reduced gradually. There are two rules for this purpose. The variables used for detection of the 'normal' breath patterns include the averaged of the flattening indexes from the test set of 5 breathes FI_ave, snoring index for current breath SI, and current inspiration flow amplitude level FL. The output (the variables in the conclusion of the rule) is the target pressure, P_target, and time constant T_cons. That means that if breathing becomes normal the pressure is reduced to level of P_target with a time constant T_cons. The two pressure-reducing rules can be described as the following:

Rule 1: IF FI_ave>=30% and SI<=2 l/min and FL>=12 l/min, THEN P_target=4 cmH2O and T_cons=1200 s Rule 2: IF FI_ave>=25% and FL_ave<30% and SI<=2 /min and FL>=12 l/min, THEN P_target=4 cmH2O and T_cons=2400 s The last group of rules deals with the situations such large flow leak or the flow signal level remains unchanged during a relative long period of time. Under such circumstances, it is safe to reduce immediately the pump pressure to the minimum level 4 cmH2O. Therefore, the safety-related rule is applied when either a large flow leak is detected which is defined as the averaged flow leak over the last 20 breathes is larger than 1000 ml/s, or the variation of the peak-to-peak flow signal over the past 180 s is less than 250 ml/s. The safety-related rule has the highest priority, which means that:
1. When this rule is triggered it controls over all other rules for 120 s.
2. The safety-related rule can ignore any lock-out time from any other rules.

If there are no conditions from any of the above control rules are satisfied, the default control rule is applied, which is to 'DO NOTHING', i.e., the pressure remains unchanged.

Treating a patient gets very complicated since so many conditions are encountered and a patient treatment machine has to be programmed to respond to all of the possible conditions. The controller may be programmed in many different ways to use the data collected and analyzed in different ways for controlling a machine for treating a patient. In addition to the above rules 11 groups of additional pressure control rules for an automatic titration algorithm for a SPAP machine are presented.

1. Flattening Rules

Objective: When a flow limitation of air to a patient is detected by a flattening of the flow signals, flattening rules are applied to increase the pressure applied to a patient.

When Invoked: The flattening rules are invoked after any update of a sequence of respiration flow signal peaks is detected unless the forced oscillation technique is already on or a time out is still being enforced.

Main Flow Parameters: The main flow parameters are the flattening indexes for 2, 3 and 5 breaths as shown in FIG. 38. There are 4 categories of flow limitations, Severe, Large, Medium and Mild depending on the average and maximum flattening indexes of the breaths of the patient as measured over 2,3 or 5 breaths. As the flow becomes more limited for longer periods of time the higher the pressure applied to the patient for longer durations.

Tested time shifts relative to the most recent data: The tests for the flattening index to control the pressure to the patient can be taken over the current 2, 3 of 5 breath sequence or by time shifting for 1 or 2 previous breaths.

Exclusion Criteria: The Flattening Rules are Not Applied If:
 a. There are any invalid breaths out of the main breath test sequence of 2, 3 or 5 breaths or any of the 5 breaths preceding them.
 b. The minimum inspiratory flow in the main breath test sequence is less than 150 ml/s (9 l/min).
 c. The Maximum Flattening Index in the main test sequence exceeds 37 for 3 or 5 breaths or if it exceeds 35 for a 2 breath test sequence.
 d. The Average Flattening Index in the main test sequence exceeds 22 for 3 or 5 breaths or if it exceeds 20 for a 2 breath test sequence.
 e. The Average leak in the main breath test sequence exceeds 500 ml/s for a 2 or 3 breath sequence or 1000 ml/s for a 5 breath sequence.
 f. The snore peak to peak flow in the main breath test exceeds 35 ml/s for 2 and 5 breath sequences and 70 ml/s for a 3 breath sequence.

Context Considerations:
 a. Snoring. If snoring is detected during the main breath test sequence there is an increase in the likelihood of an upper airway obstruction and the pressure response/maximum can be increased. The threshold for snoring detection is the average snore peak to peak flow of 35 ml/s in the main breath test sequence of 3 breaths.
 b. Leaks If a large leak is detected it is less likely that the flattening index is being measured accurately. Therefore the values do not accurately reflect the upper airway obstructions and the pressure applied to the patient should be reduced. The threshold for a large leak is a average leak during the main test sequence of 500 ml/s over a 5 breath sequence.
 c. Reduction in average peak inspiratory flow compared to the previous 5 breath test sequence: If the average flow to the patient is decreasing the pressure applied to the patient and the maximum pressure applied should be increased. If the average leak rate is below the large leak threshold there are three categories for reduction in the average inspiratory flow.

Large reductions where the average peak inspiratory flow is no more than 60% of the average peak inspiratory flow for 5 breaths.

Small reductions where the average peak inspiratory flow is between 60% and 80% of the average peak inspiratory flow for 5 breaths.

No reductions for where the average peak inspiratory flow is above 80%.

For large reductions there are two categories of reductions. A reduction of below 70% of the threshold and no reduction.
 d. Reduction in average flattening index compared to the previous 5 breath test sequence: If a reduction in the average flatting index is detected the pressure applied to the patient should be increased since the flattening indicated a restriction in the patient's airway. The threshold for increasing the pressure applied to the patient as at a 60% reduction of the flattening index. The pressure is only increased if there are no large leaks detected. The table in FIG. 39 shows a set of rules for setting pressures applied to the patient by checking the status of the Peak Inspiratory Flow Context against the Flattening Index Context.

A set of rules for controlling a breathing aid machine such as a SPAP are presented in the table of FIG. 40. For the number of breaths in a breath sequence, and the other listed parameters, pressure changes and pressure limits are listed.

2. Hypopnea Rules

Objective: To increase the pressure applied to the patient in response to a reduction in inspiratory flow to the patient as shown by flattening indicating a hypopnea.

When invoked: After any update in the sequence of detected respiration flow signal peaks unless any of the following conditions are true:
 The FOT mode has been activated,
 timeout applicable to all rules has not expired,
 the previous hypopnea was detected within the last 15 seconds.

Main flow parameter(s): A reduction in peak inspiratory flow for a sequence of consecutive breaths. The number of breaths with reduced inspiratory flow (hypopneic breaths) in the sequence can be from 3 to 15. The whole analyzed breath sequence must include 2 reference breaths prior to the hypopneic breaths and 2 recovery breaths following the hypopneic breaths. Maximum peak inspiratory flow for the hypopneic breaths should not exceed 80% of the minimum peak inspiratory flow of the reference and recovery breaths. As change in the peak inspiratory flow pre- and post- hypopnea episode can be abrupt or gradual there could be one intermediate prehypopneic breath and one intermediate posthypopneic breath. The peak inspiratory flow of an intermediate breath should not exceed 133% of the maximum peak inspiratory flow for the hypopneic breaths and be at least 75% of the minimum peak inspiratory flow of reference (for the prehypopneic intermediate breath) or recovery (for the posthypopneic intermediate breath) breaths The longer the hypopneic sequence the larger the pressure response and the maximum pressure for which that pressure response can be activated.

Tested lime shifts relative to the most recent data: No time shift, shift by one breath into the past and shift by two breaths into the past.

Exclusion criteria. (Any one of the following):
 Any invalid breath out of all analyzed breaths for every combination of hypopnea duration and intermediate breaths,
 Average inspiratory flow in the hypopneic breath sequence less than 75 ml/s Context considerations: Flow limitation—if the average flattening index in the hypopneic breath sequence exceeds typical flow limitation values, it could be indicative of the central or artifactual origin of the hypopnea, therefore the pressure response should be reduced. An average flattening index above 30 constitutes the condition of no flow limitation and values between 26 and 30 constitute a mild flow limitation.

Actual rules: The pressure response is calculated as 0.05 $cmH_2O$ by the number of hypopneic breaths within the range 0.25 to 0.75 $cmH_2O$. If there is no flow limitation the pressure response is halved, for mild flow limitation it is multiplied by 0.75. Maximum pressure is calculated as 1 $cmH_2O$ by the number of hypopneic breaths plus 10 $cmH_2O$ within the range 15 to 20 $cmH_2O$.

3. Short Hypopnea Rules.

Objective: Increase the pressure applied to the patient in response to the detection of short hypopneas (2 hypopneic breaths). A reduction in the peak inspiratory flow is used as a measure of hypopneas.

When invoked: Breath based rules are invoked after any update in the sequence of detected respiration flow signal peaks unless any of the following conditions are true:
  FOT mode is activated,
  Timeout applicable to all rules has not expired,
  Last hypopnea was detected within 15 seconds.

Main flow parameter(s): The same as for the Short Hypopneas as shown above with the number of hypopneic breaths equal to 2.

Tested time shifts relative to the most recent data: No time shift, shift by one breath into the past and shift by two breaths into the past.

Exclusion criteria. (Any one of the following):
  Any invalid breath out of all analyzed breaths for every combination of hypopnea duration and intermediate breaths,
  Average inspiratory flow in the hyponeic breath sequence less than 75 ml/s,
  Average flattening index for hypopneic breaths above 30 and no previous apnea or hypopnea within 2 minutes.

Context Considerations:
  Flow limitation—if the average flattening index in the hypopneic breath sequence exceeds typical flow limitation values, it could be indicative of the central or artifactual origin of the hypopnea, therefore the pressure response should be reduced. An average flattening index above 30 constitutes the condition of no flow limitation and the values between 26 and 30 constitute mild flow limitation.
  Respiratory event context—If there was a previous apnea or hypopnea within 2 minutes, then there is no pressure change. However the time instant is stored to provide respiratory event context for possible future events.
  Actual rules: The pressure response is 0.25 cmH$_2$O. If there is no flow limitation the pressure response is halved. For mild flow limitation the pressure response is multiplied by 0.75. Maximum pressure is 15 cmH$_2$O.

4. Smooth Hypopnea Rules

Objective: To increase the pressure applied to the patient in response to hypopneas with a very gradual reduction in flow rates by applying a small increase in peak inspiratory flow. These hypopneas cannot be detected with the short hypopnea rules or the hypopnea rules as show above. A reduction in the peak inspiratory flow is still used as a measure of hypopneas however the reference and recovery breath sequences defined differently from the short hypopnea rules or the hypopnea rules as show above.

When invoked: The breath based rules are invoked after any update in the sequence of detected respiration flow signal peaks unless any of the following conditions are true:
  FOT mode is activated,
  a timeout applicable to all rules has not expired,
  the last hypopnea was detected within 15 seconds.

Main flow parameter(s). A sequence of breaths with a gradual reduction in peak respiratory flow is detected as a reference that preceded a hypopnea (however it is impossible to unambiguously identify the fist hypopneic breath due to a gradual change in peak inspiratory flow). The reference sequence should have at least 3 breaths. The criteria for the gradual peak inspiratory flow reduction allows for one of the following types of patterns:

A continuous reduction in the peak inspiratory flow, i.e. the peak inspiratory flow of any subsequent breath is less than the peak inspiratory flow of the preceding breath, If the peak inspiratory flow of any subsequent breath is more than or equal to the peak inspiratory flow of the preceding breath, then two conditions should be complied with, that (former) peak inspiratory flow should be less than 90% of the pre-preceding breath and the peak respiratory flow for the breath after the subsequent breath should be less than 90% of the peak inspiratory flow of the preceding breath.

Similarly a sequence of breaths with a gradual increase in the peak inspiratory flow should be detected as a recovery pattern following the reference sequence. The rules for the recovery sequence mirror the rules for the reference sequence. The maximum peak inspiratory flow for the initial reference and for the last recovery breaths not should be more than 175% of the minimum peak inspiratory flow for those breaths. The sequence of hypopneic breaths should be that a first breath is located not later than the breath following the reference sequence, and a last breath located not earlier than the breath preceding the recovery sequence, with at least 3 hypopneic breaths and at least 3 breaths in the reference and recovery sequences after excluding the hypopneic breaths. The hypopnea event is detected if the maximum peak inspiratory flow for the hypopneic breaths is no more than 75% of the minimum peak inspiratory flow for the initial reference and the last recovery breaths.

Tested time shifts relative to the most recent data: No time shift and shift by one breath into the past.

Exclusion criteria. (Any one of the following):
  Any invalid breath out of all reference, hypopneic and recovery breaths,
  Average inspiratory flow in the hypopneic breath sequence less than 75 ml/s
  Duration of hypopneic breaths exceeds 100 s.

Context considerations: The flow limitation—if the average flattening index in the hypopneic breath sequence exceeds typical flow limitation values it may indicate a central or artifactual origin of the hypopnea, therefore the pressure response should be reduced. An average flattening index above 30 constitutes a condition of no flow limitation and a flattening index between 26 and 30 constitutes mild flow limitation.

Actual rules: The pressure response is calculated as 0.05 cmH$_2$O by the number of hypopneic breaths within the range 0.25 to 0.75 cmH$_2$O. If there is no flow limitation, the pressure response is halved. For a mild flow limitation the pressure response is multiplied by 0.75. For a maximum flow limitation the pressure response is 1 cmH$_2$O times the number of hypopneic breaths plus 10 cmH$_2$O within the range 15 to 20 cmH$_2$O.

5. Post Recovery Apnea Rules

Objective: To increase pressure in response to apneas. Typically this rule will generate a pressure change in response to short apneas when the breathing recovery happens before a FOT response can be analyzed. A reduction in the peak to peak flow is used as a measure for the apnea.

When invoked: Breath based rules are invoked after an update in the sequence of detected respiration flow signal peaks unless one of the following conditions are true:
  A timeout applicable to all rules has not expired,
  The last hypopnea was detected within 15 seconds,
  The last apnea was detected within 10 seconds.

Main flow parameter(s). The recovery flow is calculated as a peak to peak flow variation between the start of inspiration of the second last breath in the test sequence and the end inspiration in the last breath in the test sequence (recovery time interval). The reference breath pair is any two consecutive breaths prior to the last two breaths in the test sequence such that there is a drop in the peak to peak flow variation between the reference and recovery breath pairs. The reference flow is calculated as a peak to peak flow variation between the start of inspiration of the first breath in the reference pair and the end of inspiration in the last breath in the reference pair (reference time interval). The apneic flow is a peak to peak flow variation for the time interval between the end of the reference time interval and the start of the recovery time interval (apnea time interval). The recovery and reference flows should exceed 200 ml/s and should not differ by a ratio exceeding 2 to 1. The apnea time interval should be at least 8 seconds and the apneic flow should not exceed 20% of the reference or recovery flow.

Tested time shifts relative to the most recent data: No time shift, shift by one breath into the past and shift by two breaths into the past.

Exclusion criteria: Any invalid breath out of all reference or recovery breath pair.

Context Considerations.

Respiratory event context—previous apnea or hypopnea within 2 minutes. If this condition is true then there is no pressure change however the time instant is stored to provide respiratory event context for the possible future event.

Mask pressure—the higher the current pressure the smaller the magnitude of the response should be.

Actual rules: If the average pressure over the last 5 seconds is no more than 6 cmH$_2$O, the pressure increase is 1 cmH$_2$O. If the average pressure over the last 5 seconds is no more than 12 cmH$_2$O, the pressure increase is 0.75 cmH$_2$O, otherwise the pressure increase is 0.5 cmH$_2$O. The maximum pressure applied is 20 cmH$_2$O, time constant is 5 s. If the FOT has been on, it is stopped.

6. Snoring Rules

Objective: To increase the pressure applied to the patient in response to snoring. The patient is considered to be snoring if the average peak to peak snoring flow contains inspiratory flow oscillations above 10 Hz.

When invoked: Breath based rules are invoked after any update in the sequence of detected respiration flow signal peaks unless any of the following conditions are true:
  FOT mode is activated,
  A timeout applicable to all rules has not expired.

Main flow parameter(s): The minimum snore flow in the breath test sequence (1 or 2 breaths) should be at least 60 ml/s.

Tested time shifts relative to the most recent data. Shift by one, two and three breaths into the past.

Exclusion criteria. (Any one of the following):
  Any invalid breath out of the test sequence,
  Maximum expiratory high frequency noise in the test sequence is at least 90% of the minimum snore flow,
  Minimum peak inspiratory flow is under 100 ml/s (6 l/mm) if 2 breath test and under 200 ml/s (12 l/mm) if I breath test
  Minimum peak inspiratory flow for the test sequence is less than a half of the peak inspiratory flow of the preceding breath.

Context Considerations:
  The ratio of the maximum expiratory high frequency noise in the test sequence to the minimum snore flow is considered. The larger the ratio the larger the likelihood of an incorrect snore evaluation, therefore the pressure response should be reduced. The confidence coefficient is 1 minus the ratio. If confidence coefficient exceeds 0.5 it is set to 1.
  Mask pressure—the higher the current pressure the smaller the magnitude of the response. The average pressure is calculated from the last breath in the test sequence and the preceding breath.

Actual rules are calculated according to the table in FIG. 41.

7. Pressure Drop Rules

Objective: To immediately drop pressure (to 4 cmH$_2$O or by 1 cmH$_2$O) if no reliable flow signal is measured.

When invoked: The time based rules for dropping the pressure are invoked after any update in the sequence of detected respiration flow signal peaks or after the 2 second timeout when the last respiratory peak update has expired unless either the
  FOT mode is activated, or
  A timeout applicable to all rules has not expired.

Main flow parameter(s). Peak to peak flow variation over the last 2 minutes below 250 ml/s and average leak over the last 20 seconds above a threshold (that depends on the average peak inspiratory flow).

Tested time shifts relative to the most recent data are not applicable.

Exclusion criteria are not applicable

Context considerations: Peak inspiratory flow, The smaller the peak inspiratory flow is the larger the errors due to leaks.

Actual rules. The pressure is dropped to 4 cmH$_2$O if the peak to peak flow is small (as in main flow parameters) or for the following combinations of average leak and average peak inspiratory flow over the last 20 seconds.

>=1000 ml/s (60 l/mm), <=100 ml/s (6 l/min)

>=1200 ml/s (72 l/mm), <=150 ml/s (9 l/min)

>=1400 ml/s (84 l/mm), <=200 ml/s (12 l/min)

In this case the timeout of 2 minutes applicable to all rules is set, Otherwise if the average leak is at least 1000 ml/s (60 l/min) the pressure is reduced by 1 cmH$_2$O and the timeout is set to 20 seconds.

8. Start Forced Oscillation Technique Rules

Objective: To start the FOT if peak to peak flow reduction is detected.

When invoked: The time based rules are invoked after any update in the sequence of detected respiration flow signal peaks or after the 2 s timeout after the last respiratory peak update has expired unless any of the following conditions are true:
  FOT mode is activated,
  Timeout applicable to all rules has not expired,
  Previous FOT start event was activated within 15 seconds.

Main flow parameter(s). If there is a peak to peak flow variation over the last 3 seven second intervals (last, second and first) and the last flow variation does not exceed $\frac{1}{10}$th of the second one, or does not exceed $\frac{1}{7}$th and 75 ml/s, or does not exceed 50 ml/s, and the maximum of the second and first flow variations is at least 150 ml/s the rule is activated.

Tested time shifts relative to the most recent data are not applicable.

Exclusion criteria are not applicable.

Context considerations are not applicable.

Actual rules: In addition to starting FOT the timeout applicable to all rules is set to 4 seconds.

9. Forced Oscillation Technique Apnea Rules

Objective: To increase pressure to the patient in response to detected apneas after the FOT has started. A low value of airway conductance is used as an indicator of the existence of an obstructive apnea.

When invoked: The time based rules are invoked after any update in the sequence of detected respiration flow signal peaks or after the 2 second timeout when the last respiratory peak update has expired unless any of the following conditions are true:

FOT mode is not activated,
Timeout applicable to all rules has not expired,
Previous apnea event was activated within 10 s.
Main flow parameter(s): Peak to peak flow variation over the last 5 seconds below 100 ml/s and average airway conductance over the last 5 seconds is below the threshold.

Tested time shifts relative to the most recent data are not applicable.

Exclusion criteria are not applicable.

Context considerations: The higher the current mask pressure the smaller magnitude of the response should be.

Actual rules: If the average pressure over the last 5 seconds is no more than 6 cmH$_2$O the pressure increase is 2 cmH$_2$O, if average pressure over the last 5 seconds is no more than 12 cmH$_2$O, the pressure increase is 1 cmH$_2$O, otherwise the pressure increase is 0.5 cmH$_2$O. The maximum pressure is 20 cmH$_2$O, the time constant is 5 seconds. FOT is stopped.

10. Pressure Reduction Rules

Objective: To gradually reduce the pressure applied to the patient in response to absence of flow limitation as measured by a flattening index.

When invoked: Breath based rules are invoked after any update in the sequence of detected respiration flow signal peaks unless any of the following conditions are true:

FOT mode is activated,
Timeout applicable to all rules has not expired.
Main flow parameter(s). The average flattening index in the breath test sequence (5 breaths) should exceed 25. If it is less than 33 the pressure reduction time constant is 40 minutes, otherwise it is 20 minutes.

Tested time shifts relative to the most recent data: No time shift, shift by one breath into the past and shift by two breaths into the past.

Exclusion criteria: (Any one of the following):
Any invalid breath out of the test sequence,
Last respiratory event (apnea or hypopnea) was detected within 90 seconds.
Snore flow for the last breath in the test sequence exceeds 40 ml/s
Peak inspiratory flow for the last breath test sequence is less than 200 ml/s
Context considerations: If the last respiratory event is within 2 minutes (but earlier than 1.5 minutes in the past) the time constant is doubled.

Actual rules: Reduce the pressure applied to the patient from its current value to 4 cmH$_2$O with the selected time constant.

11. Stop Forced Oscillation Technique Rules

Objective.: To stop treating the patient once breathing recovers to normal.

When invoked: Breath based rules are invoked after any update in the sequence of detected respiration flow signal peaks unless any of the following conditions are true:

FOT mode is not activated,
Timeout applicable to all rules has not expired.

Main flow parameter(s): The minimum peak inspiratory in the breath test sequence (3 breaths) should exceed 200 ml/s (12 l/min).

Tested time shifts relative to the most recent data: No time shift.

Exclusion criteria: Any invalid breath out of the test sequence.

Context considerations are not applicable.

Actual rules are not applicable.

Obviously, many modifications and variations of the present invention are possible in light of the above teachings. It is therefore to be understood that, within the scope of the appended claims, the invention may be practiced otherwise than as specifically described.

What is claimed is:

1. A breath monitoring and treating method comprising:
   collecting flow rate data of air applied to a patient,
   compiling the flow rate data into inspiration arrays and expirations arrays by approximating the start and end times of the inspirations and expirations, and determining, with a processor and memory, the maximum peak flow rates during inspiration and minimum peak flow rates during expiration from the flow rate data,
   adjusting, with the processor and memory, the start and end times of the inspirations and expirations in the arrays of flow rate data to best fit the flow rate data collected.

2. A breath monitoring and treating method as in claim 1 including the further step of:
   removing noise from the array of flow rate data.

3. A breath monitoring and treating method as in claim 2 including the further step of:
   using a linear smoothing technique for removing the noise.

4. A breath monitoring and treating method as in claim 1 including the further step of:
   collecting pressure data of the air applied to the patient.

5. A breath monitoring and treating method as in claim 4 including the step of:
   adjusting the pressure applied to the patient based on a flow rate data analysis.

6. A breath monitoring and treating method as in claim 5 including the step of:
   using a snoring index to adjust the pressure applied to a patient.

7. A breath monitoring and treating method as in claim 5 including the step of:
   using a flattening index to adjust the pressure applied to a patient.

8. A breath monitoring and treating method as in claim 5 including the step of:
   changing the pressure applied to a patient within a predetermined range based on the current pressure applied to the patent, a flattening index of a reduction in the flow of air applied to a patient, and a snoring index of the degree of snoring.

9. A breath monitoring and treating method as in claim 8 including the step of:
   changing the pressure applied to a patient based on the number of breaths measured in the flow rate data analysis.

10. A breath monitoring and treating method as in claim 5 including the step of:
    determining an inspiration flow amplitude from the flow rate data of air applied to a patient, changing the pressure applied to a patient within a predetermined range based on the current pressure applied to the patent and the inspiration flow amplitude.

11. A breath monitoring and treating method as in claim 10 including the step of:
changing the pressure applied to a patient based on the number of breaths measured in the flow rate data analysis.

12. A breath monitoring and treating method as in claim 10 including the step of:
using a leakage rate combined with the flattening index to determine the change in pressure applied to the patient.

13. A breath monitoring and treating method as in claim 4 including the step of:
changing the pressure applied to the patient based on the current pressure applied and the snoring index.

14. A breath monitoring and treating method as in claim 13 including the step of:
changing the pressure applied to the patient based on the flow level of air applied to the patient.

15. A breath monitoring and treating method as in claim 14 including the step of:
changing the pressure applied to the patient based on the flattening index.

16. A breath monitoring and treating method as in claim 4 including the step of:
reducing the pressure of air applied to a patient when normal breathing is established.

17. A breath monitoring and treating method as in claim 4 including the step of:
reducing the pressure of air applied to a patient when leak rates reach a predetermined level over a predetermined length of time.

18. A breath monitoring and treating method as in claim 4 including the step of:
making no changes of pressure applied to the patient when no changes are detected in the patient and when no rules for changing the pressure apply.

19. A breath monitoring and treating method as in claim 1 including the further step of:
calculating leak compensation rates to subtract the leak rate from the measured rate to determine the flow rate of air applied to the patient.

20. A breath monitoring and treating method as in claim 1 including the further step of:
comparing inspiration flow rate data to expiration flow rate data as an accuracy check.

21. A breath monitoring and treating method as in claim 20 including the further step of:
comparing inspiration volume data to expiration volume data as an accuracy check.

22. A breath monitoring and treating method as in claim 20 including the further step of:
comparing inspiration end time data to expiration start time data and comparing inspiration start time data to expiration end time data as an accuracy check.

23. A breath monitoring and treating method as in claim 1 including the further step of:
compiling the flow rate data into breath shapes,
adjusting the start and end times for each inspiration and expiration from the breath shapes obtained from the flow rate data.

24. A breath monitoring and treating method as in claim 1 further comprising:
finding break points for approximating the start and end times of inspirations and expirations.

25. A breath monitoring and treating method as in claim 24 including the step of:
collecting raw data for inspirations, smoothing the raw data for the first inspiration in the array with a linear smoothing process and then attaching raw data collected for the next inspiration to the smoothed data and smoothing the raw data of the next inspiration with the linear smoothing process to compile an inspiration array of flow rate data and eliminate noise from the data and repeating the attaching and smoothing of new inspiration data collected until the array is completed to compile the flow data into inspiration arrays.

26. A breath monitoring and treating method as in claim 25 including the step of:
attaching the inspiration raw data to the array of smoothed data by matching the break point end of the inspiration of the previous breath to the break point of the raw data of the succeeding breath by a best fit method, adjusting the array accordingly and then linearly smoothing the raw data to form the inspiration array.

27. A breath monitoring and treating method as in claim 26 wherein the best fit method includes:
attaching the end of the inspiration break point of a first breath to a local minimum data point in the raw data of the next breath when the next breath raw data is available before the end of inspiration break point data is available and the next breath raw data starts at a lower value than the end of inspiration break point of the previous breath.

28. A breath monitoring and treating method as in claim 26 wherein the best fit method includes:
attaching the end of inspiration break point of a first breath to the start of the next breath inspiration break point when they have the same or approximately the same value and the calculated start of inspiration break point is available at approximately the same time as the calculated value of the end of inspiration break point of the previous inspiration.

29. A breath monitoring and treating method as in claim 26 wherein the best fit method includes:
attaching a point on the smoothed inspiration data as the inspiration break point to a local minimum data point in the raw data of the next breath at a point where the smoothed data and the raw data overlap when the next breath raw data is available before the end of inspiration break point data is available and the next breath raw data start of inspiration break point starts at a higher value than the end of inspiration break point.

30. A breath monitoring and treating method as in claim 26 wherein the best fit method includes:
attaching the end of inspiration break point of a first breath to the raw data of the next breath at a point where the raw data equals the end of the inspiration break point when the next breath raw data is available approximately simultaneously with the smoothed data such that they nearly overlap in time and the next breath raw data extends to a lower value than the end of the inspiration break point of the first breath.

31. A breath monitoring and treating method as in claim 26 wherein the best fit method includes:
attaching the end of inspiration break point of a first breath to the raw data of the next breath starting break point where there is a time gap between the first breath smoothed and the next breath starting break point raw data being available by filling in the gap using the slope of the linearly smoothed inspiration between the maximum and the end of breath break point as the slope of the line to fill in the gap, and moving the time of the next breath starting break point to intercept the line filling the gap.

32. A breath monitoring and treating method as in claim 26 including the step of:

checking the inspiration array for two maximum peaks within a specified time between the starting break point and the ending break point of the inspiration which indicates a double peak, linearly smoothing the inspiration by selecting the maximum peak nearest the half duration of the inspiration as the true maximum peak and linearly smoothing the maximum peak to the starting break point and the ending break point.

33. A breath monitoring and treating method as in claim 32 including the step of: identifying noisy maximum peaks in the array of inspiration peaks.

34. A breath monitoring and treating method as in claim 33 including the step of:
using a series of duration between local peaks tests and variations of flow rates between the peaks tests for determining which breaths fit within a predetermined threshold of parameters defining a noisy breath.

35. A breath monitoring and treating method as in claim 33 including the step of:
examining the upward slope of each inspiration in the array first to see if there is a noisy slope and if no noisy slope is found then checking the downward slope of each inspiration in the array to see if there is a noisy slope.

36. A breath monitoring and treating method as in claim 33 including the step of:
smoothing noisy maximum peaks found in the array by a least error selection made from a first order linear approximation, a second order liner approximation and a third order linear approximation.

37. A breath monitoring and treating method as in claim 36 including the step of:
comparing inspiration volumes to adjacent breath expiration volumes in an array of breaths for approximately the same volume of inspiration and expiration as a check on the accuracy of the data collected.

38. A breath monitoring and treating method as in claim 37 including the step of:
accepting the data as accurate if the inspiration volume approximately equals the adjacent breath expiration volume.

39. A breath monitoring and treating method as in claim 37 including the step of:
rejecting the data as inaccurate if the inspiration volume does not approximately equal the adjacent breath expiration volume.

40. A breath monitoring and treating method as in claim 38 including the step of:
testing the raw data between two peaks in a maximum pair to see if any peaks are above a specified threshold which disqualifies the two peaks as a maximum pair.

41. A breath monitoring and treating method as in claim 40 including the step of:
testing the duration between maximum peaks for a predetermined range of values, if the duration is not within the predetermined range the maximum pair is disqualified.

42. A breath monitoring and treating method as in claim 41 including the step of:
graphing the variation of the flow rate in a maximum pair raw data set having a first maximum peak and a second maximum peak, and linearly smoothing the raw data showing the decreasing values as they decrease between the first maximum peak in the maximum pair and a minimum point, the graph showing no change during increasing variations, and showing the increasing values between the minimum point and the second maximum peak of the maximum pair, while showing no change during decreasing variations and noting the points at which the variations decrease to their 95 percentage points, their 75 percentage points, their 50 percentage points, their 25 percentage points, and their 5 percentage points, of the variation from the first maximum peak and noting the points at which the variations increase from their 5 percentage points, their 25 percentage points, their 50 percentage points, their 75 percentage points, their 95 percentage points, from the second maximum peak in the maximum pair.

43. A breath monitoring and treating method as in claim 42 including the step of:
compiling the differences in variations between the raw data and the linearly smoothed data at the 5%, 25%, 50%, 75% and 95% positions.

44. A breath monitoring and treating method as in claim 43 including the step of:
forming maximum trains out of maximum pairs using a similarity test on the maximum pairs to select which maximum pairs to add to the maximum train.

45. A breath monitoring and treating method as in claim 44 including the step of:
calculating the mean, standard deviation, average and maximum error for each of the following maximum pair parameters; the duration, the variation in signal level in external duration, the average signal level in the internal duration signal, asymmetry measures of shape, signal 'shape' in external duration, signal 'shape' in internal duration, average noise level, and maximum noise level.

46. A breath monitoring and treating method as in claim 45 including the step of:
establishing mean index and error index values based on ranges of values on a predetermined table for adding maximum pairs to a maximum train.

47. A breath monitoring and treating method as in claim 44 including the step of:
verifying the maximum trains by comparing the inspiration maximum train starting break points to the expiration maximum train expiration ending break points and the inspiration maximum train ending break points to the expiration maximum train expiration beginning break points.

48. A breath monitoring and treating method as in claim 47 including the step of:
adding a maximum peak from the raw data if the inspiration and expiration break points do not match and the duration between maximum peaks is longer than a predefined threshold by left and right side maximum peak verification.

49. A breath monitoring and treating method as in claim 48 including the step of:
using flow rate signal level verification, to see if the signal level remains constant indicating the mask may have come off and the maximum pair must then be eliminated from the maximum train.

50. A breath monitoring and treating method as in claim 48 including the step of:
testing the duration between two maximum peaks and the volume of the inspirations as measured by the area under the maximum peaks, if the duration and volume are not within predetermined limits the maximum pairs are too close together and the smaller amplitude maximum peak is eliminated from the array.

51. A breath monitoring and treating method as in claim 48 including the step of:

testing the duration between two maximum peaks for durations that exceed predetermined limits and adding back maximum peaks to the array if the two tests are passed, a 4 second duration test and, a 10 second verification test.

52. A breath monitoring and treating method as in claim 48 including the step of:
shaping the inspiration and expiration data by a best fit method employing a piece wise linear approximation of the breath shape.

53. A breath monitoring and treating method as in claim 52 including the step of:
using a third order piecewise linear approximation to determine the breath shape.

54. A breath monitoring and treating method as in claim 53 including the step of:
comparing the relative changes of the flow signal level at the break points to find the beginning of inspiration and the ending inspiration times to fine tune the break points.

55. A breath monitoring and treating method as in claim 1 including the step of:
shaping the inspiration and expiration data by a best fit method employing a piece wise linear approximation of the breath shape.

56. A breath monitoring and treating method as in claim 55 including the step of:
using a third order piecewise linear approximation to determine the breath shape.

57. A breath monitoring and treating method as in claim 56 including the step of:
fine tuning the start and end break points of the inspirations and expirations by a comparison of the relative changes of flow signal level at the start and end times of the inspirations to find the beginning of inspiration and the ending inspiration times.

58. A breath monitoring and treating method as in claim 1 including the step of:
detecting reductions of inspiration flow rates in the inspiration arrays to identify apnea events.

59. A breath monitoring and treating method as in claim 1 including the step of:
detecting flattening of the inspiration flow rates in the inspiration arrays.

60. A breath monitoring and treating method as in claim 59 including the step of:
using a least square error method to find the smallest flattening error in the inspiration flow rate data to yield a flattening index.

61. A breath monitoring and treating method as in claim 60 including the step of:
using a best fit of a two dimensional searching method for detecting the flattening index.

62. A breath monitoring and treating method as in claim 61 including the step of:
using a straight line length of 60% of the inspiration interval for detecting the flattening index.

63. A breath monitoring and treating method as in claim 60 including the step of:
using the flattening index to determine the degree of blockage of the patient's airway.

64. A breath monitoring and treating method as in claim 1 including the step of:
determining the inspiration flow amplitude from the flow rate data and using the inspiration flow amplitude to identify if the patient is experiencing apnea.

65. A breath monitoring and treating method as in claim 64 including the step of:
measuring the air pressure applied to the patient, measuring the flow rate applied to the patient and changing the pressure applied to the patient according to a predetermined formula.

66. A breath monitoring and treating method as in claim 1 including the step of:
determining the inspiration flow amplitude from the flow rate data and using the inspiration flow amplitude to identify if the patient is experiencing hypopnea.

67. A breath monitoring and treating method as in claim 66 including the step of:
measuring the air pressure applied to the patient, measuring the flow rate applied to the patient and changing the pressure applied to the patient according to a predetermined formula.

68. A breath monitoring and treating method as in claim 1 including the step of:
detecting reductions of inspiration flow rates to identify hypopnea events.

69. A breath monitoring and treating method as in claim 1 including the step of:
detecting snoring by measuring the amount of noise in terms of amplitude and frequency.

70. A breath monitoring and treating method as in claim 1 including the step of:
detecting snoring by use of a snoring index.

71. A breath monitoring and treating method as in claim 1 including the step of:
detecting a high frequency flow rate on top of the flow rate signal to identify snoring.

72. A breath monitoring and treating method as in claim 1 including the step of:
detecting flattening of the inspiration flow rates in the inspiration arrays and establishing a flattening index based on the degree of flattening to assign a value to the inspiration flow.

73. A breath monitoring and treating method as in claim 1 including the step of:
determining a flattening index for measuring patient inspiration flow limitations such as apneas and hypopneas.

74. A breath monitoring and treating method as in claim 1 including the step of:
determining a straight line flow approximation of the flow rate data between an inspiration start time and an inspiration end time by a least square error method, determining the least error of the flow signal relative to the straight line flow approximation to calculate the flattening index.

75. A breath monitoring and treating method as in claim 74 including the step of:
selecting a set of flow signal data having an inspiration period length of 60% of the time between the start and end times of an inspiration, and testing for the least square error between the 5% and 95% of the inspiration period length to perform horizontal searching for a reference straight line flow approximation.

76. A breath monitoring and treating method as in claim 75 including the step of:

detecting the crossing points of the straight line flow approximation on the flow rate data and only using the period between the crossing points and the flow rate date from above the straight line flow approximation and below the flow rate data to calculate the errors and using a vertical line displacement of the straight line flow approximation line to find the least error.

77. A breath monitoring and treating method as in claim 75 including the step of:

calculating the flattening index by the error between the flow signal data and the flat signal level.

* * * * *